(12) United States Patent
Krishnan et al.

(10) Patent No.: US 10,006,083 B2
(45) Date of Patent: *Jun. 26, 2018

(54) NUCLEIC ACID SAMPLE PREPARATION

(71) Applicant: BIOLOGICAL DYNAMICS, INC., San Diego, CA (US)

(72) Inventors: Rajaram Krishnan, San Diego, CA (US); David J. Charlot, San Diego, CA (US); Eugene Tu, San Diego, CA (US); James McCanna, San Diego, CA (US); Lucas Kumosa, Centennial, CO (US); Paul D. Swanson, Santee, CA (US); Robert Turner, San Diego, CA (US); Kai Yang, San Diego, CA (US); Irina Dobrovolskaya, San Diego, CA (US); David Liu, San Diego, CA (US); Juan Pablo Hinestrosa Salazar, San Diego, CA (US); Juscilene Menezes, Del Mar, CA (US)

(73) Assignee: BIOLOGICAL DYNAMICS, INC., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/320,730

(22) PCT Filed: Jun. 19, 2015

(86) PCT No.: PCT/US2015/036789
§ 371 (c)(1),
(2) Date: Dec. 20, 2016

(87) PCT Pub. No.: WO2015/196141
PCT Pub. Date: Dec. 23, 2015

(65) Prior Publication Data
US 2017/0137870 A1    May 18, 2017

Related U.S. Application Data

(63) Continuation of application No. 14/311,037, filed on Jun. 20, 2014, now Pat. No. 8,932,815, which is a continuation-in-part of application No. 14/067,841, filed on Oct. 30, 2013, now Pat. No. 9,206,416, which is a continuation of application No. 13/864,179, filed on Apr. 16, 2013, now Pat. No. 8,603,791.

(60) Provisional application No. 61/624,897, filed on Apr. 16, 2012.

(51) Int. Cl.
| | | |
|---|---|---|
| C12Q 1/68 | (2018.01) | |
| C12Q 1/6825 | (2018.01) | |
| C12Q 1/6806 | (2018.01) | |
| C12Q 1/6869 | (2018.01) | |
| C12N 13/00 | (2006.01) | |
| G01N 27/447 | (2006.01) | |

(52) U.S. Cl.
CPC ......... *C12Q 1/6825* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,632,957 | A | 5/1997 | Heller et al. |
| 5,958,791 | A | 9/1999 | Roberts et al. |
| 6,149,789 | A | 11/2000 | Benecke et al. |
| 6,203,683 | B1 | 3/2001 | Austin et al. |
| 6,280,590 | B1 | 8/2001 | Cheng et al. |
| 6,294,063 | B1 | 9/2001 | Becker et al. |
| 6,335,167 | B1 | 1/2002 | Pinkel et al. |
| 6,403,367 | B1 | 6/2002 | Cheng et al. |
| 6,557,575 | B1 | 5/2003 | Gerhardt et al. |
| 6,749,736 | B1 | 6/2004 | Fuhr et al. |
| 6,824,664 | B1 | 11/2004 | Austin et al. |
| 6,887,362 | B2 | 5/2005 | Huang et al. |
| 7,081,189 | B2 | 7/2006 | Squires et al. |
| 7,105,081 | B2 | 9/2006 | Gascoyne et al. |
| 7,709,262 | B2 | 5/2010 | Cantor et al. |
| 8,425,750 | B2 | 4/2013 | Sugioka |
| 8,603,791 | B2 | 12/2013 | Krishnan et al. |
| 8,815,554 | B2 | 8/2014 | Krishnan et al. |
| 8,815,555 | B2 | 8/2014 | Krishnan et al. |
| 8,871,481 | B2 | 10/2014 | Krishnan et al. |
| 8,877,470 | B2 | 11/2014 | Krishnan et al. |
| 8,932,447 | B2 | 1/2015 | Heller et al. |
| 8,932,815 | B2 | 1/2015 | Krishnan et al. |
| 8,969,059 | B2 | 3/2015 | Krishnan et al. |
| 9,005,941 | B2 | 4/2015 | Krishnan et al. |

(Continued)

FOREIGN PATENT DOCUMENTS

| | | |
|---|---|---|
| CN | 1337580 A | 2/2002 |
| CN | 1348100 A | 5/2002 |

(Continued)

OTHER PUBLICATIONS

Copending U.S. Appl. No. 15/469,406, filed Mar. 24, 2017.
PCT/US2017/024149 International Search Report and Written Opinion dated Jul. 18, 2017.
PCT/US2017/024149 Invitation to Pay Additional Fees dated May 15, 2017.
U.S. Appl. No. 12/936,147 Office Action dated Mar. 17, 2017.
U.S. Appl. No. 15/293,062 Office Action dated Mar. 22, 2017.
Angerer et al. Demonstration of tissue-specific gene expression by in situ hybridization. Methods Enzymol 152:649-660 (1987).
Asbury et al. Trapping of DNA by dielectrophoresis. Electrophoresis 23:2658-2666 (2002).
Asbury et al. Trapping of DNA in Nonuniform Oscillating Electric Fields. Biophys J. 74:1024-1030 (1998).
Becker et al. Separation of Human Breast Cancer Cells From Blood by Differential Dielectric Affinity. Proceedings of the National Academy of Sciences 92:860-864 (1995).
Becker et al. The removal of human leukemia cells from blood using interdigitated microelectrodes. J Phys. D: Appl. Phys. 27:2659-2662 (1994).

(Continued)

*Primary Examiner* — James Martinell
(74) *Attorney, Agent, or Firm* — Wilson, Sonsini, Goodrich & Rosati

(57) ABSTRACT

The present invention includes methods, devices and systems for isolating a nucleic acid from a fluid comprising cells. In various aspects, the methods, devices and systems may allow for a rapid procedure that requires a minimal amount of material and/or results in high purity nucleic acid isolated from complex fluids such as blood or environmental samples.

20 Claims, 15 Drawing Sheets

(56) References Cited

U.S. PATENT DOCUMENTS

| | | | |
|---|---|---|---|
| 9,034,578 | B2 | 5/2015 | Krishnan et al. |
| 9,034,579 | B2 | 5/2015 | Krishnan et al. |
| 9,206,416 | B2 | 12/2015 | Krishnan et al. |
| 9,387,489 | B2 | 7/2016 | Charlot et al. |
| 9,499,812 | B2 | 11/2016 | Krishnan et al. |
| 2001/0045359 | A1 | 11/2001 | Cheng et al. |
| 2002/0036142 | A1 | 3/2002 | Gascoyne et al. |
| 2003/0146100 | A1 | 8/2003 | Huang et al. |
| 2004/0011651 | A1 | 1/2004 | Becker et al. |
| 2004/0052689 | A1 | 3/2004 | Yao |
| 2004/0238052 | A1 | 12/2004 | Karp et al. |
| 2006/0063183 | A1 | 3/2006 | Segawa et al. |
| 2006/0096367 | A1 | 5/2006 | Meyer et al. |
| 2006/0102482 | A1 | 5/2006 | Auerswald et al. |
| 2006/0257993 | A1 | 11/2006 | McDevitt et al. |
| 2006/0289341 | A1 | 12/2006 | Muller et al. |
| 2007/0080062 | A1 | 4/2007 | Harnett et al. |
| 2007/0095669 | A1 | 5/2007 | Lau et al. |
| 2007/0125650 | A1 | 6/2007 | Scurati et al. |
| 2007/0131554 | A1 | 6/2007 | Yu et al. |
| 2007/0152206 | A1 | 7/2007 | Cho et al. |
| 2007/0240495 | A1 | 10/2007 | Hirahara |
| 2007/0284254 | A1 | 12/2007 | Cho et al. |
| 2009/0314644 | A1 | 12/2009 | Golan et al. |
| 2009/0325813 | A1 | 12/2009 | Wang et al. |
| 2010/0155246 | A1 | 6/2010 | Schnelle et al. |
| 2010/0224493 | A1 | 9/2010 | Davalos et al. |
| 2011/0108422 | A1 | 5/2011 | Heller et al. |
| 2011/0139620 | A1 | 6/2011 | Stumber et al. |
| 2012/0048403 | A1 | 3/2012 | Chappel et al. |
| 2012/0270207 | A1 | 10/2012 | Sheehan et al. |
| 2013/0260372 | A1 | 10/2013 | Buermann et al. |
| 2014/0054172 | A1 | 2/2014 | Jonsson et al. |
| 2014/0093871 | A1 | 4/2014 | Shieh et al. |
| 2014/0296089 | A1 | 10/2014 | Holmes et al. |
| 2015/0004077 | A1 | 1/2015 | Wikswo et al. |
| 2015/0219618 | A1 | 8/2015 | Krishnan et al. |
| 2015/0301031 | A1 | 10/2015 | Zin et al. |
| 2016/0175840 | A1 | 6/2016 | Ingber et al. |
| 2016/0271622 | A1 | 9/2016 | Charlot et al. |
| 2016/0327549 | A1 | 11/2016 | Charlot et al. |

FOREIGN PATENT DOCUMENTS

| | | |
|---|---|---|
| CN | 102320559 A | 1/2012 |
| EP | 1775589 A1 | 4/2007 |
| JP | 2001500252 A | 1/2001 |
| JP | 2002502047 A | 1/2002 |
| JP | 2004532968 A | 10/2004 |
| JP | 2008298575 A | 12/2008 |
| WO | WO-9804355 A1 | 2/1998 |
| WO | WO-9938612 A1 | 8/1999 |
| WO | WO-0196025 A2 | 12/2001 |
| WO | WO-2005012872 A2 | 2/2005 |
| WO | WO-2005121767 A1 | 12/2005 |
| WO | WO-2006018981 A1 | 2/2006 |
| WO | WO-2007107910 A1 | 9/2007 |
| WO | WO-2009146143 A2 | 12/2009 |
| WO | WO-2014015187 A1 | 1/2014 |
| WO | WO-2014028222 A1 | 2/2014 |
| WO | WO-2015038797 A1 | 3/2015 |
| WO | WO-2015157217 A1 | 10/2015 |
| WO | WO-2015196141 A1 | 12/2015 |
| WO | WO-2016179308 A1 | 11/2016 |
| WO | WO-2017165852 A1 | 9/2017 |

OTHER PUBLICATIONS

Bettegowda et al. Detection of Circulating Tumor DNA in Early- and Late-Stage Human Malignancies. Sci Transl Med. 6:224 (2014).
Board et al. DNA Methylation in Circulating Tumour DNA as a Biomarker for Cancer. Biomark Insights 2:307-319 (2007).
Board et al. Isolation and extraction of circulating tumor DNA from patients with small cell lung cancer. Ann. N. Y. Acad. Sci. 1137:98-107 (Aug. 2008), Abstract Only.
Cairns. Detection of promoter hypermethylation of tumor suppressor genes in urine from kidney cancer patients. Ann N Y Acad Sci. 1022:40-43 (Jun. 2004).
Casciano et al. Circulating Tumor Nucleic Acids: Perspective in Breast Cancer. Breast Care 5:75-80 (2010).
Catarino et al. Quantification of Free circulating tumor DNA as a diagnostic marker for breast cancer. DNA Cell Biol. 27(8):415-421 (Aug. 2008).
Chan. Circulating EBV DNA as a tumor marker for nasopharyngeal carcinoma. Semin Cancer Biol. 12(6):489-496 (Dec. 2002).
Chan et al. Persistent Aberrations in Circulating DNA Integrity after Radiotherapy Are Associated with Poor Prognosis in Nasopharyngeal Carcinoma Patients. Clinical Cancer Research 14(13):4141-4145 (2008).
Chan et al. Quantitative Analysis of Circulating Methylated DNA as a Biomarker for Hepatocellular Carcinoma. Clinical Chemistry 54(9):1528-1536 (2008).
Chan et al. Radiological, pathological and DNA remission in recurrent metastatic nasopharyngeal carcinoma. BMC Cancer 6:259 (Oct. 31, 2006).
Chang et al. Nasopharyngeal carcinoma. Annals of Oncology 13:1007-1015 (2002).
Cheng et al. Isolation of Cultured Cervical Carcinoma Cells Mixed with Peripheral Blood Cells on a Bioelectronic Chip. Analytical Chemistry 70(11):2321-2326 (1998).
Cheng et al. Preparation and Hybridization Analysis of DNA/A from E. coli on Microfabricated Bioelectronic Chips. Nature Biotechnology 16:541-546 (1998).
Cheng et al. Quantification of circulating cell-free DNA in the plasma of cancer patients during radiation therapy. Cancer Science 100(2):303-309 (Feb. 2009).
Chuang et al. Detectable BRAF mutation n serum DNA samples from patients with papillary thyroid carcinomas. Head Neck 32(2):229-234 (2010).
Chun et al. Circulating tumour-associated plasma DNA represents an independent and informative predictor of prostate cancer. BJU International 98(3):544-548 (2006).
Combaret et al. Circulating MYCN DNA as a Tumor-specific Marker in Neuroblastoma Patients. Cancer Research 62:3646-3648 (Jul. 1, 2002).
Co-pending U.S. Appl. No. 15/293,062, filed Oct. 13, 2016.
Cortese et al. Epigenetic markers of prostate cancer in plasma circulating DNA. Human Molecular Genetics 21:3619-3631 (2012).
Da Silva et al. Circulating cell-free DNA in serum as a biomarker of colorectal cancer. Journal of Clinical Pathology 66(9):775-778 (Sep. 2013).
Daniotti et al. Detection of mutated BRAFV600E variant in circulating DNA of stage III-IV melanoma patients. Int. J. Cancer 120:2439-2444 (Jun. 1, 2007).
Dawson et al. Analysis of Circulating Tumor DNA to Monitor Metastatic Breast Cancer. The New England Journal of Medicine 368(13):1199-1209 (Mar. 28, 2013).
De Maio et al. Circulating and stool nucleic acid analysis for colorectal cancer diagnosis. World Journal of Gastroenterology 20(4):957-967 (Jan. 28, 2014).
Delgado. Characterization of cell-free circulating DNA in plasma in patients with prostate cancer. Tumor Biol. 34(2):983-986 (Apr. 2013).
Deligezer et al. Effect of adjuvant chemotherapy on integrity of free serum DNA in patients with breast cancer. Ann N Y Acad Sci. 1137:175-179 (Aug. 2008).
Devos et al. Circulating Methylated SEPT9 DNA in Plasma Is a Biomarker for Colorectal Cancer. Clinical Chemistry 55(7):1337-1346 (Jul. 2009).
Dobrzycka. Circulating free DNA and p53 antibodies in plasma of patients with ovarian epithelial cancers. Annals of Oncology 22(5):1133-1140 (May 2011).
Dobrzycka. Circulating free DNA, p53 antibody and mutations of KRAS gene in endometrial cancer. 127(3):612-621 (Aug. 1, 2010).

(56) References Cited

OTHER PUBLICATIONS

El Tarhouny et al. Comparison of serum VEGF and its soluble receptor sVEGFR1 with serum cell-free DNA in patients with breast tumor. Cytokine 44(1):65-69 (Oct. 2008).
Ellinger et al. Cell-free circulating DNA: diagnostic value in patients with testicular germ cell cancer. J. Urol. 181(1):363-371 (Jan. 2009).
Ellinger et al. CpG island hypermethylation of cell-free circulating serum DNA in patients with testicular cancer. J. Urol. 182(1):324-329 (Jul. 2009).
Ellinger et al. Noncancerous PTGS2 DNA fragments of apoptotic origin in sera of prostate cancer patients qualify as diagnostic and prognostic indicators. Int. J. Cancer 122(1):138-143 (Jan. 1, 2008).
Elshimali et al. The Clinical Utilization of Circulating Cell Free DNA (CCFDNA) in Blood of Cancer Patients. Int. J. Mol. Sci. 14(9):18925-18958 (Sep. 13, 2013).
Fuhr et al. Cell manipulation and cultivation under a.c. electric field influence in highly conductive culture media. Biochimica et Biophysica Acta 1201:353-360 (1994).
Gahan et al. Circulating nucleic acids in plasma and serum: diagnosis and prognosis in cancer. EPMA Journal 1(3):503-512 (Sep. 2010).
Ganepola et al. Use of blood-based biomarkers for early diagnosis and surveillance of colorectal cancer. World Journal of Gastrointestinal Oncology 6(4):83-97 (Apr. 15, 2014).
Gautschi et al. Circulating deoxyribonucleic Acid as prognostic marker in non-small-cell lung cancer patients undergoing chemotherapy. J Clin Oncol. 22(20):4157-4164 (2004).
Goessl et al. DNA Alterations in Body Fluids as Molecular Tumor Markers for Urological Malignancies. European Urology 41(6):668-676 (Jun. 2002).
Goodard et al. Handbook of Nanoscience. 2nd edition.Ch 16, p. 5-8 (2007).
Gornik et al. Free serum DNA is an early predictor of severity of acute pancreatitis. Clin Biochem. 42(1-2):38-43 (Jan. 2009).
Green et al. Ac electrokinetics: a survey of sub-micrometre paricle dynamics. J. Phys. D: Appl. Phys. 33:632-641 (2000).
Guan et al. Analysis of circulating DNA level in the plasma of cervical cancer patients. Nan fang Yi Ke Da Xue Xue Bao 28(9):1663-1667 (Aug. 2008) (English Abstract).
Haeberle et al. Centrifugal extraction of plasma from whole blood on a rotating disk. Lab Chip 6(6):776-781 (2006).
Hashad et al. Free circulating tumor DNA as a diagnostic marker for breast cancer. J Clin Lab Anal. 26(6):467-472 (Nov. 2012).
Higgins et al. Variant Ciz1 is a circulating biomarker for early-stage lung cancer. PNAS USA 109(45):E3128-3135 (Nov. 6, 2012).
Higuchi. Chromosomal DNA fragmentation inapoptosis and necrosis induced by oxidative stress. Biochem Pharacol. 66:1527-1535(2003).
Higuchi et al. Appearance of 1-2 Mbp giant DNA fragments as an early common response leading to cell death induced by various substances that cause oxidative stress. Free Radical Biology & Medicine 23:90-99 (1997).
Hoffmann et al. Methylated DAPK and APC promoter DNA detection in peripheral blood is significantly associated with apparent residual tumor and outcome. J Cancer Res Clin Oncol. 135(89):1231-1237 (Sep. 2009).
Hoffmann et al. Universal protocol for grafting PCR primers onto various lab-on-a-chip substrates for solid-phase PCR. RSC Advances 2:3885-3889 (2012).
Hohaus et al. Cell-free circulating DNA in Hodgkin's and non-Hodgkin's lymphomas. Annals of Oncology 20(8):1408-1413 (2009).
Holdhoff et al. Blood-based biomarkers for malignant gliomas. J Neurooncol 113:345-352 (2013).
Holzel et al. Trapping Single Molecules by Dielectrophoresis. Phys. Rev. Lett. 95:128102 (2005).
Hosny et al. Ser-249 TP53 and CTNNB1 mutations in circulating free DNA of Egyptian patients with hepatocellular carcinoma versus chronic liver diseases. Cancer Lett. 264(2):201-208 (Jun. 18, 2008).

Huang et al. Dielectrophoretic Cell Separation and Gene Expression Profiling on Microelectronic Chip Arrays. Analytical Chem. 74:3362-3371 (2002).
Huang et al. Electric Manipulation of Bioparticles and Macromolecules on Microfabricated Electrodes. Analytical Chemistry (73):1549-1559 (2001).
Huang et al. Functionalization of Surfaces by Water-Accelerated Atom-Transfer Radical Polymerization of Hydroxyethyl Methacrylate and Subsequent Derivatization. Macromolecules 35:1175-1179 (2002).
Hughes et al. Dielectrophoretic Characterization and Separation of Antibody-Coated Submicrometer Latex Spheres. Anal Chem 71:3441-3445(1999).
Hughes et al. Dielectrophoretic Manipulation and Characterization of Herpes Simplex Virus-1 Capsids. Eur Biophys J 30:268-272 (2001).
Hughes. Nanoparticle Manipulation by Electrostatic Forces. Handbook of Nanoscience, Engineering and Technology 2nd Ed., WA Goddard III, DW Brenner, S. Lyshenski & G. Iafrate (eds.) (CRC Press 2007), pp. 16-1 to 16-32.
Hughes. Strategies for Dielectrophoretic Separation in Laboratory-on-a-chip Systems. Electrophoresis 23:2569-2582 (2002).
Iida et al. Relation between serum levels of cell-free DNA and inflammation status in hepatitis C virus-related hepatocellular carcinoma. Oncology Reports 20(4):761-765 (Oct. 2008).
Iizuka et al. Elevated Levels of Circulating Cell-free DNA in the Blood of Patients with Hepatitis C Virus-associated Hepatocellular Carcinoma. Anticancer Research 26(6C):4713-4720 (2006).
Jiang et al. Dynamic monitoring of plasma circulating DNA in patients with acute myeloid leukemia and its clinical significance. Zhingguo Shi Yan Xue Ye Xue Za Zhi 20(1):53-56 (Feb. 2012) (Abstract).
Jiang et al. Increased plasma DNA integrity index in head and neck cancer patients. Int. J. Cancer 119(11):2673-2676 (Dec. 2006).
Jin et al. Circulating DNA-Important Biomarker of Cancer. Journal of Molecular Biomarkers & Diagnosis S2 (2012) (7 pgs.).
Kakimoto et al. Microsatellite analysis of serum DNA in patients with oral squamous cell carcinoma. Oncology Reports 20(5):1195-1200 (Nov. 2008).
Kolesnikova et al. Circulating DNA in the blood of gastric cancer patients. Ann N Y Acad Sci. 1137:226-231 (Aug. 2008).
Krishnan et al. Alternating current electrokinetic separation and detection of DNA nanoparticles in high-conductance solutions. Electrophoresis 29(9):1765-1774 (2008).
Krishnan et al. An AC electrokinetic method for enhanced detection of DNA nanoparticles. J. Biophotonics 2(4):253-261 (2009).
Krishnan et al. Interaction of nanoparticles at the DEP microelectrode interface under high conductance conditions. Electrochem. Comm. 11(8):1661-1666 (2009).
Kuhlmann et al. LOH at 6q and 10q in fractionated circulating DNA of ovarian cancer patients is predictive for tumor cell spread and overall survival. BMC Cancer 12:325 (Jul. 31, 2012).
Lavon et al. Serum DNA can define tumor-specific genetic and epigenetic markers in gliomas of various grades. Neuro-Oncology 12(2):173-180 (2010).
Lee et al. Methylation of TMEFF2 Gene in Tissue and Serum DNA from Patients with Non-Small Cell Lung Cancer. Molecules and Cells 34(2):171-176 (Aug. 31, 2012).
Liggett et al. Differential Methylation of Cell-Free Circulating DNA Among Patients With Pancreatic Cancer Versus Chronic Pancreatitis. Cancer 116(7):1674-1680 (Apr. 1, 2010).
Liggett et al. Methylation patterns in cell-free plasma DNA reflect removal of the primary tumor and drug treatment of breast cancer patients. Int. J. Cancer 128(2):492-499 (Jan. 15, 2011).
Lo Nigro et al. Methylated Tissue Factor Pathway Inhibitor 2 (TFPI2) DNA in Serum Is a Biomarker of Metastatic Melanoma. Journal of Investigative Dermatology 133(5):1278-1285 (May 2013).
Lofton-Day et al. DNA Methylation Biomarkers for Blood-Based Colorectal Cancer Screening. Clinical Chemistry 54(2):414-423 (Feb. 2008).

(56) References Cited

OTHER PUBLICATIONS

Ma et al. Detection of circulating hypermethylated tumor-specific RASSF1A DNA in ovarian cancer patients. Zhonghua Bing Li Xue Za Zhi. 34(12):785-787 (Dec. 2005) (Abstract).
Ma et al. Methylated DNA and microRNA in Body Fluids as Biomarkers for Cancer Detection. International Journal of Molecular Sciences 14(5):10307-10331 (May 16, 2013).
Majchrzak et al. Detection of MGMT, RASSF1A, p15INK4B, and p14ARF promoter methylation in circulating tumor-derived DNA of central nervous system cancer patients. J. Appl. Genetics 54:335-344 (2013).
Melnikov et al. Methylation profile of circulating plasma DNA in patients with pancreatic cancer. J Surg Oncol. 99(2):119-122 (Feb. 2009).
Menachery et al. Controlling cell destruction using dielectrophoretic forces. IEE Proc.—Nanobiotechnol. 152(4):145-149 (2005).
Mirza et al. Clinical significance of promoter hypermethylation of ERβ and RARβ2 in tumor and serum DNA in Indian breast cancer patients. Ann Surg Oncol. 19(9):3107-1315 (Sep. 2012).
Misale et al. Emergence of KRAS mutations and acquired resistance to anti EGFR therapy in colorectal cancer. Nature 486(7404):532-536 (Jun. 28, 2012).
Misawa et al. RASSF1A hypermethylation in pretreatment serum DNA of neuroblastoma patients: a prognostic marker. British Journal of Cancer 100:399-404 (2009).
Morgan et al. Separation of Sub micron Bioparticles by Dielectrophoresis Biophysical Journal. 77:516-525 (1999).
Mouliere et al. Circulating Cell-Free DNA from Colorectal Cancer Patients May Reveal High KRAS or BRAF Mutation Load. Translational Oncology 6(3):319-328 (Jun. 2013).
Muller et al. DNA Methylation in Serum of Breast Cancer Patients: An Independent Prognostic Marker. Cancer Research 63(22):7641-7645 (Nov. 15, 2003).
Muller et al. Identification of Loss of Heterozygosity on Circulating Free DNA in Peripheral Blood of Prostate Cancer Patients: Potential and Technical Improvements. Clinical Chemistry 54(4):688-696 (Apr. 2008).
Nakagawa et al. Fabrication of amino Silane-Coated Microchip for DNA extraction from Whole Blood. Journal of Biotechnology 116(2):105-111 (2005).
Nakamoto et al. Detection of Microsatellite Alterations in Plasma DNA of Malignant Mucosal Melanoma Using Whole Genome Amplification. Bull Tokyo Dent. Coll. 49(2):77-87 (May 2008).
Nakamura et al. Application of a Highly Sensitive Detection System for Epidermal Growth Factor Receptor Mutations in Plasma DNA. Journal of Thoracic Oncology 7(9):1369-1381 (Sep. 2012).
Nakayama et al. A Highly Sensitive Method for the Detection of p16 Methylation in the Serum of Colorectal Cancer Patients. Anticancer Research 27(36)1459-1464 (2007).
Page et al. Detection of HER2 amplification in circulating free DNA in patients with breast cancer. British Journal of Cancer 104:1342-1348 (2011).
Pang et al. Microsatellite alterations of circulating DNA in the plasma of patients with hepatocellular carcinoma. Zhonghua Yi Xue Za Zhi. 86(24):1662-1665 (Jun. 27, 2006) (Abstract).
Papadopoulou et al. Cell-free DNA and RNA in Plasma as a New Molecular Marker for Prostate and Breast Cancer, Ann. NY, Acad. Sci. 1075:235-243 (2006).
Parker et al. mRNA: detection by in Situ and northern hybridization. Methods Mol Biol 106:247-283 (1999).
PCT/US2009/039565 International Preliminary Report on Patentability and Written Opinion dated Oct. 5, 2010.
PCT/US2009/039565 International Search Report dated Dec. 23, 2009.
PCT/US2013/036845 International Preliminary Report on Patentability and Written Opinion dated Oct. 30, 2014.
PCT/US2013/036845 International Search Report and Written Opinion dated Aug. 6, 2013.
PCT/US2013/051158 International Preliminary Report on Patentability dated Jan. 20, 2015.
PCT/US2013/051158 International Search Report and Written Opinion dated Nov. 14, 2013.
PCT/US2015/024624 International Preliminary Report on Patentability dated Oct. 12, 2016.
PCT/US2015/024624 International Search Report and Written Opinion dated Aug. 21, 2015.
PCT/US2015/036789 International Preliminary Report on Patentability dated Dec. 20, 2016.
PCT/US2015/036789 International Search Report and Written Opinion dated Sep. 29, 2015.
PCT/US2016/030821 International Search Report and Written Opinion dated Aug. 29, 2016.
Pethig. Dielectrophoresis: Using Inhomogenous AC Electrical Fields to Separate and Manipulate Cells, CRC Critical Reviews in Biotechnology, CRC Press, Boca Raton, FL, US. 16(4):331-348 (Jan. 1, 1996).
Ponomaryova et al. Potentialities of aberrantly methylated circulating DNA for diagnostics and post-treatment follow-up of lung cancer patients. Lung Cancer. 81(3):397-403 (Sep. 2013).
Ramos et al. Ac electrokinetics: a review of forces in microelectrode structures. J Phys. D: Appl. Phys. 31:2338-2353 (1998).
Ren et al. Circulating DNA level is negatively associated with the long-term survival of hepatocellular carcinoma patients. World Journal of Gastroenterology 12(24):3911-3914 (Jun. 28, 2006).
Sai et al. Quantification of Plasma Cell-free DNA in Patients with Gastric Cancer. Anticancer Research 27(4C):2747-2752 (2007).
Sakakura et al. Quantitative Analysis of Tumor-derived Methylated RUNX3 Sequences in the Serum of Gastric Cancer Patients. Anticancer Research 29:2619-2626 (2009).
Salkeni et al. Detection of EGFRvIII mutant DNA in the peripheral blood of brain tumor patients. J. Neurooncol. 115(1):27-35 (Oct. 2013).
Sawabu et al. Serum tumor markers and molecular biological diagnosis in pancreatic cancer. Pancreas 28(3):263-267 (Apr. 2004).
Schwarzenbach. Detection and monitoring of cell-free DNA in blood of patients with colorectal cancer. Ann N Y Acad Sci. 1137:190-196 (Aug. 2008).
Schwarzenbach. Loss of Heterozygosity at Tumor Suppressor Genes Detectable on Fractionated Circulating Cell-Free Tumor DNA as Indicator of Breast Cancer Progression. Clinical Cancer Research 18:5719-5730 (Sep. 25, 2012).
Sharma et al. DNA methylation of circulating DNA: a marker for monitoring efficacy of neoadjuvant chemotherapy in breast cancer patients. Tumour Biol. 33(6):1837-1843 (Dec. 2012).
Shaw et al. Genomic analysis of circulating cell-free DNA infers breast cancer dormancy. Genome Research 22(2):220-231 (Feb. 2012).
Sonnenberg et al. Dielectrophoretic Isolation of DNA and Nonoparticles from Blood. Electrophoresis 33(16):2482-2490 (2012).
Sorenson. Detection of Mutated KRAS2 Sequences as Tumor Markers in Plasma/Serum of Patients with Gastrointestinal Cancer. Clin Cancer Res 6:2129-2137 (2000).
Sosnowski et al. Rapid determination of single base mismatch mutations in DNA hybrids by direct electric field control. PNAS USA 94:1119-1123 (Feb. 1997).
Stephens et al. The dielectrophoresis enrichment of CD34+ cells from peripheral blood stern cell harvests. Bone Marrow Transplant. 18:777-782 (1996).
Stroun et al. Isolation and characterization of DNA from the plasma of cancer patients. Eur J Cancer Clin Oneol 23:707-712 (1987).
Swanson. A fully multiplexed CMOS biochip for analysis. Sensors and Actuators B 64:22-30 (Jun. 2000).
Tamkovich et al. Cell-surface-bound circulating DNA as a prognostic factor in lung cancer. Ann N Y Acad Sci. 1137:214-217 (Aug. 2008).
Tanaka et al. Role of circulating free alu DNA in endometrial cancer. Int J Gynecol Cancer 22(1):82-86 (Jan. 2012).
Tangkijvanich et al. Serum LINE-1 hypomethylation as a potential prognostic marker for hepatocellular carcinoma. Clin Chim Acta. 379(1-2):127-133 (Apr. 2007).

(56) References Cited

OTHER PUBLICATIONS

Tani et al. An early detection of recurrence using reverse transcriptase-polymerase chain reaction (RT-PCP) and methylation-specific plymerase chain reaction (MSP) from peripheral blood in patients after gastrectomy. Gan to Kagaku Ryoho 33(12):1720-1722 (Nov. 2006) (Abstract).
Tomita et al. Quantification of Circulating Plasma DNA Fragments as Tumor Markers in Patients with Esophageal Cancer, Anticancer Research 27(4C):2737-2742 (2007).
Toner et al. Blood-on-a-chip. Annual Review of Biomedical Engineering 7:77-103 (2005).
Tong et al. Diagnostic developments involving cell-free (circulating) nucleic acids. Clinica Chimica Acta. 363:187-96 (2006).
Toth et al. Free circulating DNA based colorectal cancer screening from peripheral blood: the possibility of the methylated septin 9 gene marker. Orv. Hetil. 150(21):969-977(May 24, 2009) (English Abstract).
Trevisiol et al. Prognostic value of circulating KRAS2 gene mutations in colorectal cancer with distant metastases. Int J Biol Markers. 21(4):223-228 (Oct.-Dec. 2006).
Tuukanen et al. Carbon nanotubes as electrodes for dielectrophoresis of DNA. Nano Letters. 6:1339-1343 (2006).
Umetani et al. Increased Integrity of Free Circulating DNA in Sera of Patients with Colorectal or Periampullary Cancer: Direct Quantitative PCR for ALU Repeats. Clinical Chemistry 52(6):1062-1069 (Jun. 2006).
Umetani et al. Prediction of Breast Tumor Progression by Integrity of Free Circulating DNA in Serum. Journal of Clinical Oncology 24(26):4270-4276 (Sep. 10, 2006).
U.S. Appl. No. 12/936,147 Office Action dated Apr. 27, 2015.
U.S. Appl. No. 12/936,147 Office Action dated Aug. 12, 2015.
U.S. Appl. No. 12/936,147 Office Action dated Dec. 11, 2012.
U.S. Appl. No. 12/936,147 Office Action dated Jul. 18, 2013.
U.S. Appl. No. 12/936,147 Office Action dated Oct. 31, 2012.
U.S. Appl. No. 12/936,147 Office Action dated Sep. 22, 2016.
U.S. Appl. No. 13/864,179 Office Action dated Aug. 15, 2013.
U.S. Appl. No. 14/063,884 Office Action dated Aug. 28, 2014.
U.S. Appl. No. 14/063,884 Office Action dated Feb. 12, 2014.
U.S. Appl. No. 14/067,841 Office Action dated Mar. 16, 2015.
U.S. Appl. No. 14/194,566 Office Action dated May 15, 2014.
U.S. Appl. No. 14/201,715 Office Action dated May 15, 2014.
U.S. Appl. No. 14/201,726 Office Action dated May 16, 2014.
U.S. Appl. No. 14/271,337 Office Action dated Jun. 12, 2014.
U.S. Appl. No. 14/311,037 Office Action dated Sep. 5, 2014.
U.S. Appl. No. 14/415,546 Office Action dated Apr. 28, 2016.
U.S. Appl. No. 14/415,546 Office Action dated Oct. 7, 2016.
U.S. Appl. No. 14/477,800 Office Action dated Dec. 15, 2014.
U.S. Appl. No. 14/477,800 Office Action dated Feb. 2, 2015.
U.S. Appl. No. 14/509,022 Office Action dated Jan. 15, 2015.
U.S. Appl. No. 14/512,356 Office Action dated Feb. 5, 2015.
U.S. Appl. No. 14/680,819 Office Action dated Dec. 3, 2015.
U.S. Appl. No. 14/925,157 Office Action dated Mar. 22, 2016.
U.S. Appl. No. 15/171,876 Office Action dated Oct. 12, 2016.
U.S. Appl. No. 60/804,818, filed Jun. 14, 2006.
Wallner et al. Methylation of Serum DNA Is an Independent Prognostric Marker in Colorectal Cancer. Clinical Cancer Research 12(24):7347-7352 (Dec. 15, 2006).
Washizu et al. Applications of electrostatic stretch-and-positioning of DNA. Industry Applications. IEEE Transactions on Industry Applications 31:447-456 (1995).
Washizu et al. Electrostatic manipulation of DNA in microfabricated structures. Industry Applications. IEEE Transactions on Industry Applications 26:1165-1172 (1990).
Weaver et al. Methylated tumor-specific DNA as a plasma biomarker in patients with glioma. Cancer Invest. 24(1):35-40 (Feb. 2006).
Weiss et al. Circulating tumor DNA to monitor metastatic breast cancer. New England Journal of Medicine. 369(1):93 (Jul. 4, 2013).
Widschwendter et al. CDH1 and CDH13 Methylation in Serum is an Independent Prognostic Marker in Cervical Cancer Patients. Int. J. Cancer 109(2):163-166 (Mar. 20, 2004).
Wu et al. Cell-free DNA: measurement in various carcinomas and establishment of normal reference range. Clin Chim Acta. 321(1-2):77-87 (2002).
Xie et al. Quantification of plasma DNA as a screening tool for lung cancer. Chinese Medical Journal 117(10)1 485-1488 (Oct. 2004).
Yoon et al. Comparison of Circulating Plasma DNA Levels between Lung Cancer Patients and Healthy Controls. Journal of Molecular Diagnostics 11(3):182-185 (May 2009).
Zachariah et al. Circulating cell-free DNA as a potential biomarker for minimal and mild endometriosis. Reprod Biomed Online 18(3):407-411 (Mar. 2009).
Zachariah et al. Levels of circulating cell-free nuclear and mitochondrial DNA in benign and malignant ovarian tumors. Obstet. Gynecol. 112(4):843-850 (Oct. 2008).
Zhou et al. Circulating cell-free nucleic acids: promising biomarkers of hepatocellular carcinoma. Semin Oncol. 39(4):440-448 (Aug. 2012).
Ziegler et al. Circulating DNA: a new diagnostic gold mine? Cancer Treat Rev. 28:255-271 (2002).
Zurita et al. Hypermethylated 14-3-3-σ and ESR1 gene promoters in serum as candidate biomarkers for the diagnosis and treatment efficacy of breast cancer metastasis. BMC Cancer 10(217):9 pgs. (May 2010).
PCT/US2016/030821 International Preliminary Report on Patentability dated Nov. 16, 2017.
Sonnenberg et al. Dielectrophoretic isolation and detection of cfc-DNA nanoparticulate biomarkers and virus from blood. Electrophoresis 34(7):1076-1084 (2013).
U.S. Appl. No. 15/469,406 Office Action dated Mar. 28, 2018.

| Sample Description | Raw Reads | Mapping Percentage (E. coli) | Fraction of E. coli Genome Covered (1x) | Fraction of E. coli Genome Covered (10x) | Fraction of E. coli Genome Covered (30x) | Fraction of E. coli Genome Covered (50x) |
|---|---|---|---|---|---|---|
| E. Coli DNA on Chip, first wash | 15,921,285 | 51.41% | 97.84% | 97.63% | 97.04% | 93.45% |
| E. Coli DNA on Chip, second wash | 25,880,716 | 71.36% | 97.83% | 97.68% | 97.46% | 97.33% |
| E. Coli DNA in tube | 14,466,090 | 61.84% | 97.84% | 97.67% | 97.28% | 95.54% |

NUCLEIC ACID SAMPLE PREPARATION

CROSS-REFERENCE

This application is a U.S. National Stage Entry of PCT/US2015/036789, filed Jun. 19, 2015; which is a continuation of U.S. application Ser. No. 14/311,037, filed Jun. 20, 2014, now U.S. Pat. No. 8,932,815, granted Jan. 13, 2015; which is a continuation-in-part of U.S. application Ser. No. 14/067,841, filed Oct. 30, 2013, now U.S. Pat. No. 9,206,416, granted Dec. 8, 2015; which is a continuation of U.S. application Ser. No. 13/864,179, filed Apr. 16, 2013, now U.S. Pat. No. 8,603,791, granted Dec. 10, 2013; which claims the benefit of priority from 61/624,897, filed Apr. 16, 2012, which are all incorporated herein by reference in their entirety.

BACKGROUND OF THE INVENTION

Exponentially rapid progress has been made in the field of DNA sequencing in recent years. Methods such as pyrosequencing, ion semiconductor sequencing and polony sequencing aim to reduce costs to a point where sequencing a complete genome becomes routine. This is expected to transform fields as diverse as medicine, renewable energy, biosecurity and agriculture to name a few. However, techniques for isolating DNA suitable for sequencing have not kept pace and there is a threat that this will become a limitation.

SUMMARY OF THE INVENTION

In some instances, the present invention fulfills a need for improved methods of nucleic acid isolation from biological samples. Particular attributes of certain aspects provided herein include a total sample preparation time of less than about one hour, with hands-on time of less than about one minute. In some embodiments, the present invention can be used to isolate DNA from dilute and/or complex fluids such as blood or environmental samples. In other aspects, the present invention can use small amounts of starting material, achieve highly purified nucleic acids, and is amenable to multiplexed and high-throughput operation.

Disclosed herein are methods and devices for quantifying nucleic acid in a sample, comprising: a. applying a sample with a conductivity of greater than 100 mS/m to a device, the device comprising an array of electrodes capable of establishing an AC electrokinetic field region, the device further comprising at least two chambers, the sample applied to a first chamber; b. applying known quantities of a nucleic acid standard to a second chamber; c. establishing a first AC electrokinetic high field region in the first chamber, the first AC electrokinetic high field capable of isolating larger nanoparticulate molecular targets; d. establishing a second AC electrokinetic low field in the first chamber, the second AC electrokinetic low field capable of concentrating cells or micron-sized entities that may be present in the sample; e. establishing a third AC electrokinetic high field to the second chamber, the second AC electrokinetic high field isolating the molecular nucleic acid standard applied to the second chamber; f. flushing cells and micron-sized entities that may be present in the sample from the first chamber; g. detecting bound nucleic acid signal on the array in the first chamber and second chamber; and h. quantifying the bound nucleic acid by comparing the detected signal from the first chamber to detected signal from the second chamber.

In some embodiments, the larger nanoparticulate molecular target is chosen from the group consisting of exosomes, high mw nucleic acids, including high mw DNA, oligonucleosome complexes, aggregated proteins, vesicle bound DNA, cell membrane fragments and cellular debris. In other embodiments, the target circulating cell-free biomarker is chosen from the group consisting of mutations, deletions, rearrangements or methylated nucleic acid of circulating DNA, micro RNA, RNA from microvesicles or a combination thereof. In still other embodiments, the detection of the cell-free biomarker provides information useful for cancer diagnosis, cancer prognosis or treatment response in a patient. In yet other embodiments, the tumor cell-free biomarker is associated with CNS tumors, neuroblastoma, gliomas, breast cancer, endometrial tumors, cervical tumors, ovarian tumors, hepatocellular carcinoma, pancreatic carcinoma, esophageal tumors, Stoch tumors, colorectal tumors, head and neck tumors, nasopharyngeal carcinoma, thyroid tumors, lymphoma, leukemia, lung cancer, non-small cell lung carcinoma, small cell lung carcinoma, testicular tumors, kidney tumors, prostate carcinoma, skin cancer, malignant melanoma, squamous cell carcinoma or a combination thereof. In some embodiments, the tumor cell-free biomarker is GFAP, VEGF, EGFR, b-FGF, KRAS, YKL-40, MMP-9 or combinations thereof.

In other embodiments, the target biomarker is chosen from the group consisting of proteins, lipids, antibodies, high molecular weight DNA, tumor cells, exosomes, nucleosomes and nanosomes. In still other embodiments, the bound nucleic acid is eluted from the first chamber for further characterization. In yet other embodiments, the eluted nucleic acid is amplified or sequenced. In still other embodiments, the sample is whole blood, serum, plasma, cerebrospinal fluid, body tissue, urine or saliva.

In some embodiments, the AC electrokinetic field is produced using an alternating current having a voltage of 1 volt to 40 volts peak-peak, and/or a frequency of 5 Hz to 5,000,000 Hz and duty cycles from 5% to 50%. In other embodiments, the conductivity of the sample is greater than 500 mS/m. In yet other embodiments, the array of electrodes is spin-coated with a hydrogel having a thickness between about 0.1 microns and 1 micron. In still other embodiments, the hydrogel comprises two or more layers of a synthetic polymer. In some embodiments, the hydrogel has a viscosity between about 0.5 cP to about 5 cP prior to spin-coating. In other embodiments, the hydrogel has a conductivity between about 0.1 S/m to about 1.0 S/m. In yet other embodiments, the isolated nucleic acid comprises less than about 10% non-nucleic acid cellular material or cellular protein by mass.

In some embodiments, the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant. In still other embodiments, the array of electrodes comprises a passivation layer with a relative electrical permittivity from about 2.0 to about 4.0.

Disclosed herein are methods and devices for analyzing a nucleic acid in a sample comprising: a. applying a sample with a conductivity of greater than 100 mS/m to a device, the device comprising an array of electrodes capable of establishing an AC electrokinetic field region, the device further comprising at least two chambers, the sample applied to a first chamber; b. applying known quantities of a nucleic acid standard to a second chamber; c. establishing a first AC electrokinetic high field region in the first chamber, the first AC electrokinetic high field capable of isolating larger nanoparticulate molecular targets; d. establishing a second AC electrokinetic low field in the first chamber, the second AC electrokinetic low field capable of concentrating cells or micron-sized entities that may be present in the sample; e. establishing a third AC electrokinetic high field to the second chamber, the second AC electrokinetic high field isolating the molecular nucleic acid standard applied to the second chamber; f. flushing cells and micron-sized entities that may be present in the sample from the first chamber; g. detecting bound nucleic acid signal on the array in the first chamber and second chamber; h. eluting the bound nucleic acid from the first chamber; and i. performing sequencing and/or polymerase chain reaction analysis on the eluted nucleic acid.

Also disclosed herein, in some embodiments, is a method for isolating a nucleic acid from a fluid comprising cells, the method comprising: a. applying the fluid to a device, the device comprising an array of electrodes capable of establishing an AC electrokinetic field region; b. concentrating a plurality of cells in a first AC electrokinetic field region, wherein the first AC eletrokinetic field region is a first dielectrophoretic high field region and the conductivity of the fluid is less than 500 mS/m; c. lysing the cells on the array; and d. isolating nucleic acid in a second AC electrokinetic field region, wherein the second AC electrokinetic field is a second dielectrophoretic high field region. In some embodiments, the AC electrokinetic field is produced using an alternating current having a voltage of 1 volt to 40 volts peak-peak, and/or a frequency of 5 Hz to 5,000,000 Hz and duty cycles from 5% to 50%. In some embodiments, the conductivity of the fluid is less than 300 mS/m. In some embodiments, the electrodes are selectively energized to provide the first dielectrophoretic high field region and subsequently or continuously selectively energized to provide the second dielectrophoretic high field region. In some embodiments, the cells are lysed using a direct current, a chemical lysing agent, an enzymatic lysing agent, heat, pressure, sonic energy, or a combination thereof. In some embodiments, the method further comprises degradation of residual proteins after cell lysis. In some embodiments, the cells are lysed using a direct current with a voltage of 1-500 volts, a pulse frequency of 0.2 to 200 Hz with duty cycles from 10-50%, and a pulse duration of 0.01 to 10 seconds applied at least once. In some embodiments, the array of electrodes is spin-coated with a hydrogel having a thickness between about 0.1 microns and 1 micron. In some embodiments, the hydrogel comprises two or more layers of a synthetic polymer. In some embodiments, the hydrogel has a viscosity between about 0.5 cP to about 5 cP prior to spin-coating. In some embodiments, the hydrogel has a conductivity between about 0.1 S/m to about 1.0 S/m. In some embodiments, the isolated nucleic acid comprises less than about 10% non-nucleic acid cellular material or cellular protein by mass. In some embodiments, the method is completed in less than 10 minutes. In some embodiments, the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0.

In some embodiments, disclosed herein is a method for isolating a nucleic acid from a fluid comprising cells, the method comprising: a. applying the fluid to a device, the device comprising an array of electrodes capable of establishing an AC electrokinetic field region; b. concentrating a plurality of cells in a first AC electrokinetic field region, wherein the first AC electrokinetic field region is a first dielectrophoretic low field region and the conductivity of the fluid is greater than 300 mS/m; c. isolating nucleic acid in a second AC electrokinetic field region, wherein the second AC electrokinetic field is a second electrophoretic high field region; and d. flushing cells away from the array. In some embodiments, the AC electrokinetic field is produced using an alternating current having a voltage of 1 volt to 40 volts peak-peak, and/or a frequency of 5 Hz to 5,000,000 Hz and duty cycles from 5% to 50%. In some embodiments, the conductivity of the fluid is greater than 500 mS/m. In some embodiments, the electrodes are selectively energized to provide the first dielectrophoretic high field region and subsequently or continuously selectively energized to provide the second dielectrophoretic high field region. In some embodiments, the method further comprises degrading residual proteins on the array. In some embodiments, the residual proteins are degraded by one or more of a chemical degradant or an enzymatic degradant. In some embodiments, the residual proteins are degraded by Proteinase K. In some embodiments, the array of electrodes is spin-coated with a hydrogel having a thickness between about 0.1 microns and 1 micron. In some embodiments, the hydrogel comprises two or more layers of a synthetic polymer. In some embodiments, the hydrogel has a viscosity between about 0.5 cP to about 5 cP prior to spin-coating. In some embodiments, the hydrogel has a conductivity between about 0.1 S/m to about 1.0 S/m. In some embodiments, the isolated nucleic acid comprises less than about 10% non-nucleic acid cellular material or cellular protein by mass. In some embodiments, the method is completed in less than 10 minutes. In some embodiments, the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0.

Disclosed herein, in some embodiments, is a method for isolating a nucleic acid from a fluid comprising cells, the method comprising: a. applying the fluid to a device, the device comprising an array of electrodes capable of generating an AC electrokinetic field; b. concentrating a plurality of cells in a first AC electrokinetic field region; c. lysing the cells in the first AC electrokinetic field region; and d. isolating the nucleic acid in a second AC electrokinetic field region, wherein the fluid is at a conductivity capable of concentrating a plurality of cells in the first AC electrokinetic field region. In some embodiments, the first AC electrokinetic region is a dielectrophoretic field region, wherein the second AC electrokinetic field region is a dielectrophoretic field region, or a combination thereof. In some embodiments, the first AC electrokinetic field region is a first dielectrophoretic low field region and the second AC electrokinetic field region is a second dielectrophoretic high field region, wherein the conductivity of the fluid is greater than 300 mS/m. In some embodiments, the first AC electrokinetic field region is a first dielectrophoretic high field region and the second AC electrokinetic field region is a second dielectrophoretic high field region, wherein the conductivity of the fluid is less than 300 mS/m. In some embodiments, the nucleic acid is concentrated in the second AC electrokinetic field region. In some embodiments, the method further comprises flushing residual material from the array and the isolated nucleic acid. In some embodiments, the method further comprises degradation of a residual protein. In some embodiments, the method further comprises flushing degraded proteins from the array and the isolated nucleic acid. In some embodiments, the method further comprises collecting the nucleic acid. In some embodiments, the first AC electrokinetic field region is produced by an alternating current. In some embodiments, the first AC electrokinetic field region is produced using an alternating current having a voltage of 1 volt to 40 volts peak-peak; and/or a frequency of 5 Hz to 5,000,000 Hz, and duty cycles from 5% to 50%. In some embodiments, the second AC electrokinetic field region is a different region of the electrode array as the first AC electrokinetic field region. In some embodiments, the second AC electrokinetic field region is the same region of the electrode array as the first AC electrokinetic field region. In some embodiments, the second AC electrokinetic field region is produced by an alternating current. In some embodiments, the second AC electrokinetic field region is produced using an alternating current having a voltage of 1 volt to 50 volts peak-peak; and/or a frequency of 5 Hz to 5,000,000 Hz, and duty cycles from 5% to 50%. In some embodiments, the electrodes are selectively energized to provide the first AC electrokinetic field region and subsequently or continuously selectively energized to provide the second AC electrokinetic field region. In some embodiments, the cells are lysed by applying a direct current to the cells. In some embodiments, the direct current used to lyse the cells has a voltage of 1-500 volts; and a duration of 0.01 to 10 seconds applied once or as multiple pulses. In some embodiments, the direct current used to lyse the cells is a direct current pulse or a plurality of direct current pulses applied at a frequency suitable for lysing the cells. In some embodiments, the pulse has a frequency of 0.2 to 200 Hz with duty cycles from 10-50%. In some embodiments, the cells are lysed on the device using a direct current, a chemical lysing agent, an enzymatic lysing agent, heat, osmotic pressure, sonic energy, or a combination thereof. In some embodiments, the residual material comprises lysed cellular material. In some embodiments, the lysed cellular material comprises residual protein freed from the plurality of cells upon lysis. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the method further comprises amplifying the isolated nucleic acid by polymerase chain reaction. In some embodiments, the nucleic acid comprises DNA, RNA, or any combination thereof. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass. In some embodiments, the method is completed in less than about one hour. In some embodiments, centrifugation is not used. In some embodiments, the residual proteins are degraded by one or more of chemical degradation and enzymatic degradation. In some embodiments, the residual proteins are degraded by Proteinase K. In some embodiments, the residual proteins are degraded by an enzyme, the method further comprising inactivating the enzyme following degradation of the proteins. In some embodiments, the enzyme is inactivated by heat (e.g., 50 to 95° C. for 5-15 minutes). In some embodiments, the residual material and the degraded proteins are flushed in separate or concurrent steps. In some embodiments, the isolated nucleic acid is collected by (i) turning off the second AC electrokinetic field region; and (ii) eluting the nucleic acid from the array in an eluant. In some embodiments, nucleic acid is isolated in a form suitable for sequencing. In some embodiments, the nucleic acid is isolated in a fragmented form suitable for shotgun-sequencing. In some embodiments, the fluid comprising cells has a low conductivity or a high conductivity. In some embodiments, the fluid comprises a bodily fluid, blood, serum, plasma, urine, saliva, cerebrospinal fluid, body tissue, a food, a beverage, a growth medium, an environmental sample, a liquid, water, clonal cells, or a combination thereof. In some embodiments, the cells comprise clonal cells, pathogen cells, bacteria cells, viruses, plant cells, animal cells, insect cells, and/or combinations thereof. In some embodiments, the method further comprises sequencing the isolated nucleic acid. In some embodiments, the nucleic acid is sequenced by Sanger sequencing, pyrosequencing, ion semiconductor sequencing, polony sequencing, sequencing by ligation, DNA nanoball sequencing, sequencing by ligation, or single molecule sequencing. In some embodiments, the method further comprises performing a reaction on the DNA (e.g., fragmentation, restriction digestion, ligation). In some embodiments, the reaction occurs on or near the array or in the device. In some embodiments, the fluid comprising cells comprises no more than 10,000 cells.

Disclosed herein, in some embodiments, is a method for isolating a nucleic acid from a fluid comprising cells, the method comprising: a. applying the fluid to a device, the device comprising an array of electrodes capable of generating an AC electrokinetic field; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away, wherein the fluid is at a conductivity capable of concentrating a plurality of cells in the first AC electrokinetic field region. In some embodiments, the first AC electrokinetic field region is a dielectrophoretic field region. In some embodiments, the first AC electrokinetic field region is a dielectrophoretic low field region, and wherein the fluid conductivity is greater than 300 mS/m. In some embodiments, the second AC electrokinetic field region is a dielectrophoretic field region. In some embodiments, the method further comprises degradation of residual proteins after step (e). In some embodiments, the method further comprises flushing the degraded proteins from the nucleic acid. In some embodiments, the method further comprises collecting the nucleic acid. In some embodiments, the first AC electrokinetic field region is produced by an alternating current. In some embodiments, the first AC electrokinetic field region is produced using an alternating current having a voltage of 1 volt to 40 volts peak-peak; and/or a frequency of 5 Hz to 5,000,000 Hz, and duty cycles from 5% to 50%. In some embodiments, the second AC electrokinetic field region is a different region of the electrode array as the first AC electrokinetic field region. In some embodiments, the second AC electrokinetic field region is the same region of the electrode array as the first AC electrokinetic field region. In some embodiments, the second AC electrokinetic field region is produced by an alternating current. In some embodiments, the second AC electrokinetic field region is a dielectrophoretic high field region. In some embodiments, the second AC electrokinetic field region is produced using an alternating current having a voltage of 1 volt to 50 volts peak-peak; and/or a frequency of 5 Hz to 5,000,000 Hz, and duty cycles from 5% to 50%. In some embodiments, the electrodes are selectively energized to provide the first AC electrokinetic field region and subsequently or continuously selectively energized to provide the second AC electrokinetic field region. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the method further comprises amplifying the isolated nucleic acid by polymerase chain reaction. In some embodiments, the nucleic acid comprises DNA, RNA, or any combination thereof. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass. In some embodiments, the method is completed in less than about one hour. In some embodiments, centrifugation is not used. In some embodiments, the residual proteins are degraded by one or more of chemical degradation and enzymatic degradation. In some embodiments, the residual proteins are degraded by Proteinase K. In some embodiments, the residual proteins are degraded by an enzyme, the method further comprising inactivating the enzyme following degradation of the proteins. In some embodiments, the enzyme is inactivated by heat (e.g., 50 to 95° C. for 5-15 minutes). In some embodiments, the residual material and the degraded proteins are flushed in separate or concurrent steps. In some embodiments, the isolated nucleic acid is collected by (i) turning off the second AC electrokinetic field region; and (ii) eluting the nucleic acid from the array in an eluant. In some embodiments, nucleic acid is isolated in a form suitable for sequencing. In some embodiments, the nucleic acid is isolated in a fragmented form suitable for shotgun-sequencing. In some embodiments, the fluid comprising cells has a low conductivity or a high conductivity. In some embodiments, the fluid comprises a bodily fluid, blood, serum, plasma, urine, saliva, cerebrospinal fluid, body tissue, a food, a beverage, a growth medium, an environmental sample, a liquid, water, clonal cells, or a combination thereof. In some embodiments, the cells comprise clonal cells, pathogen cells, bacteria cells, viruses, plant cells, animal cells, insect cells, and/or combinations thereof. In some embodiments, the method further comprises sequencing the isolated nucleic acid. In some embodiments, the nucleic acid is sequenced by Sanger sequencing, pyrosequencing, ion semiconductor sequencing, polony sequencing, sequencing by ligation, DNA nanoball sequencing, sequencing by ligation, or single molecule sequencing. In some embodiments, the method further comprises performing a reaction on the DNA (e.g., fragmentation, restriction digestion, ligation). In some embodiments, the reaction occurs on or near the array or in the device. In some embodiments, the fluid comprising cells comprises no more than 10,000 cells.

In some embodiments, disclosed herein is a device for isolating a nucleic acid from a fluid comprising cells, the device comprising: a. a housing; b. a heater and/or a reservoir comprising a protein degradation agent; and c. a plurality of alternating current (AC) electrodes within the housing, the AC electrodes configured to be selectively energized to establish AC electrokinetic high field and AC electrokinetic low field regions, whereby AC electrokinetic effects provide for concentration of cells in low field regions of the device. In some embodiments, the plurality of electrodes is configured to be selectively energized to establish a dielectrophoretic high field and dielectrophoretic low field regions. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the protein degradation agent is Proteinase K. In some embodiments, the device further comprises a second reservoir comprising an eluant.

In some embodiments, disclosed herein is a system for isolating a nucleic acid from a fluid comprising cells, the system comprising: a. a device comprising a plurality of alternating current (AC) electrodes, the AC electrodes configured to be selectively energized to establish AC electrokinetic high field and AC electrokinetic low field regions, whereby AC electrokinetic effects provide for concentration of cells in high field regions of the device, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of sequencing DNA by Sanger sequencing or next generation sequencing methods; c. a software program capable of controlling the device comprising a plurality of AC electrodes, the module capable of sequencing DNA or a combination thereof; and d. a fluid comprising cells. In some embodiments, the plurality of electrodes is configured to be selectively energized to establish a dielectrophoretic high field and dielectrophoretic low field regions.

Disclosed herein, in some embodiments, is a device comprising: a. a plurality of alternating current (AC) electrodes, the AC electrodes configured to be selectively energized to establish AC electrokinetic high field and AC electrokinetic low field regions, wherein the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of thermocycling and amplifying nucleic acids. In some embodiments, the plurality of electrodes is configured to be selectively energized to establish a dielectrophoretic high field and dielectrophoretic low field regions. In some embodiments, the device is capable of isolating nucleic acids from a fluid comprising cells and performing amplification of the isolated nucleic acids. In some embodiments, the isolated nucleic acid is DNA or mRNA. In some embodiments, nucleic acid is isolated and amplification is performed in a single chamber. In some embodiments, nucleic acid is isolated and amplification is performed in multiple regions of a single chamber. In some embodiments, the device further comprises using at least one of an elution tube, a chamber and a reservoir to perform amplification. In some embodiments, amplification of the nucleic acid is polymerase chain reaction (PCR)-based. In some embodiments, amplification of the nucleic acid is performed in a serpentine microchannel comprising a plurality of temperature zones. In some embodiments, amplification is performed in aqueous droplets entrapped in immiscible fluids (i.e., digital PCR). In some embodiments, the thermocycling comprises convection. In some embodiments, the device comprises a surface contacting or proximal to the electrodes, wherein the surface is functionalized with biological ligands that are capable of selectively capturing biomolecules. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes comprises a passivation layer with a relative electrical permittivity from about 2.0 to about 4.0. In some embodiments, the surface selectively captures biomolecules by: a. nucleic acid hybridization; b. antibody-antigen interactions; c. biotin-avidin interactions; d. ionic or electrostatic interactions; or e. any combination thereof. In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the device comprises a plurality of microelectrode devices oriented (a) flat side by side, (b) facing vertically, or (c) facing horizontally. In some embodiments, the device comprises a module capable of performing Sanger sequencing. In some embodiments, the module capable of performing Sanger sequencing comprises a module capable of capillary electrophoresis, a module capable of multi-color fluorescence detection, or a combination thereof.

Disclosed herein, in some embodiments, is a device comprising: a. a plurality of alternating current (AC) electrodes, the AC electrodes configured to be selectively energized to establish AC electrokinetic high field and AC electrokinetic low field regions, wherein the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of performing sequencing. In some embodiments, the plurality of electrodes is configured to be selectively energized to establish a dielectrophoretic high field and dielectrophoretic low field regions. In some embodiments, the device comprises a surface contacting or proximal to the electrodes, wherein the surface is functionalized with biological ligands that are capable of selectively capturing biomolecules. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes comprises a passivation layer with a relative electrical permittivity from about 2.0 to about 4.0. In some embodiments, the surface selectively captures biomolecules by: a. nucleic acid hybridization; b. antibody-antigen interactions; c. biotin-avidin interactions; d. ionic or electrostatic interactions; or e. any combination thereof. In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the device comprises a plurality of microelectrode devices oriented (a) flat side by side, (b) facing vertically, or (c) facing horizontally. In some embodiments, the device comprises a module capable of performing next generation sequencing. In some embodiments, the module capable of performing next-generation sequencing is capable of performing pyrosequencing, ion semiconductor sequencing, polony sequencing, sequencing by ligation, DNA nanoball sequencing, or single molecule sequencing.

Disclosed herein, in some embodiments, is a method of isolating a nucleic acid from a fluid comprising cells, comprising a) performing a method disclosed herein; b) performing PCR amplification on the nucleic acid, or a cDNA version of the nucleic acid, to produce a PCR product; c) isolating the PCR product in a third AC electrokinetic region; d) performing Sanger chain termination reactions on the PCR product to produce a sequencing product of the nucleic acid; and e) performing electrophoretic separation of the sequencing product of the nucleic acid. In some embodiments, the third AC electrokinetic region is a dielectrophoretic field region. In some embodiments, the third AC electrokinetic region is a dielectrophoretic high field region. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the electrophoretic separation of the sequencing product of the nucleic acid is capillary electrophoresis. In some embodiments, the method further comprises the use of multicolor fluorescence detection to analyze the sequencing product of the nucleic acid. In some embodiments, all steps are performed on a single chip. In some embodiments, the fluid comprising cells comprises no more than 10,000 cells.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
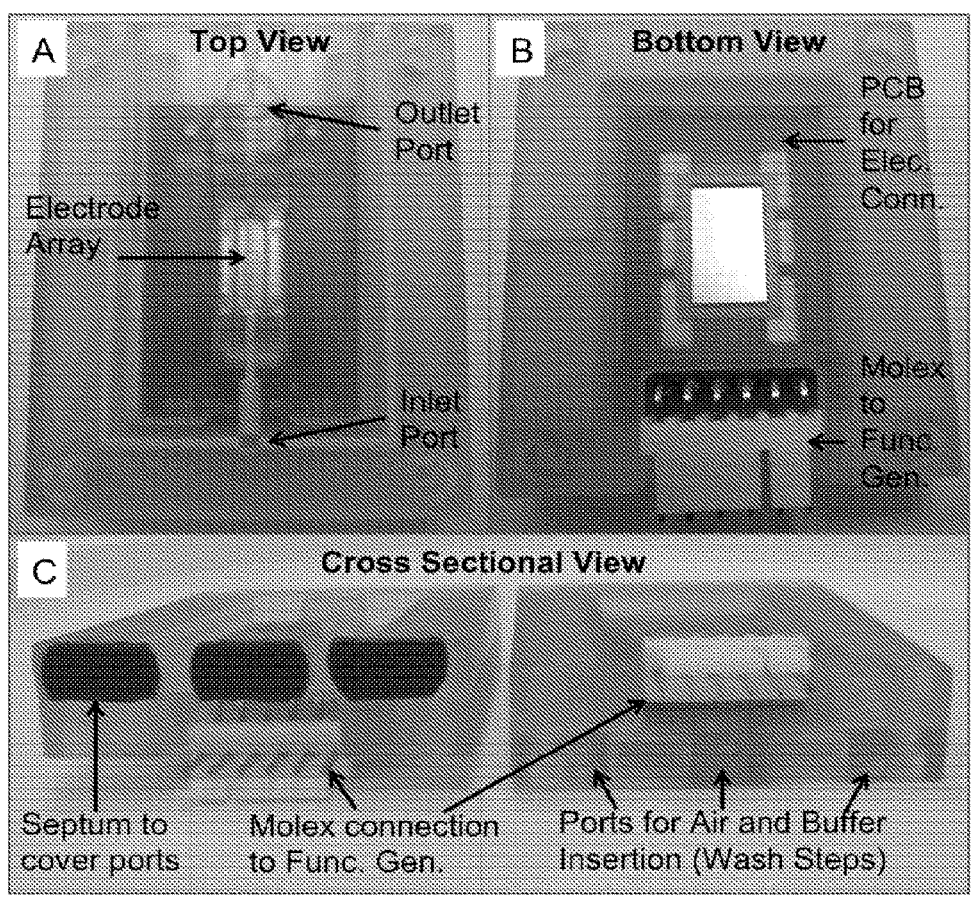
FIG. 1 shows a top view (A), a bottom view (B) and a cross-sectional view (C) of an exemplary device.

Described herein are methods, devices and systems suitable for isolating or separating particles or molecules from a fluid composition. In specific embodiments, provided herein are methods, devices and systems for isolating or separating a nucleic acid from a fluid comprising cells or other particulate material. In some aspects, the methods, devices and systems may allow for rapid separation of particles and molecules in a fluid composition. In other aspects, the methods, devices and systems may allow for rapid isolation of molecules from particles in a fluid composition. In various aspects, the methods, devices and systems may allow for a rapid procedure that requires a minimal amount of material and/or results in high purity DNA isolated from complex fluids such as blood or environmental samples.

Provided in certain embodiments herein are methods, devices and systems for isolating or separating particles or molecules from a fluid composition, the methods, devices, and systems comprising applying the fluid to a device comprising an array of electrodes and being capable of generating AC electrokinetic forces (e.g., when the array of electrodes are energized). In some embodiments, the dielectrophoretic field, is a component of AC electrokinetic force effects. In other embodiments, the component of AC electrokinetic force effects is AC electroosmosis or AC electrothermal effects. In some embodiments the AC electrokinetic force, including dielectrophoretic fields, comprises high-field regions (positive DEP, i.e. area where there is a strong concentration of electric field lines due to a non-uniform electric field) and/or low-field regions (negative DEP, i.e. area where there is a weak concentration of electric field lines due to a non-uniform electric field).

In specific instances, the particles or molecules (e.g., nucleic acid) are isolated (e.g., isolated or separated from cells) in a field region (e.g., a high field region) of the dielectrophoretic field. In some embodiments, the method, device, or system further includes one or more of the following steps: concentrating cells of interest in a first dielectrophoretic field region (e.g., a high field DEP region), lysing cells in the first dielectrophoretic field region, and/or concentrating nucleic acid in a first or second dielectrophoretic field region. In other embodiments, the method, device, or system includes one or more of the following steps: concentrating cells in a first dielectrophoretic field region (e.g., a low field DEP region), concentrating nucleic acid in a second dielectrophoretic field region (e.g., a high field DEP region), and washing away the cells and residual material. The method also optionally includes devices and/or systems capable of performing one or more of the following steps: washing or otherwise removing residual (e.g., cellular) material from the nucleic acid (e.g., rinsing the array with water or buffer while the nucleic acid is concentrated and maintained within a high field DEP region of the array), degrading residual proteins (e.g., residual proteins from lysed cells and/or other sources, such degradation occurring according to any suitable mechanism, such as with heat, a protease, or a chemical), flushing degraded proteins from the nucleic acid, and collecting the nucleic acid. In some embodiments, the result of the methods, operation of the devices, and operation of the systems described herein is an isolated nucleic acid, optionally of suitable quantity and purity for DNA sequencing.

In some instances, it is advantageous that the methods described herein are performed in a short amount of time, the devices are operated in a short amount of time, and the systems are operated in a short amount of time. In some embodiments, the period of time is short with reference to the "procedure time" measured from the time between adding the fluid to the device and obtaining isolated nucleic acid. In some embodiments, the procedure time is less than 3 hours, less than 2 hours, less than 1 hour, less than 30 minutes, less than 20 minutes, less than 10 minutes, or less than 5 minutes.

In another aspect, the period of time is short with reference to the "hands-on time" measured as the cumulative amount of time that a person must attend to the procedure from the time between adding the fluid to the device and obtaining isolated nucleic acid. In some embodiments, the hands-on time is less than 20 minutes, less than 10 minutes, less than 5 minute, less than 1 minute, or less than 30 seconds.

In some instances, it is advantageous that the devices described herein comprise a single vessel, the systems described herein comprise a device comprising a single vessel and the methods described herein can be performed in a single vessel, e.g., in a dielectrophoretic device as described herein. In some aspects, such a single-vessel embodiment minimizes the number of fluid handling steps and/or is performed in a short amount of time. In some instances, the present methods, devices and systems are contrasted with methods, devices and systems that use one or more centrifugation steps and/or medium exchanges. In some instances, centrifugation increases the amount of hands-on time required to isolate nucleic acids. In another aspect, the single-vessel procedure or device isolates nucleic acids using a minimal amount of consumable reagents.

Devices and Systems

In some embodiments, described herein are devices for collecting a nucleic acid from a fluid. In one aspect, described herein are devices for collecting a nucleic acid from a fluid comprising cells or other particulate material. In other aspects, the devices disclosed herein are capable of collecting and/or isolating nucleic acid from a fluid comprising cellular or protein material. In other instances, the devices disclosed herein are capable of collecting and/or isolating nucleic acid from cellular material.

In some embodiments, disclosed herein is a device for isolating a nucleic acid from a fluid comprising cells or other particulate material, the device comprising: a. a housing; b. a heater or thermal source and/or a reservoir comprising a protein degradation agent; and c. a plurality of alternating current (AC) electrodes within the housing, the AC electrodes configured to be selectively energized to establish AC electrokinetic high field and AC electrokinetic low field regions, whereby AC electrokinetic effects provide for concentration of cells in low field regions of the device. In some embodiments, the plurality of electrodes is configured to be selectively energized to establish a dielectrophoretic high field and dielectrophoretic low field regions. In some embodiments, the protein degradation agent is a protease. In some embodiments, the protein degradation agent is Proteinase K. In some embodiments, the device further comprises a second reservoir comprising an eluant.

In some embodiments, disclosed herein is a device comprising: a. a plurality of alternating current (AC) electrodes, the AC electrodes configured to be selectively energized to establish AC electrokinetic high field and AC electrokinetic low field regions; and b. a module capable of thermocycling and performing PCR or other enzymatic reactions. In some embodiments, the plurality of electrodes is configured to be selectively energized to establish a dielectrophoretic high field and dielectrophoretic low field regions. In some embodiments, the device is capable of isolating DNA from a fluid comprising cells and performing PCR amplification or other enzymatic reactions. In some embodiments, DNA is isolated and PCR or other enzymatic reaction is performed in a single chamber. In some embodiments, DNA is isolated and PCR or other enzymatic reaction is performed in multiple regions of a single chamber. In some embodiments, DNA is isolated and PCR or other enzymatic reaction is performed in multiple chambers.

In some embodiments, the device further comprises at least one of an elution tube, a chamber and a reservoir to perform PCR amplification or other enzymatic reaction. In some embodiments, PCR amplification or other enzymatic reaction is performed in a serpentine microchannel comprising a plurality of temperature zones. In some embodiments, PCR amplification or other enzymatic reaction is performed in aqueous droplets entrapped in immiscible fluids (i.e., digital PCR). In some embodiments, the thermocycling comprises convection. In some embodiments, the device comprises a surface contacting or proximal to the electrodes, wherein the surface is functionalized with biological ligands that are capable of selectively capturing biomolecules.

In some embodiments, disclosed herein is a system for isolating a nucleic acid from a fluid comprising cells or other particulate material, the system comprising: a. a device comprising a plurality of alternating current (AC) electrodes, the AC electrodes configured to be selectively energized to establish AC electrokinetic high field and AC electrokinetic low field regions, whereby AC electrokinetic effects provide for concentration of cells in high field regions of the device; and b. a sequencer, thermocycler or other device for performing enzymatic reactions on isolated or collected nucleic acid. In some embodiments, the plurality of electrodes is configured to be selectively energized to establish a dielectrophoretic high field and dielectrophoretic low field regions.

In various embodiments, DEP fields are created or capable of being created by selectively energizing an array of electrodes as described herein. The electrodes are optionally made of any suitable material resistant to corrosion, including metals, such as noble metals (e.g. platinum, platinum iridium alloy, palladium, gold, and the like). In various embodiments, electrodes are of any suitable size, of any suitable orientation, of any suitable spacing, energized or capable of being energized in any suitable manner, and the like such that suitable DEP and/or other electrokinetic fields are produced.

In some embodiments described herein are methods, devices and systems in which the electrodes are placed into separate chambers and positive DEP regions and negative DEP regions are created within an inner chamber by passage of the AC DEP field through pore or hole structures. Various geometries are used to form the desired positive DEP (high field) regions and DEP negative (low field) regions for carrying cellular, microparticle, nanoparticle, and nucleic acid separations. In some embodiments, pore or hole structures contain (or are filled with) porous material (hydrogels) or are covered with porous membrane structures. In some embodiments, by segregating the electrodes into separate chambers, such pore/hole structure DEP devices reduce electrochemistry effects, heating, or chaotic fluidic movement from occurring in the inner separation chamber during the DEP process.

In one aspect, described herein is a device comprising electrodes, wherein the electrodes are placed into separate chambers and DEP fields are created within an inner chamber by passage through pore structures. The exemplary device includes a plurality of electrodes and electrode-containing chambers within a housing. A controller of the device independently controls the electrodes, as described further in PCT patent publication WO 2009/146143 A2, which is incorporated herein for such disclosure.

In some embodiments, chambered devices are created with a variety of pore and/or hole structures (nanoscale, microscale and even macroscale) and contain membranes, gels or filtering materials which control, confine or prevent cells, nanoparticles or other entities from diffusing or being transported into the inner chambers while the AC/DC electric fields, solute molecules, buffer and other small molecules can pass through the chambers.

In various embodiments, a variety of configurations for the devices are possible. For example, a device comprising a larger array of electrodes, for example in a square or rectangular pattern configured to create a repeating non-uniform electric field to enable AC electrokinetics. For illustrative purposes only, a suitable electrode array may include, but is not limited to, a 10×10 electrode configuration, a 50×50 electrode configuration, a 10×100 electrode configuration, 20×100 electrode configuration, or a 20×80 electrode configuration.

Such devices include, but are not limited to, multiplexed electrode and chambered devices, devices that allow reconfigurable electric field patterns to be created, devices that combine DC electrophoretic and fluidic processes; sample preparation devices, sample preparation, enzymatic manipulation of isolated nucleic acid molecules and diagnostic devices that include subsequent detection and analysis, lab-on-chip devices, point-of-care and other clinical diagnostic systems or versions.

In some embodiments, a planar platinum electrode array device comprises a housing through which a sample fluid flows. In some embodiments, fluid flows from an inlet end to an outlet end, optionally comprising a lateral analyte outlet. The exemplary device includes multiple AC electrodes.

In some embodiments, the sample consists of a combination of micron-sized entities or cells, larger nanoparticulates and smaller nanoparticulates or biomolecules. In some embodiments, the micron-sized entities may comprise blood cells, platelets, bacteria and the like. In some embodiments, larger nanoparticulates comprise particulates in the range of about 10 nm and about 900 nm effective stokes diameter, and may comprise exosomes, high mw nucleic acids, including high mw DNA, oligo-nucleosome complexes, aggregated proteins, vesicle bound DNA, cell membrane fragments and cellular debris dispersed in the sample. In some embodiments, smaller nanoparticulates (<10 nm effective stokes diameter) comprise proteins such as immunoglobulins, human serum albumin, fibrinogen and other plasma proteins, smaller apoptotic DNA, and free ions.

In some embodiments, the AC electrokinetic field regions disclosed herein are capable of selectively isolating target particulates, including micron-sized entities, larger nanoparticulates and/or smaller nanoparticulates. In some embodiments, the AC electrokinetic field regions disclosed herein are capable of selectively isolating target particulates, including micron-sized entities, larger nanoparticulates and/or smaller nanoparticulates in complex biological or environmental samples. The target particulates are isolated in different field regions at or near the surface of the array, allowing non-target particulates or particulates that are not isolated at or near the surface of the array to be flushed from the array or cartridge.

In some embodiments, the planar electrode array device is a 60×20 electrode array that is optionally sectioned into three 20×20 arrays that can be separately controlled but operated simultaneously. The optional auxiliary DC electrodes can be switched on to positive charge, while the optional DC electrodes are switched on to negative charge for electrophoretic purposes. In some instances, each of the controlled AC and DC systems is used in both a continuous and/or pulsed manner (e.g., each can be pulsed on and off at relatively short time intervals) in various embodiments. The optional planar electrode arrays along the sides of the sample flow, when over-layered with nanoporous material (e.g., a hydrogel of synthetic polymer), are optionally used to generate DC electrophoretic forces as well as AC DEP. Additionally, microelectrophoretic separation processes is optionally carried out within the nanopore layers using planar electrodes in the array and/or auxiliary electrodes in the x-y-z dimensions.

In various embodiments these methods, devices and systems are operated in the AC frequency range of from 1,000 Hz to 100 MHz, at voltages which could range from approximately 1 volt to 2000 volts pk-pk; at DC voltages from 1 volt to 1000 volts, at flow rates of from 10 microliters per minute to 10 milliliter per minute, and in temperature ranges from 1° C. to 120° C. In some embodiments, the methods, devices and systems are operated in AC frequency ranges of from about 3 to about 15 kHz. In some embodiments, the methods, devices, and systems are operated at voltages of from 5-25 volts pk-pk. In some embodiments, the methods, devices and systems are operated at voltages of from about 1 to about 50 volts/cm. In some embodiments, the methods, devices and systems are operated at DC voltages of from about 1 to about 5 volts. In some embodiments, the methods, devices and systems are operated at a flow rate of from about 10 microliters to about 500 microliters per minute. In some embodiments, the methods, devices and systems are operated in temperature ranges of from about 20° C. to about 60° C. In some embodiments, the methods, devices and systems are operated in AC frequency ranges of from 1,000 Hz to 10 MHz. In some embodiments, the methods, devices and systems are operated in AC frequency ranges of from 1,000 Hz to 1 MHz. In some embodiments, the methods, devices and systems are operated in AC frequency ranges of from 1,000 Hz to 100 kHz. In some embodiments, the methods, devices and systems are operated in AC frequency ranges of from 1,000 Hz to 10 kHz. In some embodiments, the methods, devices and systems are operated in AC frequency ranges of from 10 kHz to 100 kHz. In some embodiments, the methods, devices and systems are operated in AC frequency ranges of from 100 kHz to 1 MHz. In some embodiments, the methods, devices and systems are operated at voltages from approximately 1 volt to 1500 volts pk-pk. In some embodiments, the methods, devices and systems are operated at voltages from approximately 1 volt to 1500 volts pk-pk. In some embodiments, the methods, devices and systems are operated at voltages from approximately 1 volt to 1000 volts pk-pk. In some embodiments, the methods, devices and systems are operated at voltages from approximately 1 volt to 500 volts pk-pk. In some embodiments, the methods, devices and systems are operated at voltages from approximately 1 volt to 250 volts pk-pk. In some embodiments, the methods, devices and systems are operated at voltages from approximately 1 volt to 100 volts pk-pk. In some embodiments, the methods, devices and systems are operated at voltages from approximately 1 volt to 50 volts pk-pk. In some embodiments, the methods, devices and systems are operated at DC voltages from 1 volt to 1000 volts. In some embodiments, the methods, devices and systems are operated at DC voltages from 1 volt to 500 volts. In some embodiments, the methods, devices and systems are operated at DC voltages from 1 volt to 250 volts. In some embodiments, the methods, devices and systems are operated at DC voltages from 1 volt to 100 volts. In some embodiments, the methods, devices and systems are operated at DC voltages from 1 volt to 50 volts. In some embodiments, the methods, devices, and systems are operated at flow rates of from 10 microliters per minute to 1 ml per minute. In some embodiments, the methods, devices, and systems are operated at flow rates of from 10 microliters per minute to 500 microliters per minute. In some embodiments, the methods, devices, and systems are operated at flow rates of from 10 microliters per minute to 250 microliters per minute. In some embodiments, the methods, devices, and systems are operated at flow rates of from 10 microliters per minute to 100 microliters per minute. In some embodiments, the methods, devices, and systems are operated in temperature ranges from 1° C. to 100° C. In some embodiments, the methods, devices, and systems are operated in temperature ranges from 20° C. to 95° C. In some embodiments, the methods, devices, and systems are operated in temperature ranges from 25° C. to 100° C. In some embodiments, the methods, devices, and systems are operated at room temperature.

In some embodiments, the controller independently controls each of the electrodes. In some embodiments, the controller is externally connected to the device such as by a socket and plug connection, or is integrated with the device housing.

Also described herein are scaled sectioned (x-y dimensional) arrays of robust electrodes and strategically placed (x-y-z dimensional) arrangements of auxiliary electrodes that combine DEP, electrophoretic, and fluidic forces, and use thereof. In some embodiments, clinically relevant volumes of blood, serum, plasma, or other samples are more directly analyzed under higher ionic strength and/or conductance conditions. Described herein is the overlaying of robust electrode structures (e.g. platinum, palladium, gold, etc.) with one or more porous layers of materials (natural or synthetic porous hydrogels, membranes, controlled nanopore materials, and thin dielectric layered materials) to reduce the effects of any electrochemistry (electrolysis) reactions, heating, and chaotic fluid movement that may occur on or near the electrodes, and still allow the effective separation of cells, bacteria, virus, nanoparticles, DNA, and other biomolecules to be carried out. In some embodiments, in addition to using AC frequency crossover points to achieve higher resolution separations, on-device (on-array) DC microelectrophoresis is used for secondary separations. For example, the separation of DNA nanoparticulates (20-50 kb), high molecular weight DNA (5-20 kb), intermediate molecular weight DNA (1-5 kb), and lower molecular weight DNA (0.1-1 kb) fragments may be accomplished through DC microelectrophoresis on the array. In some embodiments, the device is sub-sectioned, optionally for purposes of concurrent separations of different blood cells, bacteria and virus, and DNA carried out simultaneously on such a device.

In some embodiments, the device comprises a housing and a heater or thermal source and/or a reservoir comprising a protein degradation agent. In some embodiments, the heater or thermal source is capable of increasing the temperature of the fluid to a desired temperature (e.g., to a temperature suitable for degrading proteins, about 30° C., 40° C., 50° C., 60° C., 70° C., or the like). In some embodiments, the heater or thermal source is suitable for operation as a PCR thermocycler. IN other embodiments, the heater or thermal source is used to maintain a constant temperature (isothermal conditions). In some embodiments, the protein degradation agent is a protease. In other embodiments, the protein degradation agent is Proteinase K and the heater or thermal source is used to inactivate the protein degradation agent.

In some embodiments, the device also comprises a plurality of alternating current (AC) electrodes within the housing, the AC electrodes capable of being configured to be selectively energized to establish dielectrophoretic (DEP) high field and dielectrophoretic (DEP) low field regions, whereby AC electrokinetic effects provide for concentration of cells in low field regions of the device. In some embodiments, the electrodes are selectively energized to provide the first AC electrokinetic field region and subsequently or continuously selectively energized to provide the second AC electrokinetic field region. For example, further description of the electrodes and the concentration of cells in DEP fields is found in PCT patent publication WO 2009/146143 A2, which is incorporated herein for such disclosure.

In some embodiments, the device comprises a second reservoir comprising an eluant. The eluant is any fluid suitable for eluting the isolated nucleic acid from the device. In some instances the eluant is water or a buffer. In some instances, the eluant comprises reagents required for a DNA sequencing method.

Also provided herein are systems and devices comprising a plurality of alternating current (AC) electrodes, the AC electrodes configured to be selectively energized to establish dielectrophoretic (DEP) high field and dielectrophoretic (DEP) low field regions. In some instances, AC electrokinetic effects provide for concentration of cells in low field regions and/or concentration (or collection or isolation) of molecules (e.g., macromolecules, such as nucleic acid) in high field regions of the DEP field.

Also provided herein are systems and devices comprising a plurality of direct current (DC) electrodes. In some embodiments, the plurality of DC electrodes comprises at least two rectangular electrodes, spread throughout the array. In some embodiments, the electrodes are located at the edges of the array. In some embodiments, DC electrodes are interspersed between AC electrodes.

In some embodiments, a system or device described herein comprises a means for manipulating nucleic acid. In some embodiments, a system or device described herein includes a means of performing enzymatic reactions. In other embodiments, a system or device described herein includes a means of performing polymerase chain reaction, isothermal amplification, ligation reactions, restriction analysis, nucleic acid cloning, transcription or translation assays, or other enzymatic-based molecular biology assay. In yet other embodiments, a system or device described herein includes a means of performing Quantitative Real Time PCR, including of nuclear or mitochondrial DNA, enzyme-linked immunosorbent assays (ELISA), direct SYBR gold assays, direct PicoGreen assays, loss of heterozygosity (LOH) of microsatellite markers, optionally followed by electrophoresis analysis, including but not limited to capillary electrophoresis analysis, sequencing and/or cloning, including next generation sequencing, methylation analysis, including but not limited to modified semi-nested or nested methylation specific PCR, DNA specific PCR (MSP), quantification of minute amounts of DNA after bisulfitome amplification (qMAMBRA), as well as methylation on beads, mass-based analysis, including but not limited to MALDI-ToF (matrix-assisted laser desorption/ionization time of flight analysis, optionally in combination with PCR, and digital PCR.

In some embodiments, a system or device described herein comprises a nucleic acid sequencer. The sequencer is optionally any suitable DNA sequencing device including but not limited to a Sanger sequencer, pyro-sequencer, ion semiconductor sequencer, polony sequencer, sequencing by ligation device, DNA nanoball sequencing device, sequencing by ligation device, or single molecule sequencing device.

In some embodiments, a system or device described herein is capable of maintaining a constant temperature. In some embodiments, a system or device described herein is capable of cooling the array or chamber. In some embodiments, a system or device described herein is capable of heating the array or chamber. In some embodiments, a system or device described herein comprises a thermocycler. In some embodiments, the devices disclosed herein comprises a localized temperature control element. In some embodiments, the devices disclosed herein are capable of both sensing and controlling temperature.

In some embodiments, the devices further comprise heating or thermal elements. In some embodiments, a heating or thermal element is localized underneath an electrode. In some embodiments, the heating or thermal elements comprise a metal. In some embodiments, the heating or thermal elements comprise tantalum, aluminum, tungsten, or a combination thereof. Generally, the temperature achieved by a heating or thermal element is proportional to the current running through it. In some embodiments, the devices disclosed herein comprise localized cooling elements. In some embodiments, heat resistant elements are placed directly under the exposed electrode array. In some embodiments, the devices disclosed herein are capable of achieving and maintaining a temperature between about 20° C. and about 120° C. In some embodiments, the devices disclosed herein are capable of achieving and maintaining a temperature between about 30° C. and about 100° C. In other embodiments, the devices disclosed herein are capable of achieving and maintaining a temperature between about 20° C. and about 95° C. In some embodiments, the devices disclosed herein are capable of achieving and maintaining a temperature between about 25° C. and about 90° C., between about 25° C. and about 85° C., between about 25° C. and about 75° C., between about 25° C. and about 65° C. or between about 25° C. and about 55° C. In some embodiments, the devices disclosed herein are capable of achieving and maintaining a temperature of about 20° C., about 30° C., about 40° C., about 50° C., about 60° C., about 70° C., about 80° C., about 90° C., about 100° C., about 110° C. or about 120° C.

Electrodes

The plurality of alternating current electrodes are optionally configured in any manner suitable for the separation processes described herein. For example, further description of the system or device including electrodes and/or concentration of cells in DEP fields is found in PCT patent publication WO 2009/146143, which is incorporated herein for such disclosure.

In some embodiments, the electrodes disclosed herein can comprise any suitable metal. In some embodiments, the electrodes can include but are not limited to: aluminum, copper, carbon, iron, silver, gold, palladium, platinum, iridium, platinum iridium alloy, ruthenium, rhodium, osmium, tantalum, titanium, tungsten, polysilicon, and indium tin oxide, or combinations thereof, as well as silicide materials such as platinum silicide, titanium silicide, gold silicide, or tungsten silicide. In some embodiments, the electrodes can comprise a conductive ink capable of being screen-printed.

In some embodiments, the edge to edge (E2E) to diameter ratio of an electrode is about 0.5 mm to about 5 mm. In some embodiments, the E2E to diameter ratio is about 1 mm to about 4 mm. In some embodiments, the E2E to diameter ratio is about 1 mm to about 3 mm. In some embodiments, the E2E to diameter ratio is about 1 mm to about 2 mm. In some embodiments, the E2E to diameter ratio is about 2 mm to about 5 mm. In some embodiments, the E2E to diameter ratio is about 1 mm. In some embodiments, the E2E to diameter ratio is about 2 mm. In some embodiments, the E2E to diameter ratio is about 3 mm. In some embodiments, the E2E to diameter ratio is about 4 mm. In some embodiments, the E2E to diameter ratio is about 5 mm.

In some embodiments, the electrodes disclosed herein are dry-etched. In some embodiments, the electrodes are wet etched. In some embodiments, the electrodes undergo a combination of dry etching and wet etching.

In some embodiments, each electrode is individually site-controlled.

In some embodiments, an array of electrodes is controlled as a unit.

In some embodiments, a passivation layer is employed. In some embodiments, a passivation layer can be formed from any suitable material known in the art. In some embodiments, the passivation layer comprises silicon nitride. In some embodiments, the passivation layer comprises silicon dioxide. In some embodiments, the passivation layer has a relative electrical permittivity of from about 2.0 to about 8.0. In some embodiments, the passivation layer has a relative electrical permittivity of from about 3.0 to about 8.0, about 4.0 to about 8.0 or about 5.0 to about 8.0. In some embodiments, the passivation layer has a relative electrical permittivity of about 2.0 to about 4.0. In some embodiments, the passivation layer has a relative electrical permittivity of from about 2.0 to about 3.0. In some embodiments, the passivation layer has a relative electrical permittivity of about 2.0, about 2.5, about 3.0, about 3.5 or about 4.0.

In some embodiments, the passivation layer is between about 0.1 microns and about 10 microns in thickness. In some embodiments, the passivation layer is between about 0.5 microns and 8 microns in thickness. In some embodiments, the passivation layer is between about 1.0 micron and 5 microns in thickness. In some embodiments, the passivation layer is between about 1.0 micron and 4 microns in thickness. In some embodiments, the passivation layer is between about 1.0 micron and 3 microns in thickness. In some embodiments, the passivation layer is between about 0.25 microns and 2 microns in thickness. In some embodiments, the passivation layer is between about 0.25 microns and 1 micron in thickness.

In some embodiments, the passivation layer is comprised of any suitable insulative low k dielectric material, including but not limited to silicon nitride or silicon dioxide. In some embodiments, the passivation layer is chosen from the group consisting of polyamids, carbon, doped silicon nitride, carbon doped silicon dioxide, fluorine doped silicon nitride, fluorine doped silicon dioxide, porous silicon dioxide, or any combinations thereof. In some embodiments, the passivation layer can comprise a dielectric ink capable of being screen-printed.

Electrode Geometry

In some embodiments, the electrodes disclosed herein can be arranged in any manner suitable for practicing the methods disclosed herein.

In some embodiments, the electrodes are in a dot configuration, e.g. the electrodes comprises a generally circular or round configuration. In some embodiments, the angle of orientation between dots is from about 25° to about 60°. In some embodiments, the angle of orientation between dots is from about 30° to about 55°. In some embodiments, the angle of orientation between dots is from about 30° to about 50°. In some embodiments, the angle of orientation between dots is from about 35° to about 45°. In some embodiments, the angle of orientation between dots is about 25°. In some embodiments, the angle of orientation between dots is about 30°. In some embodiments, the angle of orientation between dots is about 35°. In some embodiments, the angle of orientation between dots is about 40°. In some embodiments, the angle of orientation between dots is about 45°. In some embodiments, the angle of orientation between dots is about 50°. In some embodiments, the angle of orientation between dots is about 55°. In some embodiments, the angle of orientation between dots is about 60°.

In some embodiments, the electrodes are in a substantially elongated configuration.

Figure 8:
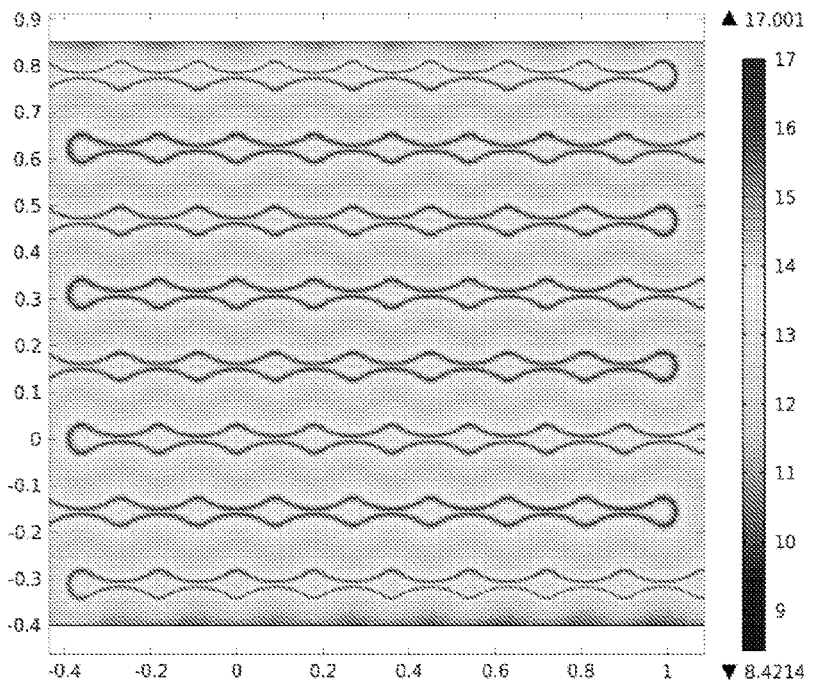
FIG. 8 exemplifies a wavy electrode configuration, as disclosed herein. The edge to edge distance between electrodes is generally equidistant throughout. A wavy electrode configuration maximizes electrode surface area while maintaining alternating non-uniform electric field to induce ACE gradient to enable DEP, ACEO, ACET, and other ACE forces.
Figure 8:
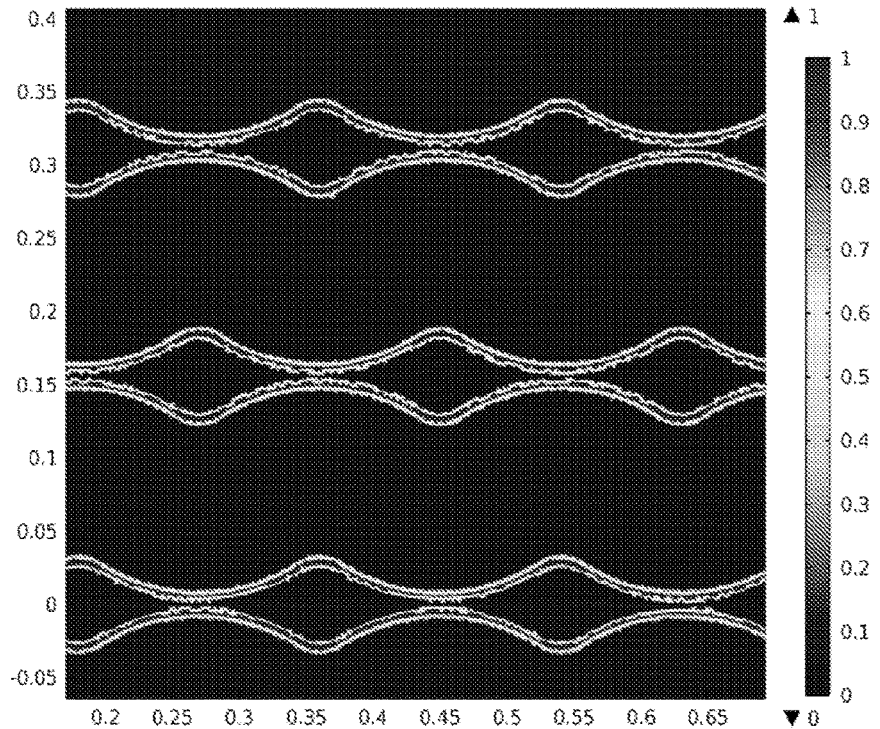
Figure 9:
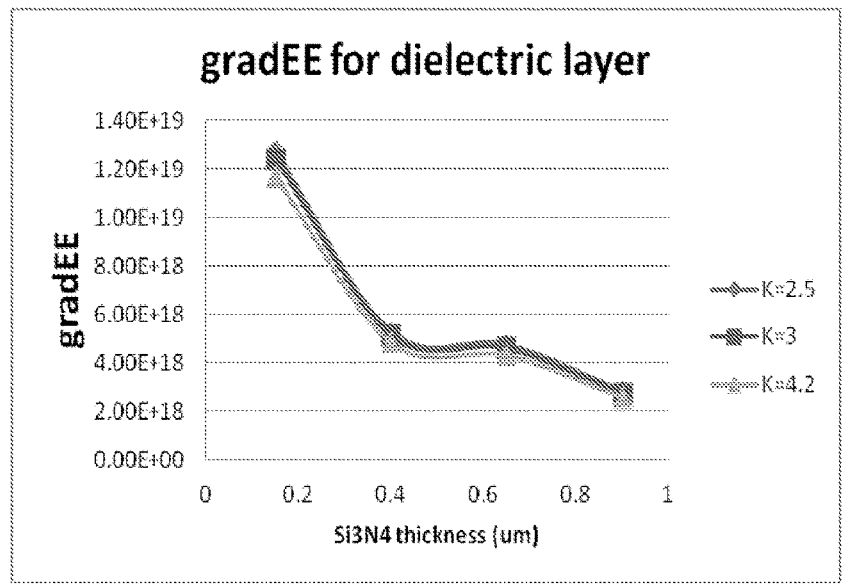
FIG. 9 exemplifies how the E-field gradient at a dielectric layer corner based on silicon nitride thickness. Lower K and lower thickness resulted in higher E-field gradient (bending) at a dielectric layer corner.
Figure 9:
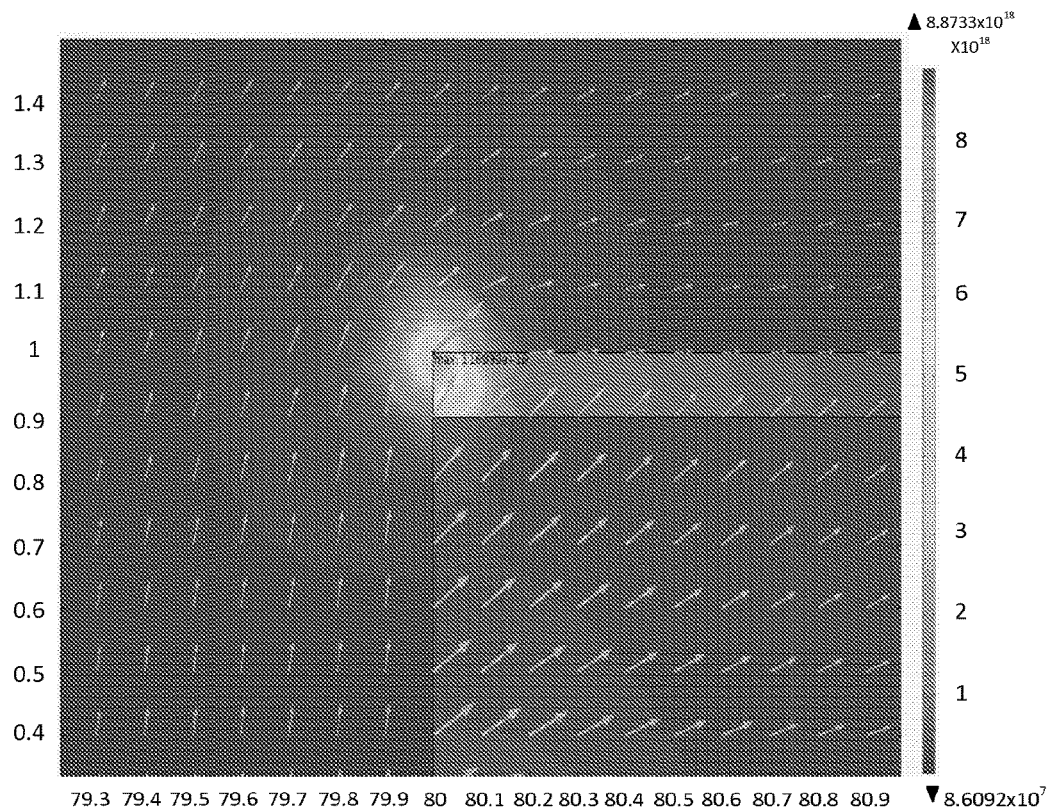

In some embodiments, the electrodes are in a configuration resembling wavy or nonlinear lines. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the electrodes are strips resembling wavy lines, as depicted in FIG. 8. In some embodiments, the edge to edge distance between the electrodes is equidistant, or roughly equidistant throughout the wavy line configuration. In some embodiments, the use of wavy line electrodes, as disclosed herein, lead to an enhanced DEP field gradient.

In some embodiments, the electrodes disclosed herein are in a planar configuration. In some embodiments, the electrodes disclosed herein are in a non-planar configuration.

In some embodiments, the devices disclosed herein surface selectively captures biomolecules on its surface. For example, the devices disclosed herein may capture biomolecules, such as nucleic acids, by, for example, a. nucleic acid hybridization; b. antibody-antigen interactions; c. biotin-avidin interactions; d. ionic or electrostatic interactions; or e. any combination thereof. The devices disclosed herein, therefore, may incorporate a functionalized surface which includes capture molecules, such as complementary nucleic acid probes, antibodies or other protein captures capable of capturing biomolecules (such as nucleic acids), biotin or other anchoring captures capable of capturing complementary target molecules such as avidin, capture molecules capable of capturing biomolecules (such as nucleic acids) by ionic or electrostatic interactions, or any combination thereof.

In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the methods disclosed herein include use of additives which reduce non-specific binding interactions by interfering in such interactions, such as Tween 20 and the like, bovine serum albumin, nonspecific immunoglobulins, etc.

In some embodiments, the device comprises a plurality of microelectrode devices oriented (a) flat side by side, (b) facing vertically, or (c) facing horizontally. In other embodiments, the electrodes are in a sandwiched configuration, e.g. stacked on top of each other in a vertical format.

Hydrogels

Overlaying electrode structures with one or more layers of materials can reduce the deleterious electrochemistry effects, including but not limited to electrolysis reactions, heating, and chaotic fluid movement that may occur on or near the electrodes, and still allow the effective separation of cells, bacteria, virus, nanoparticles, DNA, and other biomolecules to be carried out. In some embodiments, the materials layered over the electrode structures may be one or more porous layers. In other embodiments, the one or more porous layers is a polymer layer. In other embodiments, the one or more porous layers is a hydrogel.

In general, the hydrogel should have sufficient mechanical strength and be relatively chemically inert such that it will be able to endure the electrochemical effects at the electrode surface without disconfiguration or decomposition. In general, the hydrogel is sufficiently permeable to small aqueous ions, but keeps biomolecules away from the electrode surface.

In some embodiments, the hydrogel is a single layer, or coating.

In some embodiments, the hydrogel comprises a gradient of porosity, wherein the bottom of the hydrogel layer has greater porosity than the top of the hydrogel layer.

In some embodiments, the hydrogel comprises multiple layers or coatings. In some embodiments, the hydrogel comprises two coats. In some embodiments, the hydrogel comprises three coats. In some embodiments, the bottom (first) coating has greater porosity than subsequent coatings.

In some embodiments, the top coat is has less porosity than the first coating. In some embodiments, the top coat has a mean pore diameter that functions as a size cut-off for particles of greater than 100 picometers in diameter.

In some embodiments, the hydrogel has a conductivity from about 0.001 S/m to about 10 S/m. In some embodiments, the hydrogel has a conductivity from about 0.01 S/m to about 10 S/m. In some embodiments, the hydrogel has a conductivity from about 0.1 S/m to about 10 S/m. In some embodiments, the hydrogel has a conductivity from about 1.0 S/m to about 10 S/m. In some embodiments, the hydrogel has a conductivity from about 0.01 S/m to about 5 S/m. In some embodiments, the hydrogel has a conductivity from about 0.01 S/m to about 4 S/m. In some embodiments, the hydrogel has a conductivity from about 0.01 S/m to about 3 S/m. In some embodiments, the hydrogel has a conductivity from about 0.01 S/m to about 2 S/m. In some embodiments, the hydrogel has a conductivity from about 0.1 S/m to about 5 S/m. In some embodiments, the hydrogel has a conductivity from about 0.1 S/m to about 4 S/m. In some embodiments, the hydrogel has a conductivity from about 0.1 S/m to about 3 S/m. In some embodiments, the hydrogel has a conductivity from about 0.1 S/m to about 2 S/m. In some embodiments, the hydrogel has a conductivity from about 0.1 S/m to about 1.5 S/m. In some embodiments, the hydrogel has a conductivity from about 0.1 S/m to about 1.0 S/m.

In some embodiments, the hydrogel has a conductivity of about 0.1 S/m. In some embodiments, the hydrogel has a conductivity of about 0.2 S/m. In some embodiments, the hydrogel has a conductivity of about 0.3 S/m. In some embodiments, the hydrogel has a conductivity of about 0.4 S/m. In some embodiments, the hydrogel has a conductivity of about 0.5 S/m. In some embodiments, the hydrogel has a conductivity of about 0.6 S/m. In some embodiments, the hydrogel has a conductivity of about 0.7 S/m. In some embodiments, the hydrogel has a conductivity of about 0.8 S/m. In some embodiments, the hydrogel has a conductivity of about 0.9 S/m. In some embodiments, the hydrogel has a conductivity of about 1.0 S/m.

In some embodiments, the hydrogel has a thickness from about 0.1 microns to about 10 microns. In some embodiments, the hydrogel has a thickness from about 0.1 microns to about 5 microns. In some embodiments, the hydrogel has a thickness from about 0.1 microns to about 4 microns. In some embodiments, the hydrogel has a thickness from about 0.1 microns to about 3 microns. In some embodiments, the hydrogel has a thickness from about 0.1 microns to about 2 microns. In some embodiments, the hydrogel has a thickness from about 1 micron to about 5 microns. In some embodiments, the hydrogel has a thickness from about 1 micron to about 4 microns. In some embodiments, the hydrogel has a thickness from about 1 micron to about 3 microns. In some embodiments, the hydrogel has a thickness from about 1 micron to about 2 microns. In some embodiments, the hydrogel has a thickness from about 0.5 microns to about 1 micron.

In some embodiments, the viscosity of a hydrogel solution prior to spin-coating ranges from about 0.5 cP to about 5 cP. In some embodiments, a single coating of hydrogel solution has a viscosity of between about 0.75 cP and 5 cP prior to spin-coating. In some embodiments, in a multi-coat hydrogel, the first hydrogel solution has a viscosity from about 0.5 cP to about 1.5 cP prior to spin coating. In some embodiments, the second hydrogel solution has a viscosity from about 1 cP to about 3 cP. The viscosity of the hydrogel solution is based on the polymers concentration (0.1%-10%)

and polymers molecular weight (10,000 to 300,000) in the solvent and the starting viscosity of the solvent.

In some embodiments, the first hydrogel coating has a thickness between about 0.5 microns and 1 micron. In some embodiments, the first hydrogel coating has a thickness between about 0.5 microns and 0.75 microns. In some embodiments, the first hydrogel coating has a thickness between about 0.75 and 1 micron. In some embodiments, the second hydrogel coating has a thickness between about 0.2 microns and 0.5 microns. In some embodiments, the second hydrogel coating has a thickness between about 0.2 and 0.4 microns. In some embodiments, the second hydrogel coating has a thickness between about 0.2 and 0.3 microns. In some embodiments, the second hydrogel coating has a thickness between about 0.3 and 0.4 microns.

In some embodiments, the hydrogel comprises any suitable synthetic polymer forming a hydrogel. In general, any sufficiently hydrophilic and polymerizable molecule may be utilized in the production of a synthetic polymer hydrogel for use as disclosed herein. Polymerizable moieties in the monomers may include alkenyl moieties including but not limited to substituted or unsubstituted $\alpha,\beta$, unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms. In some embodiments, acryloyl or acrylamido monomers such as acrylates, methacrylates, acrylamides, methacrylamides, etc., are useful for formation of hydrogels as disclosed herein. More preferred acrylamido monomers include acrylamides, N-substituted acrylamides, N-substituted methacrylamides, and methacrylamide. In some embodiments, a hydrogel comprises polymers such as epoxide-based polymers, vinyl-based polymers, allyl-based polymers, homoallyl-based polymers, cyclic anhydride-based polymers, ester-based polymers, ether-based polymers, alkylene-glycol based polymers (e.g., polypropylene glycol), and the like.

In some embodiments, the hydrogel comprises polyhydroxyethylmethacrylate (pHEMA), cellulose acetate, cellulose acetate phthalate, cellulose acetate butyrate, or any appropriate acrylamide or vinyl-based polymer, or a derivative thereof.

In some embodiments, the hydrogel is applied by vapor deposition.

In some embodiments, the hydrogel is polymerized via atom-transfer radical-polymerization via (ATRP).

In some embodiments, the hydrogel is polymerized via reversible addition—fragmentation chain-transfer (RAFT) polymerization.

In some embodiments, additives are added to a hydrogel to increase conductivity of the gel. In some embodiments, hydrogel additives are conductive polymers (e.g., PEDOT: PSS), salts (e.g., copper chloride), metals (e.g., gold), plasticizers (e.g., PEG200, PEG 400, or PEG 600), or co-solvents.

In some embodiments, the hydrogel also comprises compounds or materials which help maintain the stability of the DNA hybrids, including, but not limited to histidine, histidine peptides, polyhistidine, lysine, lysine peptides, and other cationic compounds or substances.

Dielectrophoretic Fields

In some embodiments, the methods, devices and systems described herein provide a mechanism to collect, separate, or isolate cells, particles, and/or molecules (such as nucleic acid) from a fluid material (which optionally contains other materials, such as contaminants, residual cellular material, or the like).

In some embodiments, an AC electrokinetic field is generated to collect, separate or isolate biomolecules, such as nucleic acids. In some embodiments, the AC electrokinetic field is a dielectrophoretic field. Accordingly, in some embodiments dielectrophoresis (DEP) is utilized in various steps of the methods described herein.

In some embodiments, the devices and systems described herein are capable of generating DEP fields, and the like. In specific embodiments, DEP is used to concentrate cells and/or nucleic acids (e.g., concurrently or at different times). In certain embodiments, methods described herein further comprise energizing the array of electrodes so as to produce the first, second, and any further optional DEP fields. In some embodiments, the devices and systems described herein are capable of being energized so as to produce the first, second, and any further optional DEP fields.

DEP is a phenomenon in which a force is exerted on a dielectric particle when it is subjected to a non-uniform electric field. Depending on the step of the methods described herein, aspects of the devices and systems described herein, and the like, the dielectric particle in various embodiments herein is a biological cell and/or a molecule, such as a nucleic acid molecule. Different steps of the methods described herein or aspects of the devices or systems described herein may be utilized to isolate and separate different components, such as intact cells or other particular material; further, different field regions of the DEP field may be used in different steps of the methods or aspects of the devices and systems described herein. This dielectrophoretic force does not require the particle to be charged. In some instances, the strength of the force depends on the medium and the specific particles' electrical properties, on the particles' shape and size, as well as on the frequency of the electric field. In some instances, fields of a particular frequency selectivity manipulate particles. In certain aspects described herein, these processes allow for the separation of cells and/or smaller particles (such as molecules, including nucleic acid molecules) from other components (e.g., in a fluid medium) or each other.

In various embodiments provided herein, a method described herein comprises producing a first DEP field region and a second DEP field region with the array. In various embodiments provided herein, a device or system described herein is capable of producing a first DEP field region and a second DEP field region with the array. In some instances, the first and second field regions are part of a single field (e.g., the first and second regions are present at the same time, but are found at different locations within the device and/or upon the array). In some embodiments, the first and second field regions are different fields (e.g. the first region is created by energizing the electrodes at a first time, and the second region is created by energizing the electrodes a second time). In specific aspects, the first DEP field region is suitable for concentrating or isolating cells (e.g., into a low field DEP region). In some embodiments, the second DEP field region is suitable for concentrating smaller particles, such as molecules (e.g., nucleic acid), for example into a high field DEP region. In some instances, a method described herein optionally excludes use of either the first or second DEP field region.

In some embodiments, the first DEP field region is in the same chamber of a device as disclosed herein as the second DEP field region. In some embodiments, the first DEP field region and the second DEP field region occupy the same area of the array of electrodes.

In some embodiments, the first DEP field region is in a separate chamber of a device as disclosed herein, or a separate device entirely, from the second DEP field region.

First DEP Field Region

In some aspects, e.g., high conductance buffers (>100 mS/m), the method described herein comprises applying a fluid comprising cells or other particulate material to a device comprising an array of electrodes, and, thereby, concentrating the cells in a first DEP field region. In some aspects, the devices and systems described herein are capable of applying a fluid comprising cells or other particulate material to the device comprising an array of electrodes, and, thereby, concentrating the cells in a first DEP field region. Subsequent or concurrent second, or optional third and fourth DEP regions, may collect or isolate other fluid components, including biomolecules, such as nucleic acids.

The first DEP field region may be any field region suitable for concentrating cells from a fluid. For this application, the cells are generally concentrated near the array of electrodes. In some embodiments, the first DEP field region is a dielectrophoretic low field region. In some embodiments, the first DEP field region is a dielectrophoretic high field region. In some aspects, e.g. low conductance buffers (<100 mS/m), the method described herein comprises applying a fluid comprising cells to a device comprising an array of electrodes, and, thereby, concentrating the cells or other particulate material in a first DEP field region.

In some aspects, the devices and systems described herein are capable of applying a fluid comprising cells or other particulate material to the device comprising an array of electrodes, and concentrating the cells in a first DEP field region. In various embodiments, the first DEP field region may be any field region suitable for concentrating cells from a fluid. In some embodiments, the cells are concentrated on the array of electrodes. In some embodiments, the cells are captured in a dielectrophoretic high field region. In some embodiments, the cells are captured in a dielectrophoretic low-field region. High versus low field capture is generally dependent on the conductivity of the fluid, wherein generally, the crossover point is between about 300-500 mS/m. In some embodiments, the first DEP field region is a dielectrophoretic low field region performed in fluid conductivity of greater than about 300 mS/m. In some embodiments, the first DEP field region is a dielectrophoretic low field region performed in fluid conductivity of less than about 300 mS/m. In some embodiments, the first DEP field region is a dielectrophoretic high field region performed in fluid conductivity of greater than about 300 mS/m. In some embodiments, the first DEP field region is a dielectrophoretic high field region performed in fluid conductivity of less than about 300 mS/m. In some embodiments, the first DEP field region is a dielectrophoretic low field region performed in fluid conductivity of greater than about 500 mS/m. In some embodiments, the first DEP field region is a dielectrophoretic low field region performed in fluid conductivity of less than about 500 mS/m. In some embodiments, the first DEP field region is a dielectrophoretic high field region performed in fluid conductivity of greater than about 500 mS/m.

In some embodiments, the first DEP field region is a dielectrophoretic high field region performed in fluid conductivity of less than about 500 mS/m.

In some embodiments, the first dielectrophoretic field region is produced by an alternating current. The alternating current has any amperage, voltage, frequency, and the like suitable for concentrating cells. In some embodiments, the first dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the first DEP field region is produced using an alternating current having a voltage of 5-25 volts peak to peak. In some embodiments, the first DEP field region is produced using an alternating current having a frequency of from 3-15 kHz. In some embodiments, the first DEP field region is produced using an alternating current having an amperage of 1 milliamp to 1 amp. In some embodiments, the first DEP field region is produced using an alternating current having an amperage of 0.1 micro Amperes-1 Ampere. In some embodiments, the first DEP field region is produced using an alternating current having an amperage of 1 micro Amperes-1 Ampere. In some embodiments, the first DEP field region is produced using an alternating current having an amperage of 100 micro Amperes-1 Ampere. In some embodiments, the first DEP field region is produced using an alternating current having an amperage of 500 micro Amperes-500 milli Amperes. In some embodiments, the first DEP field region is produced using an alternating current having a voltage of 1-25 Volts peak to peak. In some embodiments, the first DEP field region is produced using an alternating current having a voltage of 1-10 Volts peak to peak. In some embodiments, the first DEP field region is produced using an alternating current having a voltage of 25-50 Volts peak to peak. In some embodiments, the first DEP field region is produced using a frequency of from 10-1,000,000 Hz. In some embodiments, the first DEP field region is produced using a frequency of from 100-100,000 Hz. In some embodiments, the first DEP field region is produced using a frequency of from 100-10,000 Hz. In some embodiments, the first DEP field region is produced using a frequency of from 10,000-100,000 Hz. In some embodiments, the first DEP field region is produced using a frequency of from 100,000-1,000,000 Hz.

In some embodiments, the first dielectrophoretic field region is produced by a direct current. The direct current has any amperage, voltage, frequency, and the like suitable for concentrating cells. In some embodiments, the first dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the first DEP field region is produced using a direct current having an amperage of 1 micro Amperes-1 Amperes. In some embodiments, the first DEP field region is produced using a direct current having an amperage of 100 micro Amperes-500 milli Amperes. In some embodiments, the first DEP field region is produced using a direct current having an amperage of 1 milli Amperes-1 Amperes. In some embodiments, the first DEP field region is produced using a direct current having an amperage of 1 micro Amperes-1 milli Amperes. In some embodiments, the first DEP field region is produced using a direct current having a pulse width of 500 milliseconds-500 seconds. In some embodiments, the first DEP field region is produced using a direct current having a pulse width of 500 milliseconds-100 seconds. In some embodiments, the first DEP field region is produced using a direct current having a pulse width of 1 second-1000 seconds. In some embodiments, the first DEP field region is produced using a direct current having a pulse width of 500 milliseconds-1 second. In some embodiments, the first DEP field region is produced using a pulse frequency of 0.01-1000 Hz. In some embodiments, the first DEP field region is produced using a pulse frequency of 0.1-100 Hz. In some embodiments, the first DEP field region is produced using a pulse frequency of 1-100 Hz. In some embodiments, the first DEP field region is produced using a pulse frequency of 100-1000 Hz.

In some embodiments, the fluid comprises a mixture of cell types. For example, blood comprises red blood cells and white blood cells. Environmental samples comprise many types of cells and other particulate material over a wide range of concentrations. In some embodiments, one cell type (or any number of cell types less than the total number of cell types comprising the sample) is preferentially concentrated in the first DEP field. Without limitation, this embodiment is beneficial for focusing the nucleic acid isolation procedure on a particular environmental contaminant, such as a fecal coliform bacterium, whereby DNA sequencing may be used to identify the source of the contaminant. In another non-limiting example, the first DEP field is operated in a manner that specifically concentrates viruses and not cells (e.g., in a fluid with conductivity of greater than 300 mS/m, viruses concentrate in a DEP high field region, while larger cells will concentrate in a DEP low field region).

In some embodiments, a method, device or system described herein is suitable for isolating or separating specific cell types. In some embodiments, the DEP field of the method, device or system is specifically tuned to allow for the separation or concentration of a specific type of cell into a field region of the DEP field. In some embodiments, a method, device or system described herein provides more than one field region wherein more than one type of cell is isolated or concentrated. In some embodiments, a method, device, or system described herein is tunable so as to allow isolation or concentration of different types of cells within the DEP field regions thereof. In some embodiments, a method provided herein further comprises tuning the DEP field. In some embodiments, a device or system provided herein is capable of having the DEP field tuned. In some instances, such tuning may be in providing a DEP particularly suited for the desired purpose. For example, modifications in the array, the energy, or another parameter are optionally utilized to tune the DEP field. Tuning parameters for finer resolution include electrode diameter, edge to edge distance between electrodes, voltage, frequency, fluid conductivity and hydrogel composition.

In some embodiments, the first DEP field region comprises the entirety of an array of electrodes. In some embodiments, the first DEP field region comprises a portion of an array of electrodes. In some embodiments, the first DEP field region comprises about 90%, about 80%, about 70%, about 60%, about 50%, about 40%, about 30%, about 25%, about 20%, or about 10% of an array of electrodes. In some embodiments, the first DEP field region comprises about a third of an array of electrodes.

Second DEP Field Region

In one aspect, following lysis of the cells (as provided below), the methods described herein involve concentrating the nucleic acid in a second DEP field region. In another aspect, the devices and systems described herein are capable of concentrating the nucleic acid in a second DEP field region. In some embodiments, the second DEP field region is any field region suitable for concentrating nucleic acids.

In some embodiments, the nucleic acids are concentrated on the array of electrodes. In some embodiments, the second DEP field region is a dielectrophoretic high field region. The second DEP field region is, optionally, the same as the first DEP field region.

In some embodiments, the second dielectrophoretic field region is produced by an alternating current. In some embodiments, the alternating current has any amperage, voltage, frequency, and the like suitable for concentrating nucleic acids. In some embodiments, the second dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the second DEP field region is produced using an alternating current having an amperage of 0.1 micro Amperes-1 Ampere. In some embodiments, the second DEP field region is produced using an alternating current having an amperage of 1 micro Amperes-1 Ampere. In some embodiments, the second DEP field region is produced using an alternating current having an amperage of 100 micro Amperes-1 Ampere. In some embodiments, the second DEP field region is produced using an alternating current having an amperage of 500 micro Amperes-500 milli Amperes. In some embodiments, the second DEP field region is produced using an alternating current having a voltage of 1-25 Volts peak to peak. In some embodiments, the second DEP field region is produced using an alternating current having a voltage of 1-10 Volts peak to peak. In some embodiments, the second DEP field region is produced using an alternating current having a voltage of 25-50 Volts peak to peak. In some embodiments, the second DEP field region is produced using a frequency of from 10-1,000,000 Hz. In some embodiments, the second DEP field region is produced using a frequency of from 100-100,000 Hz. In some embodiments, the second DEP field region is produced using a frequency of from 100-10,000 Hz. In some embodiments, the second DEP field region is produced using a frequency of from 10,000-100,000 Hz. In some embodiments, the second DEP field region is produced using a frequency of from 100,000-1,000,000 Hz.

In some embodiments, the second dielectrophoretic field region is produced by a direct current. In some embodiments, the direct current has any amperage, voltage, frequency, and the like suitable for concentrating nucleic acids. In some embodiments, the second dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the second DEP field region is produced using an alternating current having a voltage of 5-25 volts peak to peak. In some embodiments, the second DEP field region is produced using an alternating current having a frequency of from 3-15 kHz. In some embodiments, the second DEP field region is produced using an alternating current having an amperage of 1 milliamp to 1 amp. In some embodiments, the second DEP field region is produced using a direct current having an amperage of 1 micro Amperes-1 Amperes. In some embodiments, the second DEP field region is produced using a direct current having an amperage of 100 micro Amperes-500 milli Amperes. In some embodiments, the second DEP field region is produced using a direct current having an amperage of 1 milli Amperes-1 Amperes. In some embodiments, the second DEP field region is produced using a direct current having an amperage of 1 micro Amperes-1 milli Amperes. In some embodiments, the second DEP field region is produced using a direct current having a pulse width of 500 milliseconds-500 seconds. In some embodiments, the second DEP field region is produced using a direct current having a pulse width of 500 milliseconds-100 seconds. In some embodiments, the second DEP field region is produced using a direct current having a pulse width of 1 second-1000 seconds. In some embodiments, the second DEP field region is produced using a direct current having a pulse width of 500 milliseconds-1 second. In some embodiments, the second DEP field region is produced using a pulse frequency of 0.01-1000 Hz. In some embodiments, the second DEP field region is produced using a pulse frequency of 0.1-100 Hz. In some embodiments, the second DEP field region is produced using a pulse frequency of 1-100 Hz. In some embodiments, the second DEP field region is produced using a pulse frequency of 100-1000 Hz.

In some embodiments, the second DEP field region comprises the entirety of an array of electrodes. In some embodiments, the second DEP field region comprises a portion of an array of electrodes. In some embodiments, the second DEP field region comprises about 90%, about 80%, about 70%, about 60%, about 50%, about 40%, about 30%, about 25%, about 20%, or about 10% of an array of electrodes. In some embodiments, the second DEP field region comprises about a third of an array of electrodes.

Isolating Nucleic Acids

Figure 5:
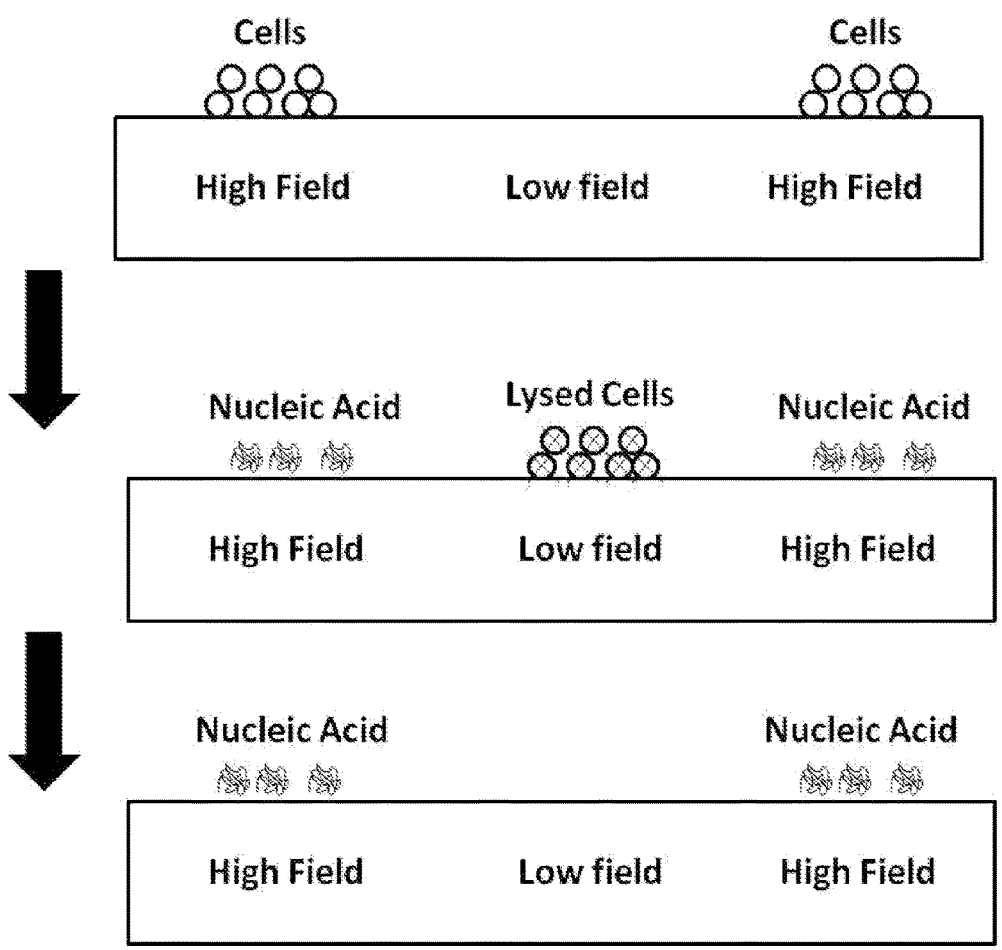
FIG. 5 shows an exemplary method for isolating nucleic acids from cells.

In one aspect, described herein is a method for isolating a nucleic acid from a fluid comprising cells. In some embodiments, the nucleic acids are initially inside the cells. As seen in FIG. 5, the method comprises concentrating the cells near a high field region in some instances. In some embodiments, disclosed herein is method for isolating a nucleic acid from a fluid comprising cells, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some instances, the cells are lysed in the high field region. Following lysis, the nucleic acids remain in the high field region and/or are concentrated in the high field region. In some instances, residual cellular material is concentrated near the low field region. In some embodiments, the residual material is washed from the device and/or washed from the nucleic acids. In some embodiments, the nucleic acid is concentrated in the second AC electrokinetic field region.

Figure 6:
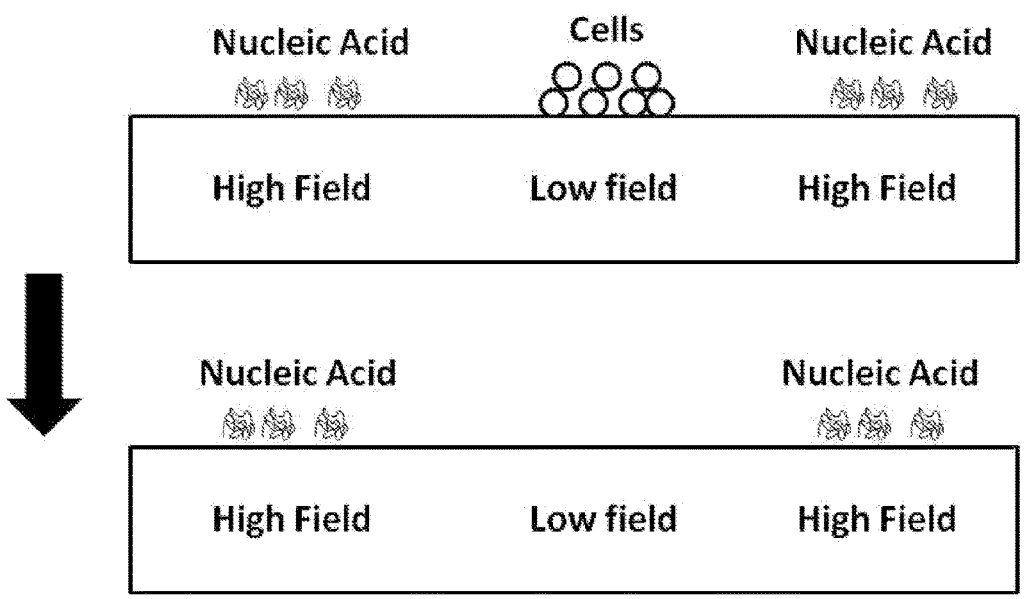
FIG. 6 shows an exemplary method for isolating extracellular nucleic acids from a fluid comprising cells.
Figure 7:
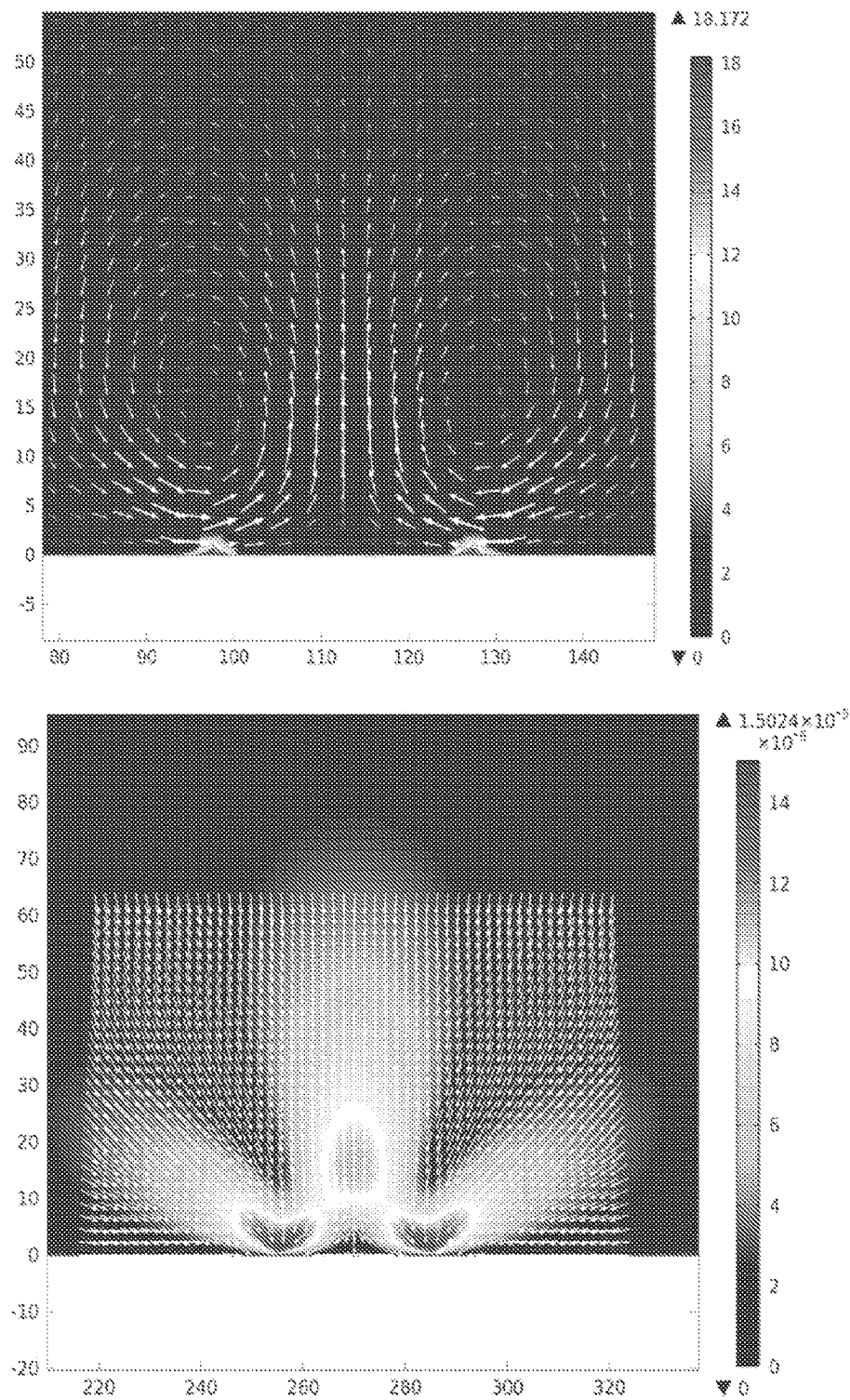
FIG. 7 exemplifies ACE (AC Electrokinetic) forces that result due to the methods and devices disclosed herein. Using the relationship between forces on particles due to Dielectrophoresis (DEP), AC Electrothermal (ACET) flow and AC Electroosmosis, (ACEO), in some embodiments, size cut-offs are used for nucleic acid isolation and purification. Isolation relies on flow vortices that will brings nucleic acids closer to an electrode edge due to ACET and ACEO depending on fluid conductivity, A DEP trap holds onto particles once they are at the trap site, depending on the effective Stokes radius.

In one aspect, described herein is a method for isolating a nucleic acid from a fluid comprising cells or other particulate material. In some embodiments, the nucleic acids are not inside the cells (e.g., cell-free DNA in fluid). In some embodiments, disclosed herein is a method for isolating a nucleic acid from a fluid comprising cells or other particulate material, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some embodiments, the method further comprises degrading residual proteins after flushing cells away. FIG. 6 shows an exemplary method for isolating extra-cellular nucleic acids from a fluid comprising cells. In some embodiments, cells are concentrated on or near a low field region and nucleic acids are concentrated on or near a high field region. In some instances, the cells are washed from the device and/or washed from the nucleic acids.

In one aspect, the methods, systems and devices described herein isolate nucleic acid from a fluid comprising cells or other particulate material. In one aspect, dielectrophoresis is used to concentrate cells. In some embodiments, the fluid is a liquid, optionally water or an aqueous solution or dispersion. In some embodiments, the fluid is any suitable fluid including a bodily fluid. Exemplary bodily fluids include whole blood, serum, plasma, bile, milk, cerebrospinal fluid, gastric juice, ejaculate, mucus, peritoneal fluid, saliva, sweat, tears, urine, and other bodily fluids. In some embodiments, nucleic acids are isolated from bodily fluids using the methods, systems or devices described herein as part of a medical therapeutic or diagnostic procedure, device or system. In some embodiments, the fluid is tissues and/or cells solubilized and/or dispersed in a fluid. For example, the tissue can be a cancerous tumor from which nucleic acid can be isolated using the methods, devices or systems described herein.

In some embodiments, the fluid is an environmental sample. In some embodiments, the environmental sample is assayed or monitored for the presence of a particular nucleic acid sequence indicative of a certain contamination, infestation incidence or the like. The environmental sample can also be used to determine the source of a certain contamination, infestation incidence or the like using the methods, devices or systems described herein. Exemplary environmental samples include municipal wastewater, industrial wastewater, water or fluid used in or produced as a result of various manufacturing processes, lakes, rivers, oceans, aquifers, ground water, storm water, plants or portions of plants, animals or portions of animals, insects, municipal water supplies, and the like.

In some embodiments, the fluid is a food or beverage. The food or beverage can be assayed or monitored for the presence of a particular nucleic acid sequence indicative of a certain contamination, infestation incidence or the like. The food or beverage can also be used to determine the source of a certain contamination, infestation incidence or the like using the methods, devices or systems described herein. In various embodiments, the methods, devices and systems described herein can be used with one or more of bodily fluids, environmental samples, and foods and beverages to monitor public health or respond to adverse public health incidences.

In some embodiments, the fluid is a growth medium. The growth medium can be any medium suitable for culturing cells, for example lysogeny broth (LB) for culturing E. coli, Ham's tissue culture medium for culturing mammalian cells, and the like. The medium can be a rich medium, minimal medium, selective medium, and the like. In some embodiments, the medium comprises or consists essentially of a plurality of clonal cells. In some embodiments, the medium comprises a mixture of at least two species.

In some embodiments, the fluid is water.

The cells are any cell suitable for isolating nucleic acids from as described herein. In various embodiments, the cells are eukaryotic or prokaryotic. In various embodiments, the cells consist essentially of a plurality of clonal cells or may comprise at least two species and/or at least two strains.

In various embodiments, the cells are pathogen cells, bacteria cells, plant cells, animal cells, insect cells, algae cells, cyanobacterial cells, organelles and/or combinations thereof. As used herein, "cells" include viruses and other intact pathogenic microorganisms. The cells can be microorganisms or cells from multi-cellular organisms. In some instances, the cells originate from a solubilized tissue sample.

In various embodiments, the cells are wild-type or genetically engineered. In some instances, the cells comprise a library of mutant cells. In some embodiments, the cells are randomly mutagenized such as having undergone chemical mutagenesis, radiation mutagenesis (e.g. UV radiation), or a combination thereof. In some embodiments, the cells have been transformed with a library of mutant nucleic acid molecules.

In some embodiments, the fluid may also comprise other particulate material. Such particulate material may be, for example, inclusion bodies (e.g., ceroids or Mallory bodies), cellular casts (e.g., granular casts, hyaline casts, cellular casts, waxy casts and pseudo casts), Pick's bodies, Lewy bodies, fibrillary tangles, fibril formations, cellular debris and other particulate material. In some embodiments, particulate material is an aggregated protein (e.g., beta-amyloid).

The fluid can have any conductivity including a high or low conductivity. In some embodiments, the conductivity is between about 1 µS/m to about 10 mS/m. In some embodiments, the conductivity is between about 10 µS/m to about 10 mS/m. In other embodiments, the conductivity is between about 50 µS/m to about 10 mS/m. In yet other embodiments, the conductivity is between about 100 µS/m to about 10 mS/m, between about 100 µS/m to about 8 mS/m, between about 100 µS/m to about 6 mS/m, between about 100 µS/m to about 5 mS/m, between about 100 µS/m to about 4 mS/m, between about 100 µS/m to about 3 mS/m, between about 100 µS/m to about 2 mS/m, or between about 100 µS/m to about 1 mS/m.

In some embodiments, the conductivity is about 1 µS/m. In some embodiments, the conductivity is about 10 µS/m. In some embodiments, the conductivity is about 100 µS/m. In some embodiments, the conductivity is about 1 mS/m. In other embodiments, the conductivity is about 2 mS/m. In some embodiments, the conductivity is about 3 mS/m. In yet other embodiments, the conductivity is about 4 mS/m. In some embodiments, the conductivity is about 5 mS/m. In some embodiments, the conductivity is about 10 mS/m. In still other embodiments, the conductivity is about 100 mS/m. In some embodiments, the conductivity is about 1 S/m. In other embodiments, the conductivity is about 10 S/m.

In some embodiments, the conductivity is at least 1 µS/m. In yet other embodiments, the conductivity is at least 10 µS/m. In some embodiments, the conductivity is at least 100 µS/m. In some embodiments, the conductivity is at least 1 mS/m. In additional embodiments, the conductivity is at least 10 mS/m. In yet other embodiments, the conductivity is at least 100 mS/m. In some embodiments, the conductivity is at least 1 S/m. In some embodiments, the conductivity is at least 10 S/m. In some embodiments, the conductivity is at most 1 µS/m. In some embodiments, the conductivity is at most 10 µS/m. In other embodiments, the conductivity is at most 100 µS/m. In some embodiments, the conductivity is at most 1 mS/m. In some embodiments, the conductivity is at most 10 mS/m. In some embodiments, the conductivity is at most 100 mS/m. In yet other embodiments, the conductivity is at most 1 S/m. In some embodiments, the conductivity is at most 10 S/m.

In some embodiments, the fluid is a small volume of liquid including less than 10 ml. In some embodiments, the fluid is less than 8 ml. In some embodiments, the fluid is less than 5 ml. In some embodiments, the fluid is less than 2 ml. In some embodiments, the fluid is less than 1 ml. In some embodiments, the fluid is less than 500 µl. In some embodiments, the fluid is less than 200 µl. In some embodiments, the fluid is less than 100 µl. In some embodiments, the fluid is less than 50 µL. In some embodiments, the fluid is less than 10 µl. In some embodiments, the fluid is less than 5 µl. In some embodiments, the fluid is less than 1 µl. In preferred embodiments, the fluid is between about 50 µl to about 500 µl.

In some embodiments, the quantity of fluid applied to the device or used in the method comprises less than about 100,000,000 cells. In some embodiments, the fluid comprises less than about 10,000,000 cells. In some embodiments, the fluid comprises less than about 1,000,000 cells. In some embodiments, the fluid comprises less than about 100,000 cells. In some embodiments, the fluid comprises less than about 10,000 cells. In some embodiments, the fluid comprises less than about 1,000 cells.

In some embodiments, isolation of nucleic acid from a fluid comprising cells or other particulate material with the devices, systems and methods described herein takes less than about 30 minutes, less than about 20 minutes, less than about 15 minutes, less than about 10 minutes, less than about 5 minutes or less than about 1 minute. In other embodiments, isolation of nucleic acid from a fluid comprising cells or other particulate material with the devices, systems and methods described herein takes not more than about 30 minutes, not more than about 20 minutes, not more than about 15 minutes, not more than about 10 minutes, not more than about 5 minutes, not more than about 2 minutes or not more than about 1 minute. In additional embodiments, isolation of nucleic acid from a fluid comprising cells or other particulate material with the devices, systems and methods described herein takes less than about 15 minutes, preferably less than about 10 minutes or less than about 5 minutes.

In some instances, extra-cellular DNA or other nucleic acid (outside cells) is isolated from a fluid comprising cells of other particulate material. In some embodiments, the fluid comprises cells. In some embodiments, the fluid does not comprise cells.

Cell Lysis

In one aspect, following concentrating the cells in a first dielectrophoretic field region, the method involves freeing nucleic acids from the cells. In another aspect, the devices and systems described herein are capable of freeing nucleic acids from the cells. In some embodiments, the nucleic acids are freed from the cells in the first DEP field region.

In some embodiments, the methods described herein free nucleic acids from a plurality of cells by lysing the cells. In some embodiments, the devices and systems described herein are capable of freeing nucleic acids from a plurality of cells by lysing the cells. One method of cell lysis involves applying a direct current to the cells after isolation of the cells on the array. The direct current has any suitable amperage, voltage, and the like suitable for lysing cells. In some embodiments, the current has a voltage of about 1 Volt to about 500 Volts. In some embodiments, the current has a voltage of about 10 Volts to about 500 Volts. In other embodiments, the current has a voltage of about 10 Volts to about 250 Volts. In still other embodiments, the current has a voltage of about 50 Volts to about 150 Volts. Voltage is generally the driver of cell lysis, as high electric fields result in failed membrane integrity.

In some embodiments, the direct current used for lysis comprises one or more pulses having any duration, frequency, and the like suitable for lysing cells. In some embodiments, a voltage of about 100 volts is applied for about 1 millisecond to lyse cells. In some embodiments, the voltage of about 100 volts is applied 2 or 3 times over the source of a second.

In some embodiments, the frequency of the direct current depends on volts/cm, pulse width, and the fluid conductivity. In some embodiments, the pulse has a frequency of about 0.001 to about 1000 Hz. In some embodiments, the pulse has a frequency from about 10 to about 200 Hz. In other embodiments, the pulse has a frequency of about 0.01 Hz-1000 Hz. In still other embodiments, the pulse has a frequency of about 0.1 Hz-1000 Hz, about 1 Hz-1000 Hz, about 1 Hz-500 Hz, about 1 Hz-400 Hz, about 1 Hz-300 Hz, or about 1 Hz-about 250 Hz. In some embodiments, the pulse has a frequency of about 0.1 Hz. In other embodiments, the pulse has a frequency of about 1 Hz. In still other embodiments, the pulse has a frequency of about 5 Hz, about 10 Hz, about 50 Hz, about 100 Hz, about 200 Hz, about 300 Hz, about 400 Hz, about 500 Hz, about 600 Hz, about 700 Hz, about 800 Hz, about 900 Hz or about 1000 Hz.

In other embodiments, the pulse has a duration of about 1 millisecond (ms)-1000 seconds (s). In some embodiments, the pulse has a duration of about 10 ms-1000 s. In still other embodiments, the pulse has a duration of about 100 ms-1000 s, about 1 s-1000 s, about 1 s-500 s, about 1 s-250 s or about 1 s-150 s. In some embodiments, the pulse has a duration of about 1 ms, about 10 ms, about 100 ms, about 1 s, about 2 s, about 3 s, about 4 s, about 5 s, about 6 s, about 7 s, about 8 s, about 9 s, about 10 s, about 20 s, about 50 s, about 100 s, about 200 s, about 300 s, about 500 s or about 1000 s. In some embodiments, the pulse has a frequency of 0.2 to 200 Hz with duty cycles from 10-50%.

In some embodiments, the direct current is applied once, or as multiple pulses. Any suitable number of pulses may be applied including about 1-20 pulses. There is any suitable amount of time between pulses including about 1 millisecond-1000 seconds. In some embodiments, the pulse duration is 0.01 to 10 seconds.

In some embodiments, the cells are lysed using other methods in combination with a direct current applied to the isolated cells. In yet other embodiments, the cells are lysed without use of direct current. In various aspects, the devices and systems are capable of lysing cells with direct current in combination with other means, or may be capable of lysing cells without the use of direct current. Any method of cell lysis known to those skilled in the art may be suitable including, but not limited to application of a chemical lysing agent (e.g., an acid), an enzymatic lysing agent, heat, pressure, shear force, sonic energy, osmotic shock, or combinations thereof. Lysozyme is an example of an enzymatic-lysing agent.

Removal of Residual Material

In some embodiments, following concentration of the nucleic acids in the second DEP field region, the method includes optionally flushing residual material from the nucleic acid. In some embodiments, the devices or systems described herein are capable of optionally and/or comprising a reservoir comprising a fluid suitable for flushing residual material from the nucleic acid. In some embodiments, the nucleic acid is held near the array of electrodes, such as in the second DEP field region, by continuing to energize the electrodes. "Residual material" is anything originally present in the fluid, originally present in the cells, added during the procedure, created through any step of the process including but not limited to lysis of the cells (i.e. residual cellular material), and the like. For example, residual material includes non-lysed cells, cell wall fragments, proteins, lipids, carbohydrates, minerals, salts, buffers, plasma, and undesired nucleic acids. In some embodiments, the lysed cellular material comprises residual protein freed from the plurality of cells upon lysis. It is possible that not all of the nucleic acid will be concentrated in the second DEP field. In some embodiments, a certain amount of nucleic acid is flushed with the residual material.

In some embodiments, the residual material is flushed in any suitable fluid, for example in water, TBE buffer, or the like. In some embodiments, the residual material is flushed with any suitable volume of fluid, flushed for any suitable period of time, flushed with more than one fluid, or any other variation. In some embodiments, the method of flushing residual material is related to the desired level of isolation of the nucleic acid, with higher purity nucleic acid requiring more stringent flushing and/or washing. In other embodiments, the method of flushing residual material is related to the particular starting material and its composition. In some instances, a starting material that is high in lipid requires a flushing procedure that involves a hydrophobic fluid suitable for solubilizing lipids.

In some embodiments, the method includes degrading residual material including residual protein. In some embodiments, the devices or systems are capable of degrading residual material including residual protein. For example, proteins are degraded by one or more of chemical degradation (e.g. acid hydrolysis) and enzymatic degradation. In some embodiments, the enzymatic degradation agent is a protease. In other embodiments, the protein degradation agent is Proteinase K. The optional step of degradation of residual material is performed for any suitable time, temperature, and the like. In some embodiments, the degraded residual material (including degraded proteins) is flushed from the nucleic acid.

In some embodiments, the agent used to degrade the residual material is inactivated or degraded. In some embodiments, the devices or systems are capable of degrading or inactivating the agent used to degrade the residual material. In some embodiments, an enzyme used to degrade the residual material is inactivated by heat (e.g., 50 to 95° C. for 5-15 minutes). For example, enzymes including proteases, (for example, Proteinase K) are degraded and/or inactivated using heat (typically, 15 minutes, 70° C.). In some embodiments wherein the residual proteins are degraded by an enzyme, the method further comprises inactivating the degrading enzyme (e.g., Proteinase K) following degradation of the proteins. In some embodiments, heat is provided by a heating module in the device (temperature range, e.g., from 30 to 95° C.).

The order and/or combination of certain steps of the method can be varied. In some embodiments, the devices or methods are capable of performing certain steps in any order or combination. For example, in some embodiments, the residual material and the degraded proteins are flushed in separate or concurrent steps. That is, the residual material is flushed, followed by degradation of residual proteins, followed by flushing degraded proteins from the nucleic acid. In some embodiments, one first degrades the residual proteins, and then flush both the residual material and degraded proteins from the nucleic acid in a combined step.

In some embodiments, the nucleic acid are retained in the device and optionally used in further procedures such as PCR or other procedures manipulating or amplifying nucleic acid. In some embodiments, the devices and systems are capable of performing PCR or other optional procedures. In other embodiments, the nucleic acids are collected and/or eluted from the device. In some embodiments, the devices and systems are capable of allowing collection and/or elution of nucleic acid from the device or system. In some embodiments, the isolated nucleic acid is collected by (i) turning off the second dielectrophoretic field region; and (ii)

eluting the nucleic acid from the array in an eluant. Exemplary eluants include water, TE, TBE and L-Histidine buffer.

Nucleic Acids and Yields Thereof

In some embodiments, the method, device, or system described herein is optionally utilized to obtain, isolate, or separate any desired nucleic acid that may be obtained from such a method, device or system. Nucleic acids isolated by the methods, devices and systems described herein include DNA (deoxyribonucleic acid), RNA (ribonucleic acid), and combinations thereof. In some embodiments, the nucleic acid is isolated in a form suitable for sequencing or further manipulation of the nucleic acid, including amplification, ligation or cloning.

In various embodiments, an isolated or separated nucleic acid is a composition comprising nucleic acid that is free from at least 99% by mass of other materials, free from at least 99% by mass of residual cellular material (e.g., from lysed cells from which the nucleic acid is obtained), free from at least 98% by mass of other materials, free from at least 98% by mass of residual cellular material, free from at least 95% by mass of other materials, free from at least 95% by mass of residual cellular material, free from at least 90% by mass of other materials, free from at least 90% by mass of residual cellular material, free from at least 80% by mass of other materials, free from at least 80% by mass of residual cellular material, free from at least 70% by mass of other materials, free from at least 70% by mass of residual cellular material, free from at least 60% by mass of other materials, free from at least 60% by mass of residual cellular material, free from at least 50% by mass of other materials, free from at least 50% by mass of residual cellular material, free from at least 30% by mass of other materials, free from at least 30% by mass of residual cellular material, free from at least 10% by mass of other materials, free from at least 10% by mass of residual cellular material, free from at least 5% by mass of other materials, or free from at least 5% by mass of residual cellular material.

In various embodiments, the nucleic acid has any suitable purity. For example, if a DNA sequencing procedure can work with nucleic acid samples having about 20% residual cellular material, then isolation of the nucleic acid to 80% is suitable. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass.

The nucleic acids are isolated in any suitable form including unmodified, derivatized, fragmented, non-fragmented, and the like. In some embodiments, the nucleic acid is collected in a form suitable for sequencing. In some embodiments, the nucleic acid is collected in a fragmented form suitable for shotgun-sequencing, amplification or other manipulation. The nucleic acid may be collected from the device in a solution comprising reagents used in, for example, a DNA sequencing procedure, such as nucleotides as used in sequencing by synthesis methods.

In some embodiments, the methods described herein result in an isolated nucleic acid sample that is approximately representative of the nucleic acid of the starting sample. In some embodiments, the devices and systems described herein are capable of isolating nucleic acid from a sample that is approximately representative of the nucleic acid of the starting sample. That is, the population of nucleic acids collected by the method, or capable of being collected by the device or system, are substantially in proportion to the population of nucleic acids present in the cells in the fluid. In some embodiments, this aspect is advantageous in applications in which the fluid is a complex mixture of many cell types and the practitioner desires a nucleic acid-based procedure for determining the relative populations of the various cell types.

In some embodiments, the nucleic acid isolated using the methods described herein or capable of being isolated by the devices described herein is high-quality and/or suitable for using directly in downstream procedures such as DNA sequencing, nucleic acid amplification, such as PCR, or other nucleic acid manipulation, such as ligation, cloning or further translation or transformation assays. In some embodiments, the collected nucleic acid comprises at most 0.01% protein. In some embodiments, the collected nucleic acid comprises at most 0.5% protein. In some embodiments, the collected nucleic acid comprises at most 0.1% protein. In some embodiments, the collected nucleic acid comprises at most 1% protein. In some embodiments, the collected nucleic acid comprises at most 2% protein. In some embodiments, the collected nucleic acid comprises at most 3% protein. In some embodiments, the collected nucleic acid comprises at most 4% protein. In some embodiments, the collected nucleic acid comprises at most 5% protein.

In some embodiments, the nucleic acid isolated by the methods described herein or capable of being isolated by the devices described herein has a concentration of at least 0.5 ng/mL. In some embodiments, the nucleic acid isolated by the methods described herein or capable of being isolated by the devices described herein has a concentration of at least 1 ng/mL. In some embodiments, the nucleic acid isolated by the methods described herein or capable of being isolated by the devices described herein has a concentration of at least 5 ng/mL. In some embodiments, the nucleic acid isolated by the methods described herein or capable of being isolated by the devices described herein has a concentration of at least 10 ng/ml.

In some embodiments, about 50 pico-grams of nucleic acid is isolated from about 5,000 cells using the methods, systems or devices described herein. In some embodiments, the methods, systems or devices described herein yield at least 10 pico-grams of nucleic acid from about 5,000 cells. In some embodiments, the methods, systems or devices described herein yield at least 20 pico-grams of nucleic acid from about 5,000 cells. In some embodiments, the methods, systems or devices described herein yield at least 50 pico-grams of nucleic acid from about 5,000 cells. In some embodiments, the methods, systems or devices described herein yield at least 75 pico-grams of nucleic acid from about 5,000 cells. In some embodiments, the methods, systems or devices described herein yield at least 100 pico-grams of nucleic acid from about 5,000 cells. In some embodiments, the methods, systems or devices described herein yield at least 200 pico-grams of nucleic acid from about 5,000 cells. In some embodiments, the methods, systems or devices described herein yield at least 300 pico-grams of nucleic acid from about 5,000 cells. In some embodiments, the methods, systems or devices described herein yield at least 400 pico-grams of nucleic acid from about 5,000 cells. In some embodiments, the methods, systems or devices described herein yield at least 500 pico-grams of nucleic acid from about 5,000 cells. In some embodiments, the methods, systems or devices described herein yield at least 1,000 pico-grams of nucleic acid from about 5,000 cells. In some embodiments, the methods, systems or devices described herein yield at least 10,000 pico-grams of nucleic acid from about 5,000 cells.

Assays and Applications

In some embodiments, the methods described herein further comprise optionally amplifying the isolated nucleic acid by polymerase chain reaction (PCR). In some embodiments, the PCR reaction is performed on or near the array of electrodes or in the device. In some embodiments, the device or system comprise a heater and/or temperature control mechanisms suitable for thermocycling.

PCR is optionally done using traditional thermocycling by placing the reaction chemistry analytes in between two efficient thermoconductive elements (e.g., aluminum or silver) and regulating the reaction temperatures using TECs. Additional designs optionally use infrared heating through optically transparent material like glass or thermo polymers. In some instances, designs use smart polymers or smart glass that comprise conductive wiring networked through the substrate. This conductive wiring enables rapid thermal conductivity of the materials and (by applying appropriate DC voltage) provides the required temperature changes and gradients to sustain efficient PCR reactions. In certain instances, heating is applied using resistive chip heaters and other resistive elements that will change temperature rapidly and proportionally to the amount of current passing through them.

In some embodiments, used in conjunction with traditional fluorometry (ccd, pmt, other optical detector, and optical filters), fold amplification is monitored in real-time or on a timed interval. In certain instances, quantification of final fold amplification is reported via optical detection converted to AFU (arbitrary fluorescence units correlated to analyze doubling) or translated to electrical signal via impedance measurement or other electrochemical sensing.

Given the small size of the micro electrode array, these elements are optionally added around the micro electrode array and the PCR reaction will be performed in the main sample processing chamber (over the DEP array) or the analytes to be amplified are optionally transported via fluidics to another chamber within the fluidic cartridge to enable on-cartridge Lab-On-Chip processing.

In some instances, light delivery schemes are utilized to provide the optical excitation and/or emission and/or detection of fold amplification. In certain embodiments, this includes using the flow cell materials (thermal polymers like acrylic (PMMA) cyclic olefin polymer (COP), cyclic olefin co-polymer, (COC), etc.) as optical wave guides to remove the need to use external components. In addition, in some instances light sources-light emitting diodes-LEDs, vertical-cavity surface-emitting lasers-VCSELs, and other lighting schemes are integrated directly inside the flow cell or built directly onto the micro electrode array surface to have internally controlled and powered light sources. Miniature PMTs, CCDs, or CMOS detectors can also be built into the flow cell. This minimization and miniaturization enables compact devices capable of rapid signal delivery and detection while reducing the footprint of similar traditional devices (i.e. a standard bench top PCR/QPCR/Fluorometer).

Amplification on Chip

In some instances, silicon microelectrode arrays can withstand thermal cycling necessary for PCR. In some applications, on-chip PCR is advantageous because small amounts of target nucleic acids can be lost during transfer steps. In certain embodiments of devices, systems or processes described herein, any one or more of multiple PCR techniques are optionally used, such techniques optionally including any one or more of the following: thermal cycling in the flowcell directly; moving the material through microchannels with different temperature zones; and moving volume into a PCR tube that can be amplified on system or transferred to a PCR machine. In some instances, droplet PCR is performed if the outlet contains a T-junction that contains an immiscible fluid and interfacial stabilizers (surfactants, etc). In certain embodiments, droplets are thermal cycled in by any suitable method.

In some embodiments, amplification is performed using an isothermal reaction, for example, transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification or circular helicase-dependent amplification.

In various embodiments, amplification is performed in homogenous solution or as heterogeneous system with anchored primer(s). In some embodiments of the latter, the resulting amplicons are directly linked to the surface for higher degree of multiplex. In some embodiments, the amplicon is denatured to render single stranded products on or near the electrodes. Hybridization reactions are then optionally performed to interrogate the genetic information, such as single nucleotide polymorphisms (SNPs), Short Tandem Repeats (STRs), mutations, insertions/deletions, methylation, etc. Methylation is optionally determined by parallel analysis where one DNA sample is bisulfite treated and one is not. Bisulfite depurinates unmodified C becoming a U. Methylated C is unaffected in some instances. In some embodiments, allele specific base extension is used to report the base of interest.

Rather than specific interactions, the surface is optionally modified with nonspecific moieties for capture. For example, surface could be modified with polycations, i.e., polylysine, to capture DNA molecules which can be released by reverse bias (−V). In some embodiments, modifications to the surface are uniform over the surface or patterned specifically for functionalizing the electrodes or non electrode regions. In certain embodiments, this is accomplished with photolithography, electrochemical activation, spotting, and the like.

In some applications, where multiple chip designs are employed, it is advantageous to have a chip sandwich where the two devices are facing each other, separated by a spacer, to form the flow cell. In various embodiments, devices are run sequentially or in parallel. For sequencing and next generation sequencing (NGS), size fragmentation and selection has ramifications on sequencing efficiency and quality. In some embodiments, multiple chip designs are used to narrow the size range of material collected creating a band pass filter. In some instances, current chip geometry (e.g., 80 urn diameter electrodes on 200 um center-center pitch (80/200) acts as 500 bp cutoff filter (e.g., using voltage and frequency conditions around 10 Vpp and 10 kHz). In such instances, a nucleic acid of greater than 500 bp is captured, and a nucleic acid of less than 500 bp is not. Alternate electrode diameter and pitch geometries have different cutoff sizes such that a combination of chips should provide a desired fragment size. In some instances, a 40 um diameter electrode on 100 um center-center pitch (40/100) has a lower cutoff threshold, whereas a 160 um diameter electrode on 400 um center-center pitch (160/400) has a higher cutoff threshold relative to the 80/200 geometry, under similar conditions. In various embodiments, geometries on a single chip or multiple chips are combined to select for a specific sized fragments or particles. For example a 600 bp cutoff chip would leave a nucleic acid of less than 600 bp in solution, then that material is optionally recaptured with a 500 bp cutoff chip (which is opposing the 600 bp chip). This leaves a nucleic acid population comprising 500-600 bp in solution. This population is then optionally amplified in the same chamber, a side chamber, or any other configuration. In some embodiments, size selection is accomplished using a single electrode geometry, wherein nucleic acid of >500 bp is isolated on the electrodes, followed by washing, followed by reduction of the ACE high field strength (change voltage, frequency, conductivity) in order to release nucleic acids of <600 bp, resulting in a supernatant nucleic acid population between 500-600 bp.

In some embodiments, the chip device is oriented vertically with a heater at the bottom edge which creates a temperature gradient column. In certain instances, the bottom is at denaturing temperature, the middle at annealing temperature, the top at extension temperature. In some instances, convection continually drives the process. In some embodiments, provided herein are methods or systems comprising an electrode design that specifically provides for electrothermal flows and acceleration of the process. In some embodiments, such design is optionally on the same device or on a separate device positioned appropriately. In some instances, active or passive cooling at the top, via fins or fans, or the like. provides a steep temperature gradient. In some instances the device or system described herein comprises, or a method described herein uses, temperature sensors on the device or in the reaction chamber monitor temperature and such sensors are optionally used to adjust temperature on a feedback basis. In some instances, such sensors are coupled with materials possessing different thermal transfer properties to create continuous and/or discontinuous gradient profiles.

In some embodiments, the amplification proceeds at a constant temperature (i.e, isothermal amplification).

In some embodiments, the methods disclosed herein further comprise sequencing the nucleic acid isolated as disclosed herein. In some embodiments, the nucleic acid is sequenced by Sanger sequencing or next generation sequencing (NGS). In some embodiments, the next generation sequencing methods include, but are not limited to, pyrosequencing, ion semiconductor sequencing, polony sequencing, sequencing by ligation, DNA nanoball sequencing, sequencing by ligation, or single molecule sequencing.

In some embodiments, the isolated nucleic acids disclosed herein are used in Sanger sequencing. In some embodiments, Sanger sequencing is performed within the same device as the nucleic acid isolation (Lab-on-Chip). Lab-on-Chip workflow for sample prep and Sanger sequencing results would incorporate the following steps: a) sample extraction using ACE chips; b) performing amplification of target sequences on chip; c) capture PCR products by ACE; d) perform cycle sequencing to enrich target strand; e) capture enriched target strands; f) perform Sanger chain termination reactions; perform electrophoretic separation of target sequences by capillary electrophoresis with on chip multi-color fluorescence detection. Washing nucleic acids, adding reagent, and turning off voltage is performed as necessary. Reactions can be performed on a single chip with plurality of capture zones or on separate chips and/or reaction chambers.

In some embodiments, the method disclosed herein further comprise performing a reaction on the nucleic acids (e.g., fragmentation, restriction digestion, ligation of DNA or RNA). In some embodiments, the reaction occurs on or near the array or in a device, as disclosed herein.

Other Assays

The isolated nucleic acids disclosed herein may be further utilized in a variety of assay formats. For instance, devices which are addressed with nucleic acid probes or amplicons may be utilized in dot blot or reverse dot blot analyses, base-stacking single nucleotide polymorphism (SNP) analysis, SNP analysis with electronic stringency, or in STR analysis. In addition, such devices disclosed herein may be utilized in formats for enzymatic nucleic acid modification, or protein-nucleic acid interaction, such as, e.g., gene expression analysis with enzymatic reporting, anchored nucleic acid amplification, or other nucleic acid modifications suitable for solid-phase formats including restriction endonuclease cleavage, endo- or exo-nuclease cleavage, minor groove binding protein assays, terminal transferase reactions, polynucleotide kinase or phosphatase reactions, ligase reactions, topoisomerase reactions, and other nucleic acid binding or modifying protein reactions.

In addition, the devices disclosed herein can be useful in immunoassays. For instance, in some embodiments, locations of the devices can be linked with antigens (e.g., peptides, proteins, carbohydrates, lipids, proteoglycans, glycoproteins, etc.) in order to assay for antibodies in a bodily fluid sample by sandwich assay, competitive assay, or other formats. Alternatively, the locations of the device may be addressed with antibodies, in order to detect antigens in a sample by sandwich assay, competitive assay, or other assay formats. As the isoelectric point of antibodies and proteins can be determined fairly easily by experimentation or pH/charge computations, the electronic addressing and electronic concentration advantages of the devices may be utilized by simply adjusting the pH of the buffer so that the addressed or analyte species will be charged.

In some embodiments, the isolated nucleic acids are useful for use in immunoassay-type arrays or nucleic acid arrays.

Exemplary Comparison

Approximately 100 ng of input *E. coli* genome is necessary for conventional manual methods, (e.g., 50 ng of input DNA is required for Nextera, assuming 50% recovery (Epicentre WaterMaster kit claims recovery about 30-60%) from DNA extraction purification). This is equivalent to about 20 million bacteria. In some embodiments of the present invention, less than 10,000 bacteria input is sufficient (e.g., since the chip is self contained and involves less transfers the efficiency is higher). In some embodiments, this is at least a 100 fold reduction in input, which can be important for applications where sample is limited, such as tumor biopsies.

Table 1 below outlines exemplary steps involved to go from *E. coli* to DNA suitable for sequencing. In some instances, conventional methods require centrifugation, several temperatures, wash steps, and numerous transfer steps which are inefficient. In contrast, as described herein, in some embodiments allows the same steps to be carried out by a device that minimizes the pipette transfers and exposure to large virgin surfaces with varying degrees of nonspecific binding properties. In some instances, the device is temperature controlled to provide appropriate reaction conditions. In some instances, PCR, cycle PCR for sequencing pre-amp or full PCR (endpoint, real time or digital) is accomplished off-device or on-device. Off-device includes not on the device but on the same cartridge assembly, connections via fluidic channels or conduits. Furthermore, in some instances PCR amplification is accomplished in the device flow cell chamber, in a PCR tube that is on the cartridge, or though fluidic channels that possess heat zones for temperature cycling. In some instances, the eluate from the device chamber is combined with side channel(s) primed with non aqueous miscible fluid, e.g., oil, and other droplet stabilizers to perform amplification in droplets. In some embodiments, the temperature cycling mechanics are as described above.

In Table 1, the amount of starting material for the conventional processing was 2-5×10$^7$ E. Coli cells in approximately 1 ml of water and the entire amount was concentrated on the filters. Using the chip, as disclosed herein, only 1×10$^4$ E. Coli cells in approximately 50 microliters was applied to the flow cell. This was 3 orders of magnitude less starting material.

TABLE 1

Comparison of methods for nucleic acid isolation.

| Conventional | An exemplary embodiment provided herein |
|---|---|
| Epicentre WaterMaster DNA Purification Kit | [ON CHIP] |
| Concentrate E. coli bacteria on filters | Capture E. coli, 1 MHz, 10 Vpp, 10' |
| Lysis solution | Electro-lyse E. coli, 200 V DC, 1 msec pulse |
| Proteinase K treatment, 65 C., 15' | De-energize electrodes |
| RNase treatment, 37 C., 30' | Collection, 10 Vpp, 10 KHz |
| Precipitate protein by centrifuge, 10K × g, 4 C., 10' | De-energize electrodes |
| Wash isopropanol | Q protease treatment, 37 C., 10' |
| Precipitate protein by centrifuge, 10K × g, 4 C., 10' | Inactivate 70 C., 10' |
| Rinse pellet with 70 ethanol | Collection, 10 Vpp, 10 KHz |
| Resuspend DNA in TE buffer Remove inhibitors, 2K × g, 2' Repeat 2X | Wash with Nextera LMW buffer |
| DNA ready for library prep Epicentre Nextera DNA Sample Prep (Illumina) 50 ng input DNA (1e7 E. coli equiv.) | |
| Fragment with Transposase, 55 C., 5' | Fragment with Transposase, 55 C., 7' |
| Purify with Zymo spin column, 10K × g, 1' | Elute DNA into microtube |
| Add adapters, cycle PCR, 9 cycles | [OFF CHIP] |
| Purify with Zymo spin column, 10K × g, 1' | Add adapters, cycle PCR, 9 cycles Purify with Zymo spin column, 10K × g, 1' |
| Sequence | Sequence |

In various embodiments (i.e., depending on the AC electrokinetic parameters), cells or other micron scale particles are concentrated to either the low or high field regions. In some instances, the crossover frequency which determines whether a particle moves into or away from the high field region can be tuned by varying the AC frequency, voltage, medium conductivity, adulterating particle polarizability (such as attachment or binding of materials with different DEP characteristics), or electrode geometry. In some instances, nanoscale particles are limited to concentration in the high field region. In some instances, Brownian motion and other hydrodynamic forces limit ability to concentrate in low field regions.

Detection and Characterization of Cancer Using Cell Free Biomarkers

Assays may be performed on circulating cell-free high molecular weight DNA (>300 bp) and other target cell-free biomarkers isolated using the methods and devices disclosed herein to characterize cancer in patients using target specific cell-free biomarkers. "Characterization" of cancer includes but is not limited to detection and diagnosis of cancer, prognosis of disease, treatment response monitoring and other actions related to cancer analysis and treatment therein.

In some embodiments, the characterization may be performed via molecular profiling of cell free biomarkers. The profiling includes but is not limited to enumeration of analytes, specific detection of analytes, including but not limited to proteins, lipids, antibodies, tumor DNA, tumor cells, exosomes, nucleosomes, nanosomes detection of specific gene sequences, detection of mutant gene sequences, detection of loss of heterozygosity, determination of methylation status, detection of alterations, detection of deletions and other molecular profiling assays used in the analysis and characterization of physical and/or biochemical status of a patient or subject.

Cell free biomarkers can be derived from proteins or molecules associated with cellular exocytosis, necrosis, or secretion processes. Markers include: high molecular weight dna (>500 bp), nucleosomes, exosomes, aggregated proteins, cell membrane fragments, mitochondria, cellular vesicles, and other markers related to cellular exocytosis, necrosis or secretion.

Examples of candidates for circulating cell-free biomarkers include but are not limited to circulating tumor DNA, including mutations or deletions, rearrangement, methylated nucleic acid, loss of heterozygosity, and other DNA alterations. RNA may also be used, including micro RNA (miRNA), RNA from microvesicles and other RNA forms that provide useful information with regards to the characterization of, for example, cancer diagnosis, prognosis and treatment response in a patient. Tumor cells may also be directly monitored, as well as cell free proteins, including but not limited to GFAP, VEGF, EGFR, b-FGF, KRAS, YKL-40 and MMP-9.

The methods and devices disclosed herein for characterization of, for example, cancer patients and subjects uses AC Electrokinetics to isolate cell free target biomarkers directly from whole blood, serum, plasma, or other bodily fluid or sample. The methods and devices disclosed herein uses minimal amounts of sample, for example, up to 10 μl, up to 20 μl, up to 30 μl, up to 40 μl, up to 50 μl, up to 60 μl, up to 70 μl, up to 80 μl, up to 90 μl, up to 100 μl, up to 200 μl, up to 300 μl, up to 400 μl, up to 500 μl or more of sample. In some embodiments, the methods and devices disclosed herein uses less than 500 μl, less than 400 μl, less than 300 μl, less than 200 μl, less than 100 μl, less than 90 μl, less than 80 μl, less than 70 μl, less 60 μl, less than 50 μl, less than 40 μl, less than 30 μl, less than 20 μl, less than 10 μl or less than 5 μl of sample. In some embodiments, the methods and devices disclosed herein use between about 50 μl of sample and about 500 μl of sample.

The methods and devices disclosed herein for characterization of, for example, cancer patients and subjects may use intercalating dyes, antibody labeling, or other traditional staining techniques to enable direct quantification using fluorescence microscopy or other detection techniques. The methods and devices disclosed herein may also use DNA/RNA hybridization techniques to detect specific alleles implicated in cancer. The methods and devices disclosed herein may also use Quantitative Real Time PCR, including of nuclear or mitochondrial DNA or other target nucleic acid molecule markers, enzyme-linked immunosorbent assays (ELISA), direct SYBR gold assays, direct PicoGreen assays, loss of heterozygosity (LOH) of microsatellite markers, optionally followed by electrophoresis analysis, including but not limited to capillary electrophoresis analysis, sequencing and/or cloning, including next generation sequencing, methylation analysis, including but not limited to modified semi-nested or nested methylation specific PCR, DNA specific PCR (MSP), quantification of minute amounts of DNA after bisulfitome amplification (qMAMBRA), as well as methylation on beads, mass-based analysis, including but not limited to MALDI-ToF (matrix-assisted laser desorption/ionization time of flight analysis, optionally in combination with PCR, and digital PCR.

The methods and devices disclosed herein may employ dyes, including intercalating dyes, antibody labeling, stains and other imaging molecules that enable direct quantification of the cell-free biomarker materials directly on or in use with the embodied devices, including the use of fluorescence microscopy. Examples of fluorescent labeling of nucleic acids, e.g. DNA and RNA, include but are not limited to cyanine dimers high-affinity stains (Life Technologies) can used. Among them YOYO®-1, YOYO®-3, POPO™-1, POPO™-3, TOTO®-1, TOTO®-3 are the preferred staining dyes. Fluorescent labeling of protein for detection and quantitation in conjunction with the methods and devices disclosed herein include but not limited to Quanti-iT™ protein quantitation assay, NanoOrange™ protein quantitation assay, CBQCA protein quantitation assay (Life Technologies). Fluorescent quantitation of other cancer biomarkers may also be used including mitochondria, labelling dyes such as MitoTracker® Green FM® and MitoTracker® Red FM®.

The methods and devices disclosed herein may also be used in conjunction with DNA/RNA hybridization techniques to detect specific alleles implicated in cancer. In some embodiments, specific electrodes and corresponding electrode trace lines can be designed to individually control separate electrode so as to achieve a unique electric field distribution. By designing nonuniform electric field distribution, specific DNA/RNA can be manipulated.

Additionally, the microelectrode arrays disclosed herein may be further functionalized, for example, by covering the array with a reactive hydrogel. The hydrogel may comprise binding partners, including biotin binding protein; alternatively, the hydrogel may also be functionalized by acylation or by surface modification to chemisorb oligonucleotides on the surface. The methods and devices disclosed herein may further be manipulated to attain control of hybridization and detection of specific alleles, for example, through the use of a Complimentary Metal-Oxide Semiconductor (CMOS) device that can control the microelectrode array in a manner that allows for multiple use of the array and high-throughput screening of matching oligonucleotides.

The methods and devices disclosed herein are also capable of eluting circulating cell-free target biomarkers such as nucleosomes, high molecular weight DNA, exosomes and proteins for post-genetic analysis and for quantification and further analysis using quantitative PCR, reverse transcriptase (RT) PCR, and sequencing analytical techniques for identifying proteins or nucleic acids of interest in the isolated and eluted sample DNA. Post-genetic analysis is performed on nucleosomal or nucleoprotein complexed dsDNA (greater than 300 bp), on exosomal dsDNA or RNA (greater than 100 bp), and/or on mitochondrial DNA.

Candidates of cell-free biomarkers (ccfDNA=circulating cell-free DNA) for detecting cancer using the methods and devices disclosed herein include the following:

| Cancer Type | Cancer Subtype | Genetic Alterations in ccfDNA | References/Reviews |
|---|---|---|---|
| CNS Tumors | Neuroblastoma | Oncogene MYCN detected in ccfDNA was associated with rapid tumor progression and poor outcome independent of the stage of the tumor. Hypermethylation of the DCR2 promoter predicting prognosis, therapeutic efficacy and reoccurrence | 2002 Jul. 1; 62(13): 3646-8. Misawa A et al. Br J Cancer. 2009 Jan. 27; 100(2): 399-404. |
|  | Gliomas | Gene promoter methylation p16/INK4a, MGMT, p73, RARβ and LOH in chromosomes 1p, 19q, and 10q are increased and could be detected in the tumor site and in plasma with high specificity and moderate sensitivity. EGFRvIII, a mutant of EGFR, in ccfDNA predicting prognosis. Higher frequency of RASSF1A hypermethylation differentiating primary from metastatic brain cancers | Weaver K D et al. Cancer Invest. 2006; 24: 35-40. Lavon I et al. Neuro Oncol. 2010 February; 12(2): 173-80. Salkeni M. A. J. Neurooncol. 2013. Majchrzak-Celińska A. J Appl Genet. 2013 August; 54(3): 335-44. |
|  | Breast Cancer | Levels of CCFDNA has been associated with tumor size, tumor stage, tumor grade, lymph node involvement, | Catarino R. DNA Cell Biol. 2008 August; 27(8): 415-21. Hashad D. J Clin Lab Anal. 2012 November; 26(6): 467-72. |

| Cancer Type | Cancer Subtype | Genetic Alterations in ccfDNA | References/Reviews |
|---|---|---|---|
| | | Her2/neu and topoisomerase IIα expression<br>LOH of circulating DNA (short DNA fragment) at the markers D3S1605, D10S1765, D12S1725, D13S218, D17S855, and D12S1725 that has been correlated with shorter survival.<br>Amplified HER2 in CCFDNA in patients with HER2-positive breast cancer.<br>DNA from serum correlated with progression and regional lymph nodes metastases and copy number of LINE1 (Long Interspersed Nuclear Element-1) from circulating DNA was correlated with tumor size.<br>Concurrent ERβ and RARβ2 methylation as well as loss of ERβ expression was associated with invasive ductal breast cancer and may serve as good prognostic markers.<br>CST6, APC, and RASSF1A as prognostic markers<br>Methylated RASSF1A, cyclin D2, and RARβ2 genes in CCFDNA detected in 95% of breast cancer patients.<br>Aberrant hypermethylation of p16 (associated with elevated serum level of CEA) and CDH1 (E-cadherin or CD324, a tumor suppressor gene) found in the plasma of 82% of breast cancer patients.<br>Methylation patterns in ccfDNA changed after surgery, tamoxifen treatment, and after combined treatments.<br>Different BRCA1 methylation and kinetics of plasma DNA (ALU115) in responsive and non-responsive groups.<br>hTERT (Telomerase Reverse Transcriptase in human) levels were significantly different in the estrogen receptor (ER)(+)/progesterone receptor (PgK)(+) patients compared to the ER(−)/PgR(−) patients.<br>Significant positive correlation between VEGF and cell-free serum DNA | Hashad D. J Clin Lab Anal. 2012 November; 26(6): 467-72.<br>Schwarzenbach H. Clin Cancer Res. 2012 Oct. 15; 18(20): 5719-30.<br>Weiss L. N Engl J Med. 2013 Jul. 4; 369(1): 93.<br>Page K. Br J Cancer. 2011 Apr. 12; 104(8): 1342-8.<br>Jin D. J. Mol. Biomarkers Diagn. 2012: S2-009.<br>Shaw J A. Genome Res. 2012 February; 22(2): 220-31.<br>Umetani N. J Clin Oncol. 2006 Sep. 10; 24(26): 4270-6.<br>Mirza S. Ann Surg Oncol. 2012 September; 19(9): 3107-15.<br>Müller H. M. Cancer Res. 2003; 63: 7641-7645.<br>Mirza S. Ann Surg Oncol. 2012 September; 19(9): 3107-15.<br>Zurita M. BMC Cancer. 2010 May 20; 10( ): 217.<br>Deligezer U. Ann NY Acad Sci. 2008 August; 1137( ): 175-9.<br>Liggett T E. Int J Cancer. 2011 Jan. 15; 128(2): 492-9.<br>Sharma G. Tumour Biol. 2012 December; 33(6): 1837-43.<br>Sharma G. Tumour Biol. 2012 December; 33(6): 1837-43.<br>El Tarhouny S. Cytokine. 2008 October; 44(1): 65-9.<br>El Tarhouny S. Cytokine. 2008 October; 44(1): 65-9.<br>Dawson S J. N Engl J Med. 2013 Mar. 28; 368(13): 1199-209. |
| Female Gynecological System | Endometrial Tumors | ccfDNA as a possible prognostic biomarker<br>DNA integrity (longer DNA fragments) associated with endometrial carcinoma<br>High levels of CCFDNA detected in patients with endometriosis | Tanaka H. Int J Gynecol Cancer. 2012 January; 22(1): 82-6.<br>Zachariah R. Reprod Biomed Online. 2009 March; 18(3): 407-11.<br>Dobrzycka B. Int J Cancer. 2010 Aug. 1; 127(3): 612-21. |

| Cancer Type | Cancer Subtype | Genetic Alterations in ccfDNA | References/Reviews |
|---|---|---|---|
| | Cervical Tumors | Association between CCFDNA and p53-Antibody as potential marker in predicting prognosis Plasma DNA levels related with malignant transformation and development of cervical cancer. MYOD1 promoter hypermethylation in serum as potential prognostic marker for discriminating cervical cancer patients at high risk for lymph node metastasis or relapse. Unmethylated CDH1/CDH13 in serum associated with better disease-free survival | Müller H. M. Cancer Res. 2003; 63: 7641-7645. Guan T. 2008 August; 28(9): 1663-4, 1667. Widschwendter A. Int J Cancer. 2004 Mar. 20; 109(2): 163-6. |
| | Ovarian Tumors | Higher amounts of plasma CCFDNA and circulating cell-free mitochondrial DNA (CCFMDNA) compared with healthy controls Hypermethylation of RASSF1A wasfrequently encountered in stage III and IV other than stage I and II tumors. The presence of KRAS mutations in mucinous ovarian cancer along with CCFDNA and p53-antibody in serous tumors was correlated with the highest risk of cancer progression. | Zachariah R. R. Gynecol. 2008; 112: 843-850. Ma L. Zhonghua Bing Li Xue Za Zhi. 2005 December; 34(12): 785-7. Dobrzycka B. Ann Oncol. 2011 May; 22(5): 1133-40. Kuhlmann J D. BMC Cancer. 2012 Jul. 31; 12( ): 325. |
| Hepatocellular Carcinoma (HCC) | | High levels of plasma ccfDNA have been detected in HCC and liver cirrhosis and are closely correlated with tumor size and degree of differentiation. Levels of serum LINE-1 hypomethylation are correlated significantly with the presence of HBsAg, large tumor sizes, and advanced tumor stages. Elevated levels of circulating cell-free DNA and and inflammation status in the blood of patients with hepatitis C virus-associated hepatocellular carcinoma. Mutation in TP53 at codon 249 (Ser-249, considered a hallmark of mutagenesis by aflatoxin) and in CTNNB1 (gene encoding beta-catenin) in CCFDNA may suggest a role of aflatoxin in hepatocarcinogenesis Hypermethylation of RASSF1A sequences were detected in the sera of 93% of HCC patients, 58% of HBV carriers, and 8% of the healthy volunteers. Aberrant methylation of p16 was detected in the plasma/serum samples of 81% of HCC. | Ren N. World J Gastroenterol. 2006 Jun. 28; 12(24): 3911-4. Tangkijvanich P. Clin Chim Acta. 2007 April; 379(1-2): 127-33. Iizuka N. Anticancer Res. 2006 November-December; 26(6C): 4713-9. Iida M. Oncol Rep. 2008 October; 20(4): 761-5. Hosny G. Cancer Lett. 2008 Jun. 18; 264(2): 201-8. Hosny G. Cancer Lett. 2008 Jun. 18; 264(2): 201-8. Pang J Z. Zhonghua Yi Xue Za Zhi. 2006 Jun. 27; 86(24): 1662-5. Chan K C. Clin Chem. 2008 September; 54(9): 1528-36. Zhou J. Semin Oncol. 2012 August; 39(4): 440-8. |

| Cancer Type | Cancer Subtype | Genetic Alterations in ccfDNA | References/Reviews |
|---|---|---|---|
| | | Patients with higher RASSF1A concentrations at diagnosis or one year after tumor resection showed poorer disease-free survival. The circulating concentration of RASSF1A in HBV carriers increased significantly from the time of enrollment to cancer diagnosis Microsatellite instability and loss of heterozygosity of D8S277, D8S298, and D8S1771 at chromosome 8p were detected on the plasma DNA of HCC patients. | |
| Pancreatic Carcinoma | | Methylation profile of circulating plasma DNA in patients with pancreatic cancer. Free serum DNA is an early predictor of severity in acute pancreatitis. Differential methylation of cell-free circulating DNA among patients with pancreatic cancer versus chronic pancreatitis. | Melnikov A A. J Surg Oncol. 2009 Feb. 1; 99(2): 119-22. Gornik I. Clin Biochem. 2009 January; 42(1-2): 38-43. Sawabu N. Pancreas. 2004 April; 28(3): 263-7. Liggett T. Cancer. 2010 Apr. 1; 116(7): 1674-80. |
| Gastro-intestinal Tract | Esophageal Tumors | Quantification of circulating plasma DNA revealed that up to 61% of patients with esophageal carcinoma have detectable levels of methylated DAPK (Death-associated protein kinase) or APC (adenomatous polyposis coli gene) promoter DNA and are associated with unfavorable prognosis | Tomita H. Anticancer Res. 2007 July-August; 27(4C): 2737-41. Hoffmann A C. J Cancer Res Clin Oncol. 2009 September; 135(9): 1231-7. |
| | Stoch Tumors | Plasma DNA concentration is higher in patients with gastric cancer compared with controls. Epigenetic changes of cell-free serum DNA of RUNX3, MGMT, p15, and hMLH1 hypermethylation in postoperative monitoring. methylation status of CEA, P16, E-cadherin, RARbeta and CDH4 genes | Kolesnikova E V. Ann NY Acad Sci. 2008 August; 1137( ): 226-31. Tani N. 2006; 33: 1720-1722. Sai S. Anticancer Res. 2007 July-August; 27(4C): 2747-51. Sakakura C. Anticancer Res. 2009 July; 29(7): 2619-25. |
| | Colorectal Tumors | More than half of the patients with early stage disease contain mutant DNA in their circulation. Mutated circulating DNA may depend on tumor clonality Aberrant methylation status of specific genes such as SEPT9, HPP1 and/or HLTF in the serum of patients with colorectal cancer has the potential to become a pre-therapeutic predictor of outcome. Studies have suggested that the emergence of KRAS mutant clones can be detected non-invasively months before radiographic progression and can be used for monitoring of drug resistance. | Schwarzenbach H. Ann NY Acad Sci. 2008 August; 1137( ): 190-6. da Silva Filho B F. J Clin Pathol. 2013 September; 66(9): 775-8. Lofton-Day C. Clin. Chem. 2008; 54: 414-423. Tóth K. Orv Hetil. 2009 May 24; 150(21): 969-77. deVos T. Orv Hetil. 2009 May 24; 150(21): 969-77. deVos T. Clin Chem. 2009 July; 55(7): 1337-46. Wallner M. Clin Cancer Res. 2006 Dec. 15; 12(24): 7347-52. Misale S. Nature. 2012 Jun. 28; 486(7404): 532-6. Trevisiol C. Int J Biol Markers. 2006 October-December; 21(4): 223-8. Umetani N. Clin Chem. 2006 June; 52(6): 1062-9. Morgan S R. J Clin Pathol. 2013 September; 66(9): 775-8. |

| Cancer Type | Cancer Subtype | Genetic Alterations in ccfDNA | References/Reviews |
|---|---|---|---|
| | | Serum DNA integrity increased in CRC in localized lesions and in advanced stage cancer. Early stage detection of tumor increased when CCFDNA was used in combination with CEA measurement. Other mutations include microsatellite instability, BRAF, and SMAD4 and abnormal promoter methylation including TMEFF2, NGFR, and p16 have been detected in ccfDNA. | Mouliere F. Transl Oncol. 2013 June; 6(3): 319-28. Trevisiol C. Int J Biol Markers. 2006 October-December; 21(4): 223-8. Nakayama G. Anticancer Res. 2007; 27: 1459-1463. |
| Head and Neck Tumors | Nasopharyngeal Carcinoma | Aberrant hypermethylated promoter DNA of at least one of the five following genes; CDH1, p16, DAPK1, p15, and RASSF1A was detectable in 71% of plasma of NPC patients before treatment. Hypermethylation of the promoter DNA of at least one in three genes (CDH1, DAPK1, and p16) was detectable in the post-treatment plasma of 38% of recurrent NPC patients and none of the patients in remission. EBV-DNA as a sensitive and specific marker in monitoring NPC by detecting early recurrence and correlation with treatment response. | Chan K C. Clin Cancer Res. 2008 Jul. 1; 14(13): 4141-5. Jiang W W. Int J Cancer. 2006 Dec. 1; 119(11): 2673-6. Chan S L. BMC Cancer. 2006 Oct. 31; 6( ): 259. Chan K C. Semin Cancer Biol. 2002 December; 12(6): 489-96. |
| | Thyroid Tumors | Detection of free circulating mutant BRAF/DNA in patients with papillary thyroid carcinoma (PTC) | Chuang T C. ead Neck. 2010 February; 32(2): 229-34. |
| Lymphoma/ Leukemia | | Higher levels of CCFDNA in patients with Hodgkin lymphoma (HL), diffuse large B cell Lymphoma (DLBCL), and mantle cell lymphoma than in healthy individuals and were associated with advanced stage disease, presence of B-symptoms, elevated lactate dehydrogenase levels, and age >60 years. Rearranged immunoglobulin heavy chain DNA has been found in the plasma of patients with non-Hodgkin's lymphoma and acute B cell leukemia. MGMT promoter hypermethylation along with p53 mutation as useful prognostic markers in diffuse large B cell Lymphoma (DLBCL). | Hohaus S. Ann Oncol. 2009 August; 20(8): 1408-13. Jiang Y. 2012 February; 20(1): 53-6. |
| Lung Cancer | Non Small Cell Lung Carcinoma (NSCLC) | Plasma DNA levels are increased in lung cancer patients compared to normal healthy controls and higher concentration has been associated with poor prognosis. | Cheng C. Cancer Sci. 2009 February; 100(2): 303-9. Xie G S. Chin. Med. J. 2004; 117: 1485-1488. Yoon K A. J Mol Diagn. 2009 May; 11(3): 182-5. Lee S M. Mol Cells. |

| Cancer Type | Cancer Subtype | Genetic Alterations in ccfDNA | References/Reviews |
|---|---|---|---|
| | | Complete or partial post treatment response to chemotherapy also correlates with no mutation detection. Methylation status of 14-3-3 sigma of serum DNA in pretreatment condition and for P16M in pleural lavage were associated with survival. Hypermethylation of RASSF1A, p14 (ARF) and APC are useful prognostic markers in patients receiving gemcitabine, and testing plasma DNA for K-RAS mutation is helpful in monitoring NSCLC patients receiving paclitaxel and carboplatin. Detection of epidermal growth factor receptor (EGFR) mutations using plasma DNA as essential to determine appropriate lung cancer treatment and monitoring | 2012 August; 34(2): 171-6. Ponomaryova A A. Lung Cancer. 2013 September; 81(3): 397-403. Nakamura T. J Thorac Oncol. 2012 September; 7(9): 1369-81. |
| | Small Cell Lung Carcinoma (SCLC) | Microsatellite markers or LOH are useful for the detection of alterations in the plasma DNA of SCLC patients. | Board R E. Ann. N.Y. Acad. Sci. 2008; 1137: 98-107. Tamkovich S N. Ann NY Acad Sci. 2008 August; 1137( ): 214-7. |
| Male Genital Tract | Testicular Tumors | Increased CCFDNA and cell-free serum mtDNA (79-bp (mtDNA-79) and 220 bp (mtDNA-220)) levels levels in testicular tumors and correlation with tumor stage. Hypermethylation of CCFDNA APC, GSTP1, PTGS2, p14 (ARF), p16 (INK) and RASSF1A as potential biomarkers for detection and monitoring | Ellinger J. J Urol. 2009 January; 181(1): 363-71. Ellinger J. J Urol. 2009 July; 182(1): 324-9. |
| Urinary System | Kidney Tumors | Tumor DNA from renal cell carcinoma, bladder cancer, or prostate cancer could be detectable in more than 50% of plasma/serum and in more than 70% of urine samples Promoter hypermethylation of ccfDNA for VHL, p16/CDKN2a, p14ARF, APC, RASSF1A, and Timp-3 detected with 88% sensitivity and almost 100% specificity. | Goessl C. Eur Urol. 2002 June; 41(6): 668-76. Cairns P. Ann NY Acad Sci. 2004 June; 1022( ): 40-3. |
| | Prostate Carcinoma (PCa) | CCFDNA and PSA assay gave 89% sensitivity in detecting PCa Combination of DNA load and promoter methylation status identified 88% of PCa. LOH and genetic aberrations such as allelic imbalance (AI) and epigenetic changes of promoter hypermethylation (methylation of RASSF1, RARB2, and GSTP1) have also been detected in CCFDNA of prostate cancer patients | Delgado P O. Tumour Biol. 2013 April; 34(2): 983-6. Chun F K. BJU Int. 2006 September; 98(3): 544-8. Papadopoulou E. Ann NY Acad Sci. 2006 September; 1075( ): 235-43. Müller I. Clin Chem. 2008 April; 54(4): 688-96. Ellinger J. Int J Cancer. 2008 Jan. 1; 122(1): 138-43. Cortese R. Hum Mol Genet. 2012 Aug. 15; 21(16): 3619-31. |

-continued

| Cancer Type | Cancer Subtype | Genetic Alterations in ccfDNA | References/Reviews |
|---|---|---|---|
| | | Significant associations between LOH and increasing Gleason scores for the marker combinations of D6S1631, D8S286, D9S171, D8S286 and D9S171. Methylation of the GSTP1 gene found in 25% of free plasma DNA and in 94% of tissue samples. Concentrations of apoptotic PTGS2 fragments discriminate sensitivity (88%) and specificity (64%) between BPH (benign prostate hypertrophy) and PCa but the apoptotic index (AI) was more specific (82%) but less sensitive (70%) | |
| Skin | Malignant Melanoma | Higher levels of CCFDNA in patients compared to controls and can be helpful in monitoring the disease in late stage (stage IV) but unsatisfactory for the early detection of melanoma LOH at microsatellite markers D1S243, D6S311, D9S161 and D19S246 in the plasma is also associated with malignant mucosal melanoma (MMM) and it could be useful marker for diagnosis of recurrence and metastasis MMM Detection of TFPI2-methylated DNA in the serum of patients with resected melanoma as a sensitive and specific biomarker of recurrence or metastatic melanoma | Daniotti M. Int J Cancer. 2007 Jun. 1; 120(11): 2439-44. Nakamoto D. Bull Tokyo Dent Coll. 2008 May; 49(2): 77-87. Lo Nigro C. J Invest Dermatol. 2013 May; 133(5): 1278-85. |
| | Squamous Cell Carcinoma | In 90% of squamous cell carcinomas of the oral cavity, there is a microsatellite alteration in serum DNA that is identical to those in the corresponding tumor DNA which may provide valuable prognostic information and serve as a guide for future therapy. | Kakimoto Y. Oncol Rep. 2008 November; 20(5): 1195-200. |

Additional References include: Holdhoff et al. *J. Neurooncol.* 2013, 113, 345; Elshimali et al. *Int. J. Mol. Sci.* 2013, 14, 18925; Swanson et al. *Senson Actuat. B-Chem.* 2000, 64, 22; Sosnowski et al. *Proc. Natl. Acad. Sci. U.S.* 1997, 94, 1119; Huang et al. *Macromolecules* 2002, 35, 1175; and Hofman et al. *RSC Advances* 2012, 2, 3885.

Definitions and Abbreviations

The articles "a", "an" and "the" are non-limiting. For example, "the method" includes the broadest definition of the meaning of the phrase, which can be more than one method.

"Vp-p" is the peak-to-peak voltage.

"TBE" is a buffer solution containing a mixture of Tris base, boric acid and EDTA.

"TE" is a buffer solution containing a mixture of Tris base and EDTA.

"L-Histidine buffer" is a solution containing L-histidine.

"DEP" is an abbreviation for dielectrophoresis.

"ACE" is Alternating Current Electrokinetics

EXAMPLES

Example 1: Formation of Hydrogel by Spin-Coating (Two Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a low rpm rate (1000-3000). The low rpm rate ensures that the height of the gel is in the range of 500 nm or greater.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. After a second layer of cellulose acetate is added, the chip is spun at a high rpm rate (9000-12000). The high rpm rate will ensure the height of the gel is in the range of 300 nm or less.

The chip with two layers of cellulose acetate is then dried at room temperature, in a convection oven, or in a vacuum oven.

Example 2: Formation of Hydrogel with Additives by Spin-Coating (Two Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a low rpm rate (1000-3000). The low rpm rate ensures that the height of the gel is in the range of 500 nm or greater.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. A low concentration (1-15%) of conductive polymer (PEDOT:PSS or similar) is added into the second cellulose acetate solution. After a second layer of cellulose acetate is added, the chip is spun at a high rpm rate (9000-12000). The high rpm rate will ensure the height of the gel is in the range of 300 nm or less.

The chip with two layers of cellulose acetate is then dried at room temperature, in a convection oven, or in a vacuum oven.

Example 3: Formation of Hydrogel with Additives by Spin-Coating (Three Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a high rpm rate (9000-12000). The low rpm rate ensures that the height of the gel is in the range of 300 nm or less.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. A low concentration (1-15%) of conductive polymer (PEDOT:PSS or similar) is added into the second cellulose acetate solution. After a second layer of cellulose acetate is added, the chip is spun at a low rpm rate (1000-3000). The low rpm rate will ensure that the height of the gel is in the range of 500 nm or greater.

The second coating of cellulose acetate is dried at room temperature, in a convection oven, or a vacuum oven. Optionally, the third layer of cellulose-acetate spin-coat is added immediately.

The third layer of cellulose acetate comprises a high concentration (≥2%) of cellulose acetate dissolved into a solvent such as Acetone, or an Acetone Ethanol mixture. The chip is spun at a high rpm rate (9000-12000). The low rpm rate ensures that the height of the gel is in the range of 300 nm or less.

The chip with three layers of cellulose acetate is then dried at room temperature, in a convection oven, or in a vacuum oven.

Example 4: Chip Construction

Figure 2:
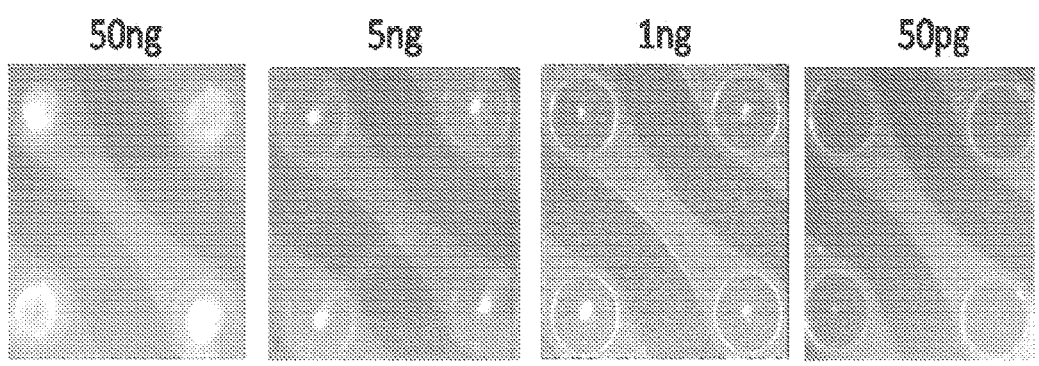
FIG. 2 shows the electrodes associated with various amounts of genomic DNA.
Figure 3:
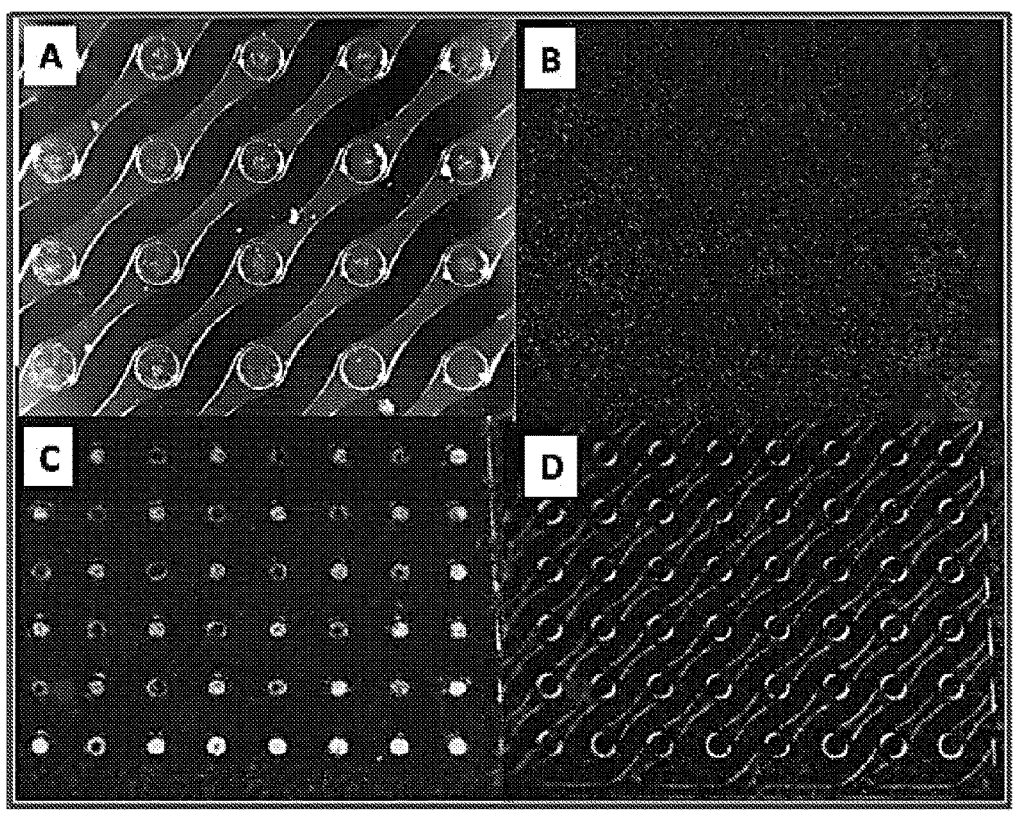
FIG. 3 shows isolation of green fluorescent *E. coli* on an array. Panel (A) shows a bright field view. Panel (B) shows a green fluorescent view of the electrodes before DEP activation. Panel (C) shows *E. coli* on the electrodes after one minute at 10 kHz, 20 Vp-p in 1×TBE buffer. Panel (D) shows *E. coli* on the electrodes after one minute at 1 MHz, 20 Vp-p in 1×TBE buffer.

For FIGS. 2 & 3: A 45×20 custom 80 μm diameter circular platinum microelectrode array on 200 um center-center pitch was fabricated based upon previous results (see references 1-3, below). All 900 microelectrodes are activated together and AC biased to form a checkerboard field geometry. The positive DEP regions occur directly over microelectrodes, and negative low field regions occur between microelectrodes. The array is over-coated with a 200 nm-500 nm thick porous poly-Hema hydrogel layer (Procedure: 12% pHema in ethanol stock solution, purchased from PolySciences Inc., that is diluted to 5% using ethanol. 70 uL of the 5% solution is spun on the above mentioned chip at a 6K RPM spin speed using a spin coater. The chip+hydrogel layer is then put in a 60° C. oven for 45 minutes) and enclosed in a microfluidic cartridge, forming a 50 μL sample chamber covered with an acrylic window (FIG. 1). Electrical connections to microelectrodes are accessed from Molex connectors from the PCB board in the flow cell. A function generator (HP 3245A) provided sinusoidal electrical signal at 10 KHz and 10-14V peak-peak, depending on solution conductivity. Images were captured with a fluorescent microscope (Leica) and an EGFP cube (485 nm emission and 525 nm excitation bandpass filters). The excitation source was a PhotoFluor II 200 W Hg arc lamp.

[1] R. Krishnan, B. D. Sullivan, R. L. Mifflin, S. C. Esener, and M. J. Heller, "Alternating current electrokinetic separation and detection of DNA nanoparticles in high-conductance solutions." Electrophoresis, vol. 29, pages 1765-1774, 2008.

[2] R. Krishnan and M. J. Heller, "An AC electrokinetic method for enhanced detection of DNA nanoparticles." J. Biophotonics, vol. 2, pages 253-261, 2009.

[3] R. Krishnan, D. A. Dehlinger, G. J. Gemmen, R. L. Mifflin, S. C. Esener, and M. J. Heller, "Interaction of nanoparticles at the DEP microelectrode interface under high conductance conditions" Electrochem. Comm., vol. 11, pages 1661-1666, 2009.

Example 5: Isolation of Human Genomic DNA

Human Genomic DNA (gDNA) was purchased from Promega (Promega, Madison, Wis.) and was sized to 20-40 kbp. (Sizing gel not shown.) The gDNA was diluted in DI water to the following concentrations: 50 nanograms, 5 nanograms, 1 nanogram, and 50 picograms. The gDNA was stained using 1×SYBR Green I green fluorescent double stranded DNA dye purchased from Invitrogen (Life Technologies, Carlsbad, Calif.). This mixture was then inserted into the microelectrode arrays and run at 14 Volts peak to peak (Vp-p), at 10 kHz sine wave for 1 minute. At the conclusion of 1 minute, a picture of the microelectrode pads was taken using a CCD camera with a 10× objective on a microscope using green fluorescence filters (FITC) so that the gDNA could be visualized (FIG. 2) The chip was able to identify down to 50 pg of gDNA in 50l water, i.e. 1 ng/mL concentration. Additionally, at 50 picograms, each microelectrode had on average ~60 femtograms of DNA since there are 900 microelectrodes on the array. The low-level concentration ability of the ACE device is well within the range of 1-10 ng/mL needed to identify Cfc-DNA biomarkers in plasma and serum (see references 4-6 below).

[4] T. L. Wu et al, "Cell-free DNA: measurement in various carcinomas and establishment of normal reference range." Clin Chim Acta., vol. 21, pages 77-87, 2002.

[5] R. E. Board et al, "DNA Methylation in Circulating Tumour DNA as a Biomarker for Cancer", Biomarker Insights, vol. 2, pages 307-319, 2007.

[6] O. Gautschi et al, "Circulating deoxyribonucleic Acid as prognostic marker in non-small-cell lung cancer patients undergoing chemotherapy." J Clin Oncol., vol. 22, pages 4157-4164, 2004.

Example 6: Isolation of DNA from *E. Coli*

Using the Chip and methods described in Examples 4 and 5, approximately 5000 green fluorescent *E. coli* cells in 50 uL of fluid was inserted into a chip and run using protocol described in caption for FIG. 3. Panel (A) shows a bright field view. Panel (B) shows a green fluorescent view of the electrodes before DEP activation. Panel (C) shows *E. coli* on the electrodes after one minute at 10 kHz, 20 Vp-p in 1×TBE buffer. Panel (D) shows *E. coli* on the electrodes after one minute at 1 MHz, 20 Vp-p in 1×TBE buffer.

Figure 4:
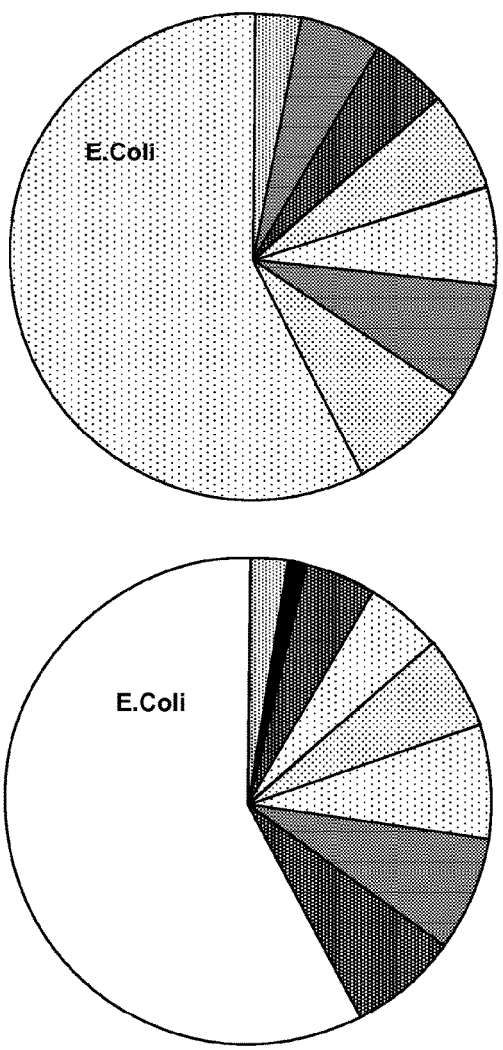
FIG. 4 shows a comparison between the methods of the present invention (top right panel) and the Epicentre™ WaterMaster™ DNA purification procedure (top left panel). The pie charts are the distribution of 10,000 Illumina™ sequencing reads BLAST searched against the MEGAN™ database. As shown, a similar percentage of sequencing reads originated from *E. coli* sequence for both methods. The table in the lower panel shows Sequencing coverage and quality of *E. Coli* run through the chip and compared to a control run outside the chip according to manufacturer's protocol.

The *E. coli* depicted in F 3 were lysed using a 100 milli-second 100V DC pulse using the HP 3245A function generator. The lysed particulates were then gathered on the electrode surface using 10 kHz, 10 Vp-p and the Illumina Nextera Protocol was used for library prep for sequencing while the DNA was on the chip (by inserting the appropriate buffers at the appropriate times onto the chip) to tag the DNA for Sequencing. The DNA was then eluted in 50 uL of 1×TBE Buffer and then PCR amplified for 9-12 cycles (using the Nextera Protocol) on a Bio-Rad PCR machine. The amplified DNA was then run on an Illumina GA II Sequencer. DNA from *E. Coli* was also isolated from 1×TBE buffer (10 million cells) using the Epicentre™ WaterMaster™ DNA purification procedure, to serve as a gold standard for comparison. The results are depicted in FIG. 4.

Example 7: Formation of Hydrogel with GVD

Figure 10:
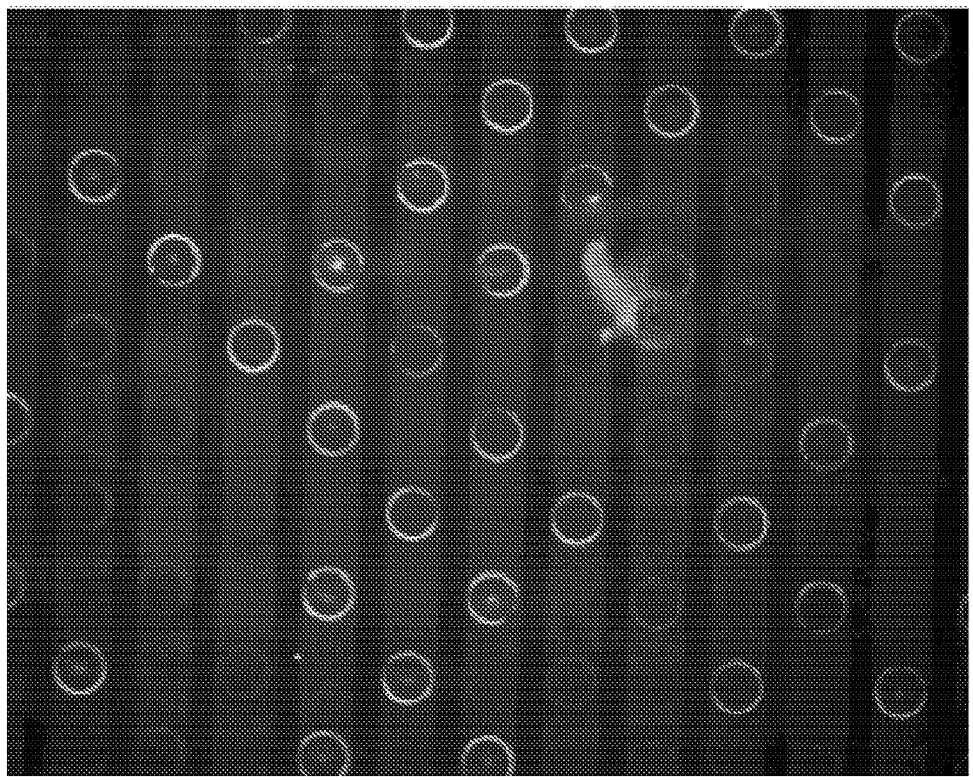
FIG. 10 exemplifies DNA capture on an electrode with a vapor deposited hydrogel layer. Vapor phase coatings of activated monomers form uniform thin film coatings on a variety of substrates. Hydrogels such as pHEMA were deposited in various thickness (100, 200, 300, 400 nm) and crosslinking (5, 25, 40%) density on electrode chips by GVD Corporation (Cambridge, Mass.). The hydrogel films were tested using a standard ACE protocol (no pretreatment, 7 Vp-p, 10 KHz, 2 minutes, 0.5×PBS, 500 ng/ml gDNA labeled with SYBR® Green 1). Fluorescence on the electrodes was captured by imaging. The 100 nm thickness, 5% crosslink gel device was found to have strong DNA capture. Optionally, the process could be optimized by changing the deposition rate or anchoring growth to the surface of the microelectrode array (i.e., to the passivation layer and exposed electrodes), using an adhesion promote such as a silane derivative.

Hydrogel, such as polyhydroxyethylmethacrylate (pHEMA) may also be layered onto the chip surface via vapor deposition using proprietary assays developed by GVD Corporation (Cambridge, Mass.) (see www.gvdcorp.com). Hydrogels such as pHEMA were deposited in various thickness (100, 200, 300, 400 nm) and crosslinking (5, 25, 40%) density on electrode chips was performed using technology developed by GVD Corporation. The hydrogel films were tested using a standard ACE protocol (no pretreatment, 7 Vp-p, 10 KHz, 2 minutes, 0.5×PBS, 500 ng/ml gDNA labeled with Sybr Green 1). Fluorescence on the electrodes was captured by imaging. FIG. 10 shows that 100 nm thickness, 5% crosslink gel device was found to have strong DNA capture. The process could also be optimized by changing the deposition rate or anchoring growth to the surface of the microelectrode array (i.e., to the passivation layer and exposed electrodes), using an adhesion promoter such as a silane derivative.

Example 8: Performance of Disclosed Device and Method v. Conventional Method

QIAGEN® circulating nucleic acid Purification kit (cat#55114) was used to purify 1 ml of plasma from chronic lymphocytic leukemia (CLL) patients, according to manufacturer's protocol. Briefly, incubation of 1 ml plasma with Proteinase K solution was performed for 30 minutes at 60° C. The reaction was quenched on ice and the entire volume was applied to a QIAamp Mini column connected to a vacuum. The liquid was pulled through the column and washed with 3 different buffers (600-750 ul each). The column was centrifuged at 20,000×g, 3 minutes and baked at 56° C. for 10 minutes to remove excess liquid. The sample was eluted in 55 μl of elution buffer with 20,000×g, 1 minute centrifugation. Total processing time was ~2.5 hours.

The chip die size was 10×12 mm, with 60-80 μm diameter Pt electrodes on 180-200 μm center-to-center pitch, respectively. The array was overcoated with a 5% pHEMA hydrogel layer (spun cast 6000 rpm from Ethanol solution, 12% pHEMA stock from Polysciences). The chip was pretreated using 0.5×PBS, 2V rms, 5 Hz, 15 seconds. The buffer was removed and 25 μl of CLL patient plasma was added. DNA was isolated for 3 minutes at 11 V p-p, 10 Khz, then washed with 500 μl of TE buffer at a 100 μl/min flow rate, with power ON. The voltage was turned off and the flow cell volume was eluted into a microcentrifuge tube. Total processing time was ~10 minutes.

The same process can be applied to fresh whole blood without modification. Ability to extract and purify DNA from whole undiluted blood is uniquely enabled by the chip technology disclosed herein.

DNA quantitation was performed on the Qiagen and chip elutes using PicoGreen according to manufacturer's protocol (Life Tech) (Table 2).

Subsequent gel electrophoresis, PCR and Sanger sequencing reactions showed similar performance for both extraction techniques with the chip being able to process whole blood as well as plasma. Mann-Whitney U non-parametric statistical test was also run between DNA amounts isolated from plasma using the Qiagen and chip techniques. There was no statistical difference (p<0.05 two-tailed) using either method of DNA purification.

TABLE 2

DNA purification, chip v. Qiagen
Values are in ng/ml and normalized to original plasma sample volume for comparison purposes.

| Patient | Chip - plasma | Qiagen - plasma | Chip - blood |
|---|---|---|---|
| normal A | 139 | 39 | 274 |
| normal B | 206 | 80 | 114 |
| normal C | 133 | 32 | 97 |
| TJK 528 | 320 | 547 | 167 |
| TJK 851 | 218 | 393 | 307 |
| TJK 1044 | 285 | 424 | 794 |
| TJK 334 | 261 | 1387 | 666 |
| TJK 613 | 179 | 53 | 257 |
| TJK 762 | 145 | 367 | 314 |
| TJK 847 | 886 | 1432 | 811 |
| TJK 248 | 84 | 119 | 448 |
| TJK 1024 | 302 | 169 | 332 |

TABLE 2-continued

DNA purification, chip v. Qiagen
Values are in ng/ml and normalized to original
plasma sample volume for comparison purposes.

| Patient | Chip - plasma | Qiagen - plasma | Chip - blood |
|---|---|---|---|
| TJK 1206 | 584 | 396 | 1435 |
| TJK 1217 | 496 | 146 | 584 |
| TJK 1262 | 87 | 84 | 1592 |
| TJK 1311 | 119 | 257 | 1825 |

Example 9: On-Chip Quantification Using Labeling and Fluorescence Microscopy

Figure 11:
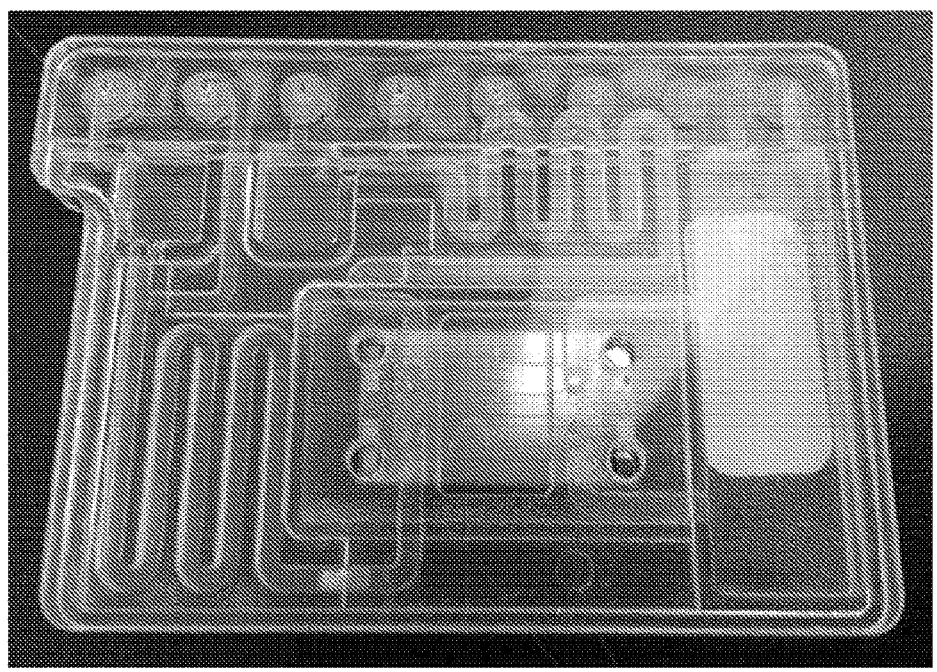
FIG. 11 shows a picture of a two-chamber fluidic cartridge showing the layout for the unknown (U) and known (K) chambers.

Using ACE microfluidic cartridges relative concentration of cell free biomarkers were determined in an unknown sample (sample can be whole blood, serum, plasma). The ACE microfluidic cartridge may be designed with one or more chambers for known standards and one or more chambers for the unknown sample as shown in FIG. 11.

Figure 12:
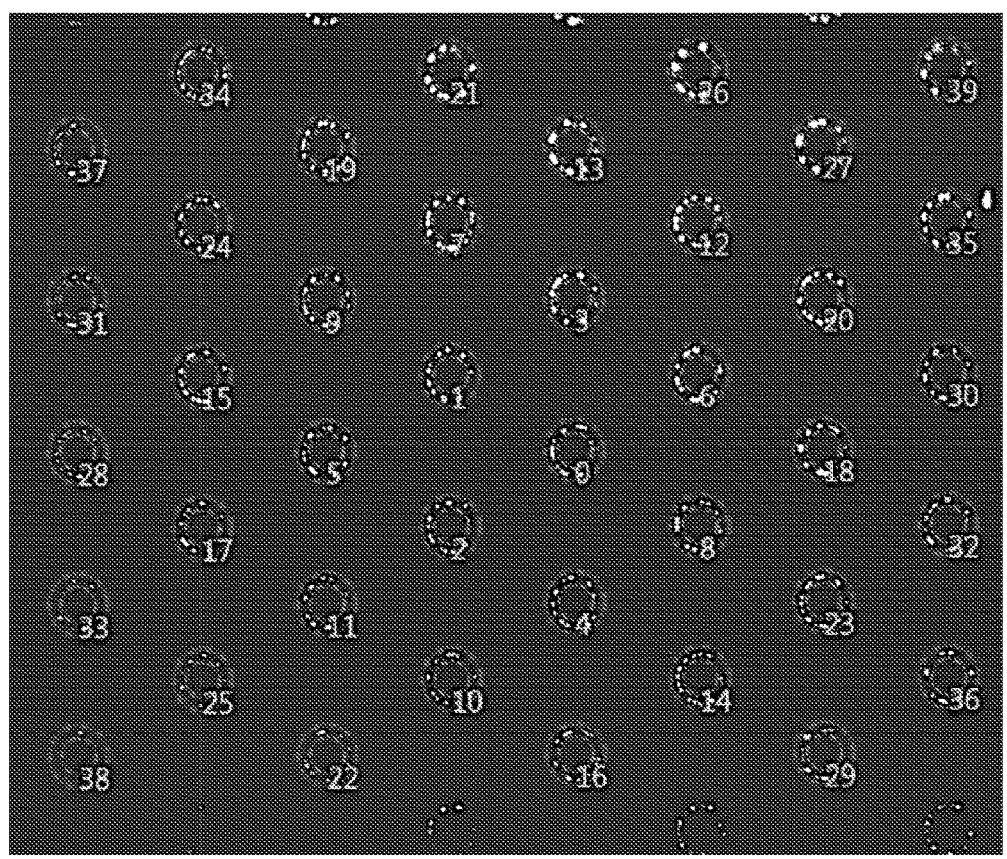
FIG. 12 shows a fluorescent image of YOYO®-1 labelled circulating cell-free DNA captured on electrodes. Region-of-Interest (ROI) segmentation enables rapid processing conversion from image to quantitative score.

An ACE field at 10 Vp-p and 10 kHz is applied to select microfluidic cartridge chambers and cell-free target biomarkers of interest are captured on the electrodes as shown in FIG. 12. A fluidic wash solution (water+osmolytes) is applied to wash away unwanted sample, i.e. particles and other components that are not captured on the electrodes. This fluidic wash is compatible with polymerase chain reaction (PCR) and next-generation sequencing thus allowing for secondary analysis post-elution.

Target biomarkers include proteins, lipids, antibodies, high molecular weight DNA (greater than 300 bp), tumor cells, exosomes, nucleosomes, nanosomes. For the fluorescent detection/quantification of such biomarkers specific dyes use such as YOYO®-1, SYBR® Green, CBQCA protein quantitation kit, SYTO® RNASelect™.

Figure 13:
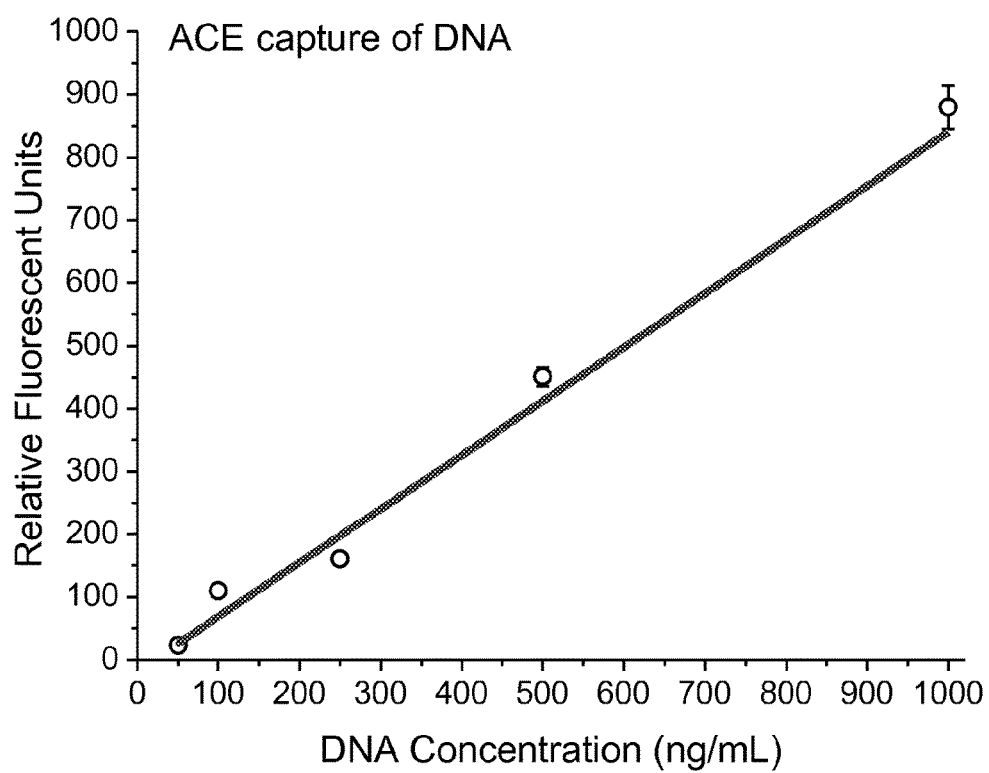
FIG. 13 illustrates the linear calibration for relative fluorescent units vs DNA concentration based on ROI segmentation of captured DNA on ACE electrodes.

Once excess unwanted sample is washed away, a CCD/CMOS/PMT detector is used in conjunction with fluorescence microscopy (with appropriate excitation/emission filters) to enable direct detection (binary) and/or quantification (concentration) of unknown analytes using a Region-of-Interest (ROI) image segmentation algorithm that compared pixel intensity between two regions in the electrodes (FIG. 12). Fluorescent quantification form both the known and unknown chambers is determined and the data is then compared using a linear fit calibration curve (FIG. 13) to create a relative ratio of intensity between the known chamber and the unknown chamber. Because the analytes in the known chamber have known specific concentrations of the cell free target biomarkers and the fluorescence labels are specific for the target analytes, using an algebraic relationship between intensities of the known chamber and the unknown chamber enable and the linear calibration curve the determination of analyte concentration from the unknown chamber.

Example 10: Off-Chip Quantification Using Q-PCR, RT-PCR and Sequencing

Using ACE microfluidic cartridges, relative concentrations of cell-free biomarkers were determined in an unknown sample. The sample may be whole blood, serum, plasma or other biological sample/fluid. The ACE microfluidic cartridge may be designed with one or more chambers for known standards and one or more chambers for the unknown sample.

An ACE field at 10 Vp-p and 10 kHz is applied to the chamber and cell-free target biomarkers of interest are captured on the electrodes (FIG. 12). A fluidic wash (water+osmolytes) is applied using a peristaltic pump while the ACE field is still on in order to remove all unwanted sample. This fluidic wash is compatible with polymerase chain reaction (PCR) and next-generation sequencing thus allowing for secondary analysis post-elution.

Figure 14:
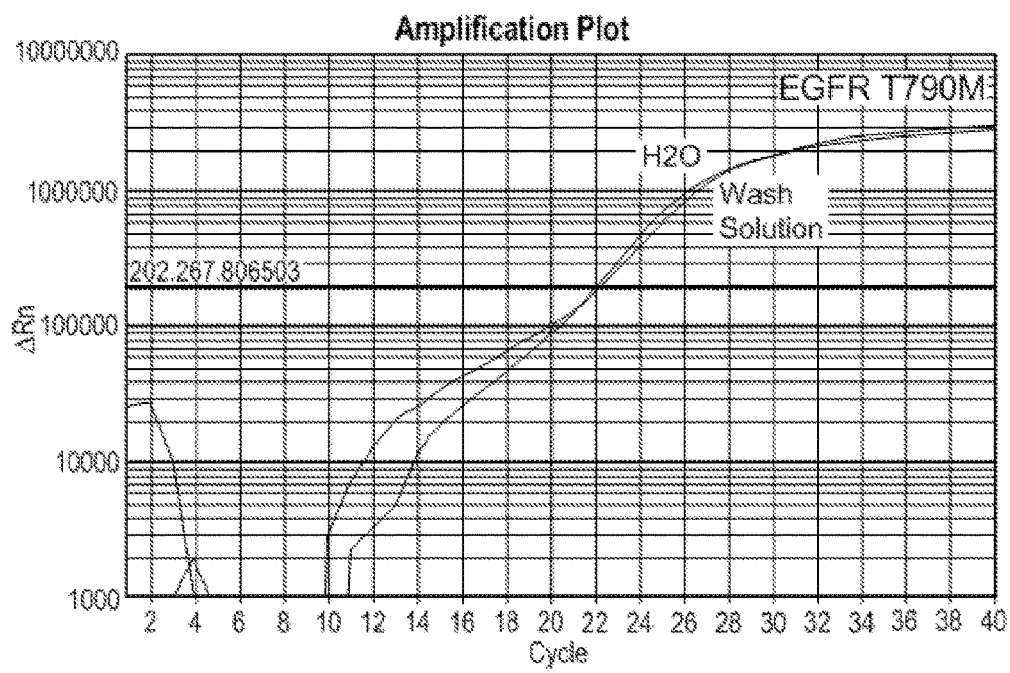
FIG. 14 shows the compatibility of the ACE fluidic wash solution with the downstream PCR mutation detection assays. DNA samples from the cell lines H1975, RKO, OCI-AML3 and HEL 92.1.7 were diluted in either $H_2O$ or ACE wash solution and used as positive controls for EGFR T790, BRAF V600, NPM1a and JAK2 617V assays, respectively.
Figure 14:
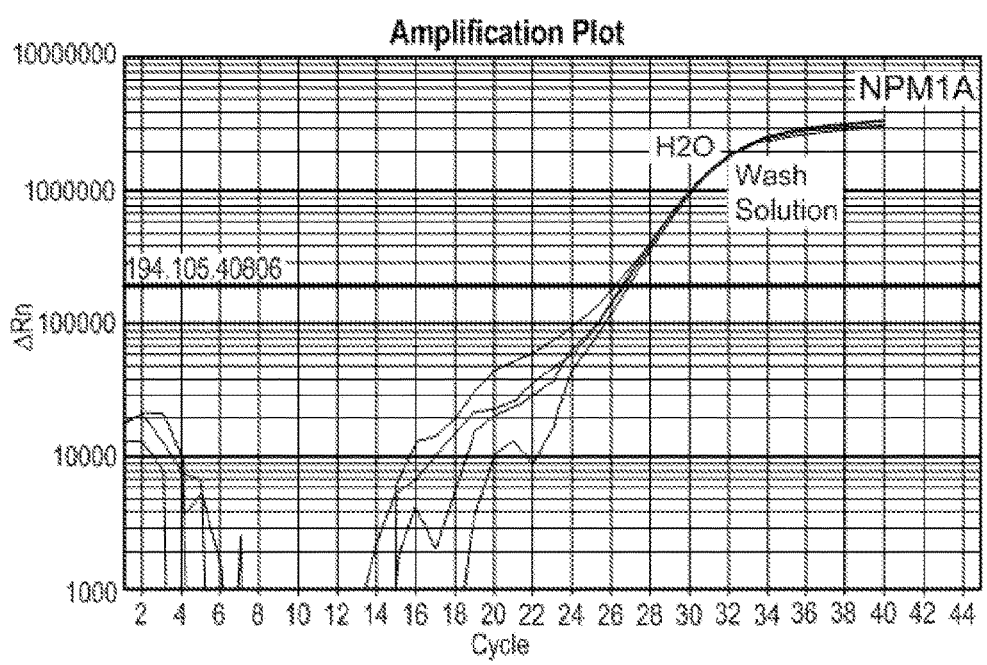
Figure 14:
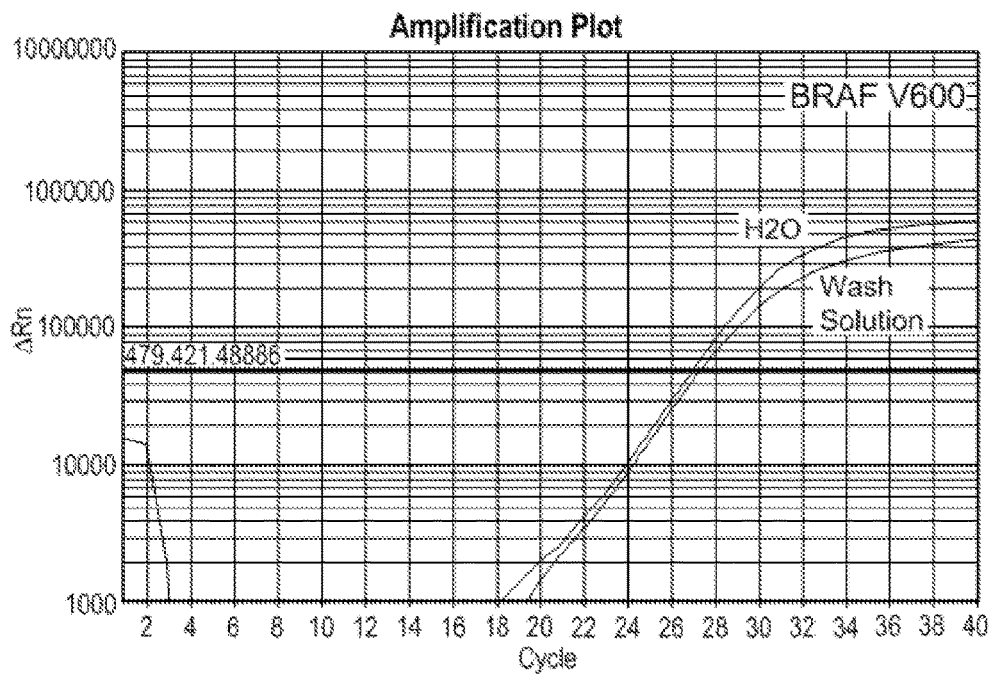
Figure 14:
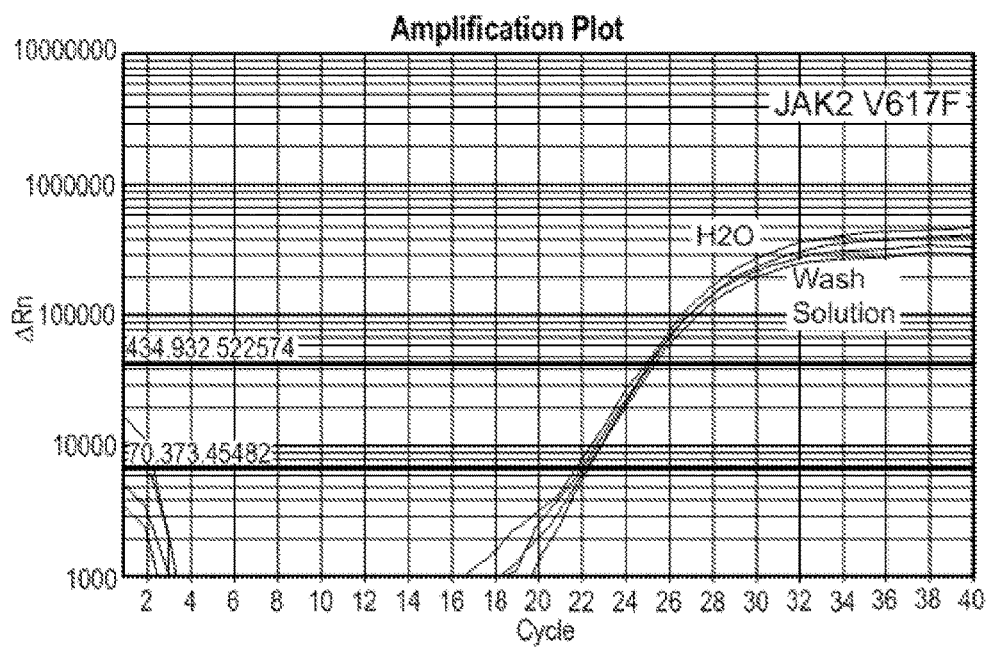

The ACE field is turned off and the captured particles are released into the PCR/Sequencing compatible solution. The unknown sample is eluted from the electrodes, and the sample used in PCR or next-gen sequencing analysis to determine specific gene sequences, alterations or deletions that may be present in the eluted dsDNA or RNA. FIG. 14 illustrates the usage of PCR technique for detection of PCR mutations for DNA samples from the cell lines H1975, RKO, OCI-AML3 and HEL 92.1.7 diluted in either $H_2O$ or ACE fluidic wash solution and used as positive controls for EGFR T790, BRAF V600, NPM1a and JAK2 617V assays.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting a cell free biomarker, the method comprising:
   a. applying a sample with a conductivity of greater than 100 mS/m to a device, the device comprising an array of electrodes capable of establishing an AC electrokinetic field region, the device further comprising at least two chambers, the sample applied to a first chamber;
   b. applying known quantities of a cell-free biomarker standard to a second chamber;
   c. establishing a first AC electrokinetic high field region in the first chamber, the first AC electrokinetic high field capable of isolating larger nanoparticulate molecular targets;
   d. establishing a second AC electrokinetic low field in the first chamber, the second AC electrokinetic low field capable of concentrating cells or micron-sized entities that may be present in the sample;
   e. establishing a third AC electrokinetic high field to the second chamber, the second AC electrokinetic high field isolating the molecular nucleic acid standard applied to the second chamber;
   f. flushing cells and micron-sized entities that may be present in the sample from the first chamber;
   g. detecting bound cell-free biomarker signal on the array in the first chamber and second chamber; and
   h. quantifying the bound cell-free biomarker by comparing the detected signal from the first chamber to detected signal from the second chamber.

2. The method of claim 1, wherein the cell-free biomarker is chosen from the group consisting of high molecular weight DNA, nucleosomes, exosomes, aggregated proteins, cell membrane fragments, mitochondria, cellular vesicles, and cellular debris.

3. The method of claim 1, wherein the cell-free biomarker is chosen from the group consisting of mutations, deletions, rearrangements, loss of heterozygosity, methylated nucleic acids, micro RNA, RNA from microvesicles, and combinations thereof.

4. The method of claim 1, wherein detection of the cell-free biomarker provides information useful for cancer diagnosis, cancer prognosis, or treatment response in a patient.

5. The method of claim 4, wherein the cell-free biomarker is associated with CNS tumors, neuroblastoma, gliomas, breast cancer, endometrial tumors, cervical tumors, ovarian tumors, hepatocellular carcinoma, pancreatic carcinoma, esophageal tumors, Stoch tumors, colorectal tumors, head and neck tumors, nasopharyngeal carcinoma, thyroid tumors, lymphoma, leukemia, lung cancer, non-small cell lung carcinoma, small cell lung carcinoma, testicular tumors, kidney tumors, prostate carcinoma, skin cancer, malignant melanoma, squamous cell carcinoma, or combinations thereof.

6. The method of claim 4, wherein the cell-free biomarker is GFAP, VEGF, EGFR, b-FGF, KRAS, YKL-40, MMP-9, or combinations thereof.

7. The method of claim 1, wherein the cell-free biomarker is chosen from the group consisting of proteins, lipids, antibodies, high molecular weight DNA, exosomes, nucleosomes, and nanosomes.

8. The method of claim 1, further comprising eluting the bound cell-free biomarker from the first chamber for further characterization.

9. The method of claim 8, wherein nucleic acid from the eluted cell-free biomarker is amplified or sequenced.

10. The method of claim 1, wherein the sample is whole blood, serum, plasma, cerebrospinal fluid, body tissue, urine, or saliva.

11. The method of claim 1, wherein the sample is blood.

12. The method of claim 1, wherein the AC electrokinetic field is produced using an alternating current having a voltage of 1 volt to 40 volts peak-peak, and/or a frequency of 5 Hz to 5,000,000 Hz and duty cycles from 5% to 50%.

13. The method of claim 1, wherein the conductivity of the fluid is greater than 500 mS/m.

14. The method of claim 1, wherein the array of electrodes is spin-coated with a hydrogel having a thickness from about 0.1 microns to about 1 micron.

15. The method of claim 14, wherein the hydrogel comprises two or more layers of a synthetic polymer.

16. The method of claim 14, wherein the hydrogel has a viscosity from about 0.5 cP to about 5 cP prior to spin-coating.

17. The method of claim 14, wherein the hydrogel has a conductivity from about 0.1 S/m to about 1.0 S/m.

18. The method of claim 1, wherein the bound cell-free biomarker comprises less than about 10% non-nucleic acid cellular material or cellular protein by mass.

19. The method of claim 1, wherein the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant.

20. The method of claim 1, wherein the array of electrodes comprises a passivation layer with a relative electrical permittivity from about 2.0 to about 4.0.

* * * * *